US008076114B2

(12) United States Patent
Farinas et al.

(10) Patent No.: US 8,076,114 B2

(45) **Date of Patent: *Dec. 13, 2011**

(54) CYTOCHROME P450 OXYGENASES

(75) Inventors: Edgardo T Farinas, Pasadena, CA (US); Frances H. Arnold, Pasadena, CA (US); Ulrich Schwaneberg, Ritterhude (DE); Anton Glieder, Gieiadorf (AT)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/754,216

(22) Filed: Apr. 5, 2010

(65) Prior Publication Data

US 2010/0248327 A1 Sep. 30, 2010

Related U.S. Application Data

(63) Continuation of application No. 11/800,970, filed on May 7, 2007, now Pat. No. 7,691,616, which is a continuation of application No. 10/201,213, filed on Jul. 22, 2002, now Pat. No. 7,226,768.

(60) Provisional application No. 60/306,766, filed on Jul. 20, 2001, provisional application No. 60/308,429, filed on Jul. 27, 2001.

(51) Int. Cl.

| | |
|---|---|
| ***C12N 9/02*** | (2006.01) |
| ***C12N 15/00*** | (2006.01) |
| ***C12N 1/20*** | (2006.01) |
| ***C12P 21/04*** | (2006.01) |
| ***C07H 21/04*** | (2006.01) |
| ***C12Q 1/26*** | (2006.01) |

(52) U.S. Cl. ........ 435/189; 435/25; 435/69.1; 435/71.1; 435/440; 435/252.3; 435/320.1; 536/23.2

(58) Field of Classification Search ........................ None
See application file for complete search history.

(56) References Cited

U.S. PATENT DOCUMENTS

| | | | |
|---|---|---|---|
| 4,599,342 | A | 7/1986 | LaHann |
| 5,605,793 | A | 2/1997 | Stemmer |
| 5,741,691 | A | 4/1998 | Arnold et al. |
| 5,785,989 | A | 7/1998 | Stanley et al. |
| 5,811,238 | A | 9/1998 | Stemmer et al. |
| 5,830,721 | A | 11/1998 | Stemmer et al. |
| 5,837,458 | A | 11/1998 | Minshull et al. |
| 5,965,408 | A | 10/1999 | Short |
| 6,090,604 | A | 7/2000 | Golightly et al. |
| 6,498,026 | B2 | 12/2002 | Delagrave et al. |
| 2005/0037411 | A1 | 2/2005 | Arnold et al. |
| 2005/0202419 | A1 | 9/2005 | Cirino et al. |

FOREIGN PATENT DOCUMENTS

| | | | |
|---|---|---|---|
| EP | 0505198 | A1 | 9/1992 |
| EP | 0752008 | B1 | 2/1997 |
| WO | 8903424 | A1 | 4/1989 |
| WO | 9522625 | A1 | 8/1995 |
| WO | 9716553 | A1 | 5/1997 |
| WO | 9720078 | A1 | 6/1997 |
| WO | 9735957 | A1 | 10/1997 |
| WO | 9735966 | A1 | 10/1997 |
| WO | 9827230 | A1 | 6/1998 |
| WO | 9831837 | A1 | 7/1998 |
| WO | 9841653 | A1 | 9/1998 |
| WO | 9842832 | A1 | 10/1998 |
| WO | 9960096 | A2 | 11/1999 |
| WO | 0000632 | A1 | 1/2000 |
| WO | 0004190 | A1 | 1/2000 |
| WO | 0006718 | A2 | 2/2000 |
| WO | 0009679 | A1 | 2/2000 |
| WO | 0018906 | A3 | 4/2000 |
| WO | 0031273 | A2 | 6/2000 |
| WO | 0162938 | A2 | 8/2001 |

OTHER PUBLICATIONS

March, J., Advanced Organic Chemistry: Reactions, Mechanisms, and Structure, 4th Edition, 1992, pp. 882-884, Wiley and Sons, NY.
March, J., Advanced Organic Chemistry: Reactions, Mechanisms, and Structure, 4th Edition, 1992, pp. 1072-1074, Wiley and Sons, NY.
Martin, B. et al., "Highly swelling hydrogels from ordered galactose-based polyacrylates," Biomaterials, 1998, pp. 69-76, 19(1-3), Elsevier.
Martineau, P. et al., "Expression of an Antibody Fragment at High Levels in the Bacterial Cytoplasm," J. Mol. Biol., 1998, pp. 117-127, vol. 280, No. 1, Academic Press.
Martinez, C. et al., "Cytochrome P450's: Potential Catalysts for Asymmetric Olefin Epoxidations," Current Organic Chemistry, 2000, pp. 263-282, vol. 4, No. 3, Bentham Science Publishers B.V.
Matson, R. et al., "Characteristics of a Cytochrome P-450-Dependent Fatty Acid ω-2 Hydroxylase From *Bacillus megaterium*," Biochimica et Biophysica Acta, 1977, pp. 487-494, 487, Elsevier/North Holland Biomedical Press.
Mazur, A., "Chapter 8, Galactose Oxidase," ACS Symposium Series 466—Enzymes in Carbohydrate Synthesis, 1991, pp. 99-110, American Chemical Society, Washington, DC, USA.
Mazur, A., et al., "Chemoenzymic Approaches to the Preparation of 5-C-(Hydroxymethyl)hexoses," J. Org. Chem., 1997, pp. 4471-4475, vol. 62, No. 13, American Chemical Society, Washington, DC, USA.
McPherson, M. et al., "Galactose Oxidase of Dactylium dendroides," Apr. 1992, pp. 8146-8152, The Journal of Biological Chemistry, vol. 267, No. 12, The American Society for Biochemistry and Molecular Biology, Inc.

(Continued)

*Primary Examiner* — Yong Pak
(74) *Attorney, Agent, or Firm* — Joseph R. Baker, Jr.; Gavrilovich Dodd & Lindsey LLP

(57) ABSTRACT

Nucleic acids encoding cytochrome P450 variants are provided. The cytochrome P450 variants of have a higher alkane-oxidation capability, alkene-oxidation capability, and/or a higher organic-solvent resistance than the corresponding wild-type or parent cytochrome P450 enzyme. A preferred wild-type cytochrome P450 is cytochrome P450 BM-3. Preferred cytochrome P450 variants include those having an improved capability to hydroxylate alkanes and epoxidate alkenes comprising less than 8 carbons, and have amino acid substitutions corresponding to V78A, H236Q, and E252G of cytochrome P450 BM-3. Preferred cytochrome P450 variants also include those having an improved hydroxylation activity in solutions comprising co-solvents such as DMSO and THF, and have amino acid substitutions corresponding to T235A, R471A, E494K, and S1024E of cytochrome P450 BM-3.

10 Claims, 36 Drawing Sheets

OTHER PUBLICATIONS

McPherson, M. et al., "Galactose oxidase: Molecular analysis and mutagenesis studies," Biochemical Society Transactions, 646th Meeting Leeds, 1993, pp. 1992-1994, vol. 21, The Biochemical Society, Portland Press.
Meinhold, P. et al., "Direct Conversion of Ethane to Ethanol by Engineered Cytochrome P450 BM3," ChemBioChem, 2005, pp. 1-4, vol. 6, Wiley-VCH Verlag GmbH & Co. Weinheim, Germany.
Mendonca, M. et al., "Purification and Characterization of Intracellular Galactose Oxidase from Dactylium dendroides," Archives of Biochemistry and Biophysics, Feb. 1987, pp. 507-514, vol. 252, No. 2, Academic Press, Inc.
Mendonca, M. et al., "Role of Carbohydrate Content on the Properties of Galactose Oxidase from Dactylium dendroides," Archives of Biochemistry and Biophysics, Nov. 1988, pp. 427-434, vol. 266, No. 2, Academic Press, Inc.
Miele, R., et al., "Glycosylation of Asparagine-28 of Recombinant Staphylokinase with High-Mannose-type Oligosaccharides Results in a Protein with Highly Attenuated Plasminogen Activator Activity," Journal of Biological Chemistry, Mar. 1999, pp. 7769-7776, vol. 274, No. 12, The American Society for Biochemistry and Molecular Biology, Inc.
Miles, C. et al., "Protein engineering of cytochromes P-450," Biochimica et Biophysica Acta 1543, 2000, pp. 383-407.
Minshull, J. et al., "Protein evolution by molecular breeding," Chemical Biology, 1999, pp. 284-290, 3, Elsevier Science Ltd.
Mitraki, A. et al., "Amino acid substitutions influencing intracellular protein folding pathways," FEBS Letters, Jul. 1992, pp. 20-25, vol. 307, No. 1, Elsevier Science Publishers B.V.
Miura, Yoshiro, et al., "ω-1, ω-2 and ω-3 hydroxylation of long-chain fatty acids, amides and alcohols by a soluble enzyme system from *Bacillus megaterium*," Biochimica et Biophysica Acta 388, 1975, pp. 305-317.
Miyazaki, K. et al., "Directed Evolution Study of Temperature Adaptation in a Psychrophilic Enzyme," Journal Mol. Biol., 2000, pp. 1015-1026, 297, Academic Press.
Modi, S. et al., "NMR Studies of Substrate Binding to Cytochrome P450 BM3: Comparisons to Cytochrome P450 cam," Biochemistry, 1995, pp. 8982-8988, vol. 34, No. 28, American Chemical Society.
Moore, J. et al., "Directed evolution of a para-nitrobenzyl esterase for aqueous-organic solvents," Nature Biotechnology, Apr. 1996, pp. 458-467, vol. 14.
Moore, J. et al., "Strategies for the in vitro Evolution of Protein Function: Enzyme Evolution by Random Recombination of Improved Sequences," J. Mol. Biol., 1997, pp. 336-347, 272, Academic Press Limited.
Moser, Christopher, et al., "Biological Electron Transfer," Journal of Bioenergetics and Biomembranes, vol. 27, No. 3, 1995, pp. 263-274.
Munro, A. et al., "Probing electronic transfer in flavocytochrome P-450 BM3 and its component domains," Eur. J. Biochem., 1996, pp. 403-409, FEBS.
Munro, A. et al., "Alkane Metabolism by Cytochrome P450 BM3," Biochemical Society Transactions, 1993, p. 412S, 21.
Murrell, J. et al., "Molecular biology and regulation of methane monooxygenase," Arch. Microbiol., 2000, pp. 325-332, 173o.
Nagayama, Y. et al., "Role of Asparagine-linked Oligosaccharides in Protein Folding, Membrane Targeting, and Thyrotropin and Autoantibody Binding of the Human Thyrotropin Receptor," Journal of Biological Chemistry, Dec. 1998, pp. 33423-33428, vol. 273, No. 5, The American Society for Biochemistry and Molecular Biology, Inc.
Nakagawa, S. et al., "Construction of Catalase Deficient *Escherichia coli* Strains for the Production of Uricase," Biosci. Biotech. Biochem., 1996, pp. 415-420, 60 (3), Japanese Society for Bioscience, Biotechnology and Agrochemistry.
Nakajima, H. et al., "Industrial Application of Adenosine 5'-Triphosphate Regeneration to Synthesis of Sugar Phosphates," ACS Symposium Series 466, Enzymes in Carbohydrate Synthesis, Chapter 9, pp. 110-120, American Chemical Society, Washington DC, 1991, Bednarski & Simon, Editors.
Narhi, L. et al., "Identification and Characterization of Two Functional Domains in Cytochrome P-450BM-3, a Catalytically Self-sufficient Monooxygenase Induced by Barbiturates in *Bacillus megaterium*," The Journal of Biological Chemistry, May 1987, pp. 6683-6690, vol. 262, No. 14, The American Society of Biological Chemists, Inc.
Narhi, L. et al., "Characterization of a Catalytically Self-sufficient 199,000-Dalton Cytochrome P-450 Monooxygenase Induced by Barbiturates in *Bacillus megaterium*," The Journal of Biological Chemistry, Jun. 1986, pp. 7160-7169, vol. 261, No. 16, The American Society of Biological Chemists, Inc.
Nelson, D., "Appendix A—Cytochrome P450 Nomenclature and Alignment of Selected Sequences," Cytochrome P450: Structure, Mechanism, and Biochemistry, Second Ed., 1995, pp. 575-606, Plenum Press, NY.
Ness, J. et al., "DNA shuffling of subgenomic sequences of subtilisin," Nature Biotechnology, Sep. 1999, pp. 893-896, vol. 17, No. 9, Nature Publishing Group.
Noble, M. et al., "Roles of key active-site residues in flavocytochrome P450 BM3," Biochem. J., 1999, pp. 371-379, 339, Biochemical Society.
Oliphant, A. et al., "Cloning of random-sequence oligodeoxynucleotides," Gene, 1986, pp. 177-183, 44, Elsevier Science Publishers B.V.
Oliver, C. et al., "Engineering the substrate specificity of *Bacillus megaterium* cytochrome P-450 BM3: hydroxylation of alkyl trimethylammonium compounds," Biochem. J., 1997, pp. 537-544, 327, The Biochemical Society, London, England.
Omura, T. et al., "The Carbon Monoxide-binding Pigment of Liver Microsomes," The Journal of Biological Chemistry, Jul. 1964, pp. 2370-2378, vol. 239, No. 7, The American Society for Biochemistry and Molecular Biology.
Ortlepp, S. et al., "Expression and characterization of a protein specified by a synthetic horseradish peroxidase gene in *Escherichia coli*," Journal of Biotechnology, 1989, pp. 353-364, 11, Elsevier Science Publishers B.V.
Ost, T. et al., "Rational re-design of the substrate binding site of flavocytochrome P450 BM3," FEBS Letters, 2000, pp. 173-177, 486, Elsevier Science B.V.
Ostermeier, M. et al., "Incremental Truncation as a Strategy in the Engineering of Novel Biocatalysts," Bioorganic & Medicinal Chemistry, 1999, pp. 2139-2144, 7, Elsevier Science Ltd.
Parekh, R. et al., "Multicopy Overexpression of Bovine Pancreatic Trypsin Inhibitor Saturates the Protein Folding and Secretory Capacity of *Saccharomyces cerevisiae*," Protein Expression and Purification, 1995, pp. 537-545, 6, Academic Press.
Patten, P. et al., "Applications of DNA shuffling to pharmaceuticals and vaccines," Biotechnology, 1997, pp. 724-733, vol. 8, Elsevier Science Ltd.
Paulsen, M. et al., "Dramatic Differences in the Motions of the Mouth of Open and Closed Cytochrome P450BM-3 by Molecular Dynamics Simulations," PROTEINS: Structure, Function and Genetics, 1995, pp. 237-243, Wiley-Liss, Inc.
Peterson, J. et al., "Chapter 5—Bacterial P450s—Structural Similarities and Functional Differences", Cytochrome P450: Structure, Mechanism, and Biochemistry, Second Ed., 1995, pp. 151-180.
Rathore, D., et al., "Expression of Ribonucleolytic Toxin Restrictocin in *Escherichia coli*: Purification and Characterization," FEBS Letters, 1996, pp. 259-262, vol. 392, Federation of European Biochemical Societies.
Reynolds, M., et al., "Structure and Mechanism of Galactose Oxidase: Catalytic Role of Tyrosine 495," JBIC, 1997, pp. 327-335, vol. 2.
Rodriguez-Lopez, J., et al., "Role of Arginine 38 in Horseradish Peroxidase—A Critical Residue for Substrate Binding and Catalysis," The Journal of Biological Chemistry, Feb. 23, 1996, pp. 4023-4030, vol. 271, No. 8, The American Society for Biochemistry and Molecular Biology.
Romanos, M., et al., "Foreign Gene Expression in Yeast: a Review," Yeast, Jun. 1992, pp. 423-488, vol. 8, No. 6, John Wiley & Sons Ltd.
Root, R., et al., "Enzymatic Synthesis of Unusual Sugars: Galactose Oxidase Catalyzed Stereospecific Oxidation of Polyols," Journal of the American Chemical Society, 1985, pp. 2997-2999, vol. 107, No. 10, American Chemical Society.
Ruettinger, R., et al., "Coding Nucleotide, 5' Regulatory, and Deduced Amino Acid Sequences of P-450BM-3, a Single Peptide Cytochrome P-450:NADPH-P-450 Reductase from *Bacillus megaterium*," The Journal of Biological Chemistry, Jul. 5, 1989, pp. 10987-10995, vol. 264, No. 19, The American Society for Biochemistry and Molecular Biology, Inc.
Ruettinger, R., et al., "Epoxidation of Unsaturated Fatty Acids by a Soluble Cytochrome P-450-dependent System from *Bacillus megaterium*," The Journal of Biological Chemistry, Jun. 10, 1981, pp. 5728-5734, vol. 256, No. 11.
Said, I.T., et al., "Comparison of Different Techniques for Detection of Gal—GalNAc, an Early Marker of Colonic Neoplasia," Histology and Histopathology, Apr. 1999, pp. 351-357, vol. 14, No. 2, Jiménez Godoy, S.A.
Savenkova, M., et al. "Improvement of Peroxygenase Activity by Relocation of a Catalytic Histidine within the Active Site of Horseradish Peroxidase," Biochemistry, 1998, pp. 10828-10836, vol. 37, American Chemical Society.
Saysell, C., et al., "Properties of the Trp290His Variant of Fusarium NRRL 2903 Galactose Oxidase: Interactions of the GOasesemi State with Different Buffers, Its Redox Activity and Ability to Bind Azide," JBIC, 1997, pp. 702-709, vol. 2.
Schatz, P., et al., "Genetic Analysis of Protein Export in *Escherichia coli*," Annual Review of Genetics, 1990, pp. 215-248, vol. 24, Annual Reviews, Inc., Palo Alto, CA.
Schein C., "Solubility as a Function of Protein Structure and Solvent Components," Bio/Technology, Apr. 1990, pp. 308-317, vol. 8, No. 4.
Scheller, U., et al., "Characterization of the n-Alkane and Fatty Acid Hydroxylating Cytochrome P450 Forms 52A3 and 52A4," Archives of Biochemistry and Biophysics, Apr. 15, 1996, pp. 245-254, vol. 328, No. 2, Academic Press, Inc.
Schlegel, R., et al., "Substrate Specificity of D-Galactose Oxidase," Carbohydrate Research, Jun. 1968, pp. 193-199, vol. 7, No. 2, Elsevier Publishing Company, Amsterdam.
Schmid, A., et al., "Industrial Biocatalysis Today and Tomorrow," Nature, Jan. 11, 2001, pp. 258-268, vol. 409, Macmillian Magazines Ltd.
Schneider, S., et al., "Controlled Regioelectivity of Fatty Acid Oxidation by Whole Cells Producing Cytochrome P450BM-3 Monooxygenase Under Varied Dissolved Oxygen Concentrations," Biotechnology and Bioengineering, Aug. 5, 1999, pp. 333-341, vol. 64, No. 3, John Wiley & Sons, Inc.
Schwaneberg, U., et al., "A Continuous Spectrophotometric Assay for P450 BM-3, a Fatty Acid Hydroxylating Enzyme, and Its Mutant F87A," Analytical Biochemistry, 1999, pp. 359-366, vol. 269, Academic Press.
Schwaneberg, U., et al., "Cost-Effective Whole-Cell Assay for Laboratory Evolution of Hydroxylases in *Escherichia coli*," Journal of Biomolecular Screening, 2001, pp. 111-117, vol. 6, No. 2, The Society for Biomolecular Screening.
Shafikhani, S., et al., "Generation of Large Libraries of Random Mutants in *Bacillus subtilis* by PCR-Based Plasmid Multimerization," BioTechniques, Aug. 1997, pp. 304-310, vol. 23, No. 2.
Shanklin, J., et al., "Mössbauer Studies of Alkane ω-Hydroxylase: Evidence for a Diiron Cluster in an Integral-Membrane Enzyme," Proc. Natl. Acad. Sci. USA, Apr. 1997, pp. 2981-2986, vol. 94.
Shao, Z., et al., "Random-priming in Vitro Recombination: An Effective Tool for Directed Evolution," Nucleic Acids Research, Jan. 15, 1998, pp. 681-683, vol. 26, No. 2, Oxford University Press.
Shilov, A., et al., "Activation of C—H Bonds by Metal Complexes," Chem. Rev., 1997, pp. 2879-2932, vol. 97, American Chemical Society.
Shindler, J., et al., "Peroxidase from Human Cervical Mucus—The Isolation and Characterisation," European Journal of Biochemistry, Jun. 1976, pp. 325-331, vol. 65, No. 2.
Sirotkin, K., Advantages to Mutagenesis Techniques Generating Populations Containing the Complete Spectrum of single Codon Changes, J. Theor. Biol., 1986, pp. 261-279, vol. 123, Academic Press Inc. (London) Ltd.
Smith, A., et al., "Expression of a Synthetic Gene for Horseradish Peroxidase C in *Escherichia coli* and Folding and Activation of the Recombinant Enzyme with Ca2-30 and Heme," The Journal of Biological Chemistry, Aug. 5, 1990, pp. 13335-13343, vol. 265, No. 22, The American Society for Biochemistry and Molecular Biology.
Smith, A., et al., "Substrate Binding and Catalysis in Heme Peroxidases," Current Opinion in Chemical Biology, (1998), pp. 269-278, vol. 2.
Spiro, T., et al., "Is the CO Adduct of Myoglobin Bent, and Does It Matter?," Accounts of Chemical Research, 2001, pp. 137-144, vol. 34, No. 2, American Chemical Society.
Staijen, I., et al., "Expression, Stability and Performance of the Three-Component Alkane Mono-oxygenase of Pseudomonas oleovorans in *Escherichia coli*," Eur. J. Biochem., 2000, pp. 1957-1965, vol. 267.
Stemmer, W., "DNA Shuffling by Random Fragmentation and Reassembly: In Vitro Recombination for Molecular Evolution," Proc. Natl. Acad. Sci. USA, Oct. 25, 1994, pp. 10747-10751, vol. 91, No. 22.
Stemmer, W., "Rapid Evolution of a Protein In Vitro by DNA Shuffling," Nature, Aug. 4, 1994, pp. 389-391, vol. 370, No. 6488.
Stemmer, W., et al., "Selection of an Active Single Chain Fv Antibody from a Protein Linker Library Prepared by Enzymatic Inverse PCR," BioTechniques, 1993, pp. 256-265, vol. 14, No. 2.
Stevenson, J., et al., "The Catalytic Oxidation of Linear and Branched Alkanes by Cytochrome P450cam," J. Am. Chem. Soc., 1996, pp. 12846-12847, vol. 118, No. 50, American Chemical Society.
Studier, F., et al., "Use of T7 RNA Polymerase to Direct Expression of Cloned Genes," Methods in Enzymology, 1990, pp. 60-89, vol. 185, Academic Press, Inc.
Sun, L., et al., "Expression and Stabilization of Galactose Oxidase in *Escherichia coli* by Directed Evolution," Protein Engineering, Sep. 2001, pp. 699-704, vol. 14, No. 9, Oxford University Press.
Sun, L., et al., "Modification of Galactose Oxidase to Introduce Glucose 6-Oxidase Activity," ChemBioChem: A European Journal of Chemical Biology, Aug. 2, 2002, pp. 781-783, vol. 3, No. 8, Wiley-VCH-Vertag GmbH, Weinheim, Germany.
Szabó, E., et al., "Application of Biosensor for Monitoring Galactose Content," Biosensors & Bioelectronics, 1996, pp. 1051-1058, vol. 11, No. 10, Elsevier Science Limited.
Tams, J., et al., "Glycosylation and Thermodynamic Versus Kinetic Stability of Horseradish Peroxidase," FEBS Letters, 1998, pp. 234-236, vol. 421, Federation of European Biochemical Societies.
Thatcher, D., et al., "Protein Folding in Biotechnology," Mechanisms of Protein Folding, 1994, pp. 229-261, IRL Press, Oxford.
Tkac, J., et al., "Rapid and Sensitive Galactose Oxidase-Peroxidase Biosensor for Galactose Detection with Prolonged Stability," Biotechnology Techniques, 1999, pp. 931-936, Kluwer Academic Publishers.
Tonge, G., et al., "Purification and Properties of the Methane Monooxygenase enzyme System from Methylosinus trichosporium OB3b," Biochem. J., 1977, pp. 333-344, vol. 161.
Tressel, P., et al., "A Simplified Purification Procedure for Galactose Oxidase," Analytical Biochemistry, Jun. 1980, pp. 150-153, vol. 105, No. 1, Academic Press, Inc.
Truan, G., et al., "Thr268 in Substrate Binding and Catalysis in P450BM-3," Archives of iochemistry and Biophysics, Jan. 1, 1998, pp. 53-64, vol. 349, No. 1, Academic Press.
Vega, F., et al., "On-line Monitoring of Galactoside Conjugates and Glycerol by Flow Injection Analysis," Analytica Chimica Acta, 1998, pp. 57-62, vol. 373, Elsevier Science B.V.
Vrbová, E., et al., "Preparation and Utilization of a Biosensor Based on Galactose Oxidase," Collect. Czech. Chem. Commun., 1992, pp. 2287-2294, vol. 57.
Wachter, R., et al., "Molecular Modeling Studies on Oxidation of Hexopyranoses by Galactose Oxidase. An Active Site Topology Apparently Designed to Catalyze Radical Reactions, Either Concerted or Stepwise," Journal of the American Chemical Society, Mar. 9, 1996, pp. 2782-2789, vol. 118, No. 9.
Watkinson, R., et al., "Physiology of Aliphatic Hydrocarbon-Degrading Microorganisms," Biodegradation, 1990, pp. 79-92, vol. 1, Nos. 2/3, Kluwer Academic Publishers.
Welinder, K., "Amino Acid Sequence Studies of Horseradish Peroxidase," European Journal of Biochemistry, 1979, pp. 483-502.
Wetzel, R., et al., "Mutations in Human Interferon Gamma Affecting Inclusion Body Formation Identified by a General Immunochemical Screen," Bio/Technology, Aug. 1991, pp. 731-737, vol. 9.

Whittaker, M., et al., "The Active Site of Galactose Oxidase," The Journal of Biological Chemistry, 1988, pp. 6074-6080, vol. 263, No. 13, The American Society for Biochemistry and Molecular Biology, Inc.
Whittaker, M., et al., "Kinetic Isotope Effects as probes of the Mechanism of Galactose Oxidase," Biochemistry, 1998, pp. 8426-8436, vol. 37, American Chemical Society.
Wilkinson, D., et al., "Structural and Kinetic Studies of a Series of Mutants of Galactose Oxidase Identified by Directed Evolution," Protein Engineering, Design & Selection, Jan. 12, 2004, pp. 141-148, vol. 17, No. 2, Oxford University Press.
Yang, G., et al., "Gal—GalNAc: A biomarker of Colon Carcinogenesis," Histology and Histopathology, 1996, pp. 801-806, vol. 11.
Yano, T., et al., "Directed Evolution of an Aspartate Aminotransferase with New Substrate Specificities," Proc. Natl. Acad. Sci. USA, May 1998, pp. 5511-5515, vol. 95.
Yeom, H., et al., "Oxygen Activation by Cytochrome P450BM-3: Effects of Mutating an Active Site Acidic Residue," Archieves of Biochemistry and Biophysics, Jan. 15, 1997, pp. 209-216, vol. 337, No. 2, Academic Press.
Adam et al., "Microbial Asymmetric CH Oxidations of Simple Hydrocarbons: A Novel Monooxygenase Activity of the Topsoil Microorganism *Bacillus megaterium*," Eur. J. Org. Chem., 2000, pp. 2923-2926, Wiley-VCH Verlag GmbH, Weinheim, Germany.
Aisaka et al., "Production of Galactose Oxidase by Gibberella fujikuroi," Agric, Biol. Chem., 1981, pp. 2311-2316, 45 (10).
Amaral et al., "Galactose Oxidase of Polyporus circinatus1-4," Methods in Enzymology, Carbohydrate Metabolism, 1966, pp. 87-92, vol. 9, Academic Press Inc., New York, NY, USA.
Anfinsen, "Principles that Govern the Folding of Protein Chains," Science, Jul. 20, 1973, pp. 223-230, vol. 181, No. 4096, American Asso for the Advancement of Science, Washington, DC, USA.
Appel et al., "A P450 BM-3 mutant hydroxylates alkanes, cycloalkanes, arenas and heteroarenes," Journal of Biotechnology, 2001, pp. 167-171, Elsevier Science B.V.
Arkin et al., "An algorithm for protein engine ring: Simulations of recursive ensemble mutagenesis," Proc. Natl. Acad. Sci.—USA, Aug. 1992, pp. 7811-7815, vol. 89, Applied Biological Sciences.
Arnold, "Design by Directed Evolution," Accounts of Chemical Research, 1998, pp. 125-131, vol. 31, No. .3 American Chemical Society.
Arnold, "Engineering proteins for nonnatural environments," The FASEB Journal, Jun. 1993, pp. 744-749, vol. 7, No. 6, FASEB, Bethesda, MD, USA.
Arnold et al., "Optimizing Industrial Enzymes by Directed Evolution," Advances in Biochemical Engineering/Biotechnology, 1997, pp. 1-14, vol. 58, Springer-Verlag, Berlin, Germany.
Arts et al., "Hydrogen Peroxide and Oxygen in Catalytic Oxidation of Carbohydrates and Related Compounds," Synthesis Journal of Synthetic Organic Chemistry, Jun. 1997, pp. 597-613.
Ashraf et al., "Bacterial oxidation of propane," FEMS Microbiology Letters, 1994, pp. 1-6, Federation of European Microbiological Societies, Elsevier.
Avigad, "Oxidation Rates of Some Desialylated Glycoproteins by Galactose Oxidase," Archives of Biochemistry and Biophysics, Jun. 1985, pp. 531-537, vol. 239, No. 2, Academic Press, Inc.
Avigad, "An NADH Coupled Assay System for Galactose Oxidase," Analytical Biochemistry, 1978, pp. 470-476, 86, Academic Press, Inc.
Avigad et al., "The D-Galactose Oxidase of Polyporus circinatus," Journal of Biological Chemistry, Sep. 1962, pp. 2736-2743, vol. 237, No. 9, American Society of Biological Chemists, Baltimore, MD, USA.
Barnes, "Maximizing Expression of Eukaryotic Cytochrome P450s in *Escherichia coli*," Methods in Enzymology, Cytochrome P450, Part B, 1996, pp. 3-14, vol. 272, Academic Press, Inc., San Diego, CA, USA.
Baron et al., "Structure and Mechanism of Galactose Oxidase," The Journal of Biological Chemistry, Sep. 23, 1994, pp. 25095-25105, vol. 269, No. 38, American Soc for Biochemistry and Molecular Biology.
Benson et al., "Regulation of Membrane Peptides by the *Pseudomonas* Plasmid alk Regulon," Journal of Bacteriology, Dec. 1979, pp. 754-762, vol. 140, No. 3.
Better et al., "*Escherichia coli* Secretion of an Active Chimeric Antibody Fragment," Science, May 20, 1988, pp. 1041-1043, vol. 240, American Asso for the Advancement of Science, Washington, DC, USA.
Boddupalli et al., "Fatty Acid Monooxygenation by P450BM-3: Product Identification and Proposed Mechanisms for the Sequential Hydroxylation Reactions," Archives of Biochemistry and Biophysics, Jan. 1992, pp. 20-28, vol. 292, No. 1, Academic Press, Inc.
Boddupalli et al., "Fatty Acid Monooxygenation by Cytochrome P-450BM-3," The Journal of Biological Chemistry, 1990, pp. 4233-4239, The American Society for Biochemistry and Molecular Biology.
Borman et al., "Kinetic studies on the reactions of Fusarium galactose oxidase with five different substrates in the presence of dioxygen," Journal of Biological Inorganic Chemistry, 1997, pp. 480-487, Society of Biological Inorganic Chemistry.
Calderhead, D. et al., "Labeling of Glucose Transporters at the Cell Surface in 3T3-L1 Adipocytes," The Journal of Biological Chemistry, Sep. 5, 1988, pp. 12171-12174, vol. 263, No. 25, The American Society for Biochemistry and Molecular Biology.
Calvin, N. et al., "High-Efficiency Transformation of Bacterial Cells by Electroporation," Journal of Bacteriology, Jun. 1988, pp. 2796-2801, vol. 170, No. 6, American Society for Microbiology.
Cameron, A., "Two cradles for the heavy elements," Nature, Jan. 15, 1998, pp. 228-231, vol. 39.
Capdevila, J. et al., "The Highly Stereoselective Oxidation of Polyunsaturated Fatty Acids by Cytochrome P450BM-3," The Journal of Biological Chemistry, Sep. 13, 1996, pp. 22663-22671, vol. 271, No. 37, The American Society for Biochemistry and Molecular Biology, Inc.
Carmichael, A. et al., "Protein engineering of *Bacillus megaterium* CYP102," Eur. J. Biochem., 2001, pp. 3117-3125, vol. 268, FEBS.
Castelli, L. et al., "High-level secretion of correctly processed β-lactamase from *Saccharomyces cerevisiae* using a high-copy-number secretion vector," Gene, 1994, pp. 113-117, vol. 142, Elsevier Science B.V.
Chang, C. et al., "Evolution of a cytokine using DNA family shuffling," Nature Biotechnology, Aug. 1999, pp. 793-797, vol. 17.
Chang, Y. et al., "Homology Modeling, Molecular Dynamics Simulations, and Analysis of CYP119, a P450 Enzyme from Extreme Acidothermophilic Archaeon Sulfolobus solfataricus," Biochemistry, 2000, pp. 2484-2498, vol. 39, No. 10, American Chemical Society.
Chen, H. et al., "Thermal, Catalytic, Regiospecific Functionalization of Alkanes," Science, 2000, vol. 287, pp. 1995-1997.
Chen, K. et al., "Tuning the activity of an enzyme for unusual environments: Sequential random mutagenesis of subtilisin E for catalysis in dimethylformamide," Proc. Natl. Acad. Sci. USA, Jun. 15, 1993, pp. 5618-5622, vol. 90, No. 12.
Cherry, J. et al., "Directed evolution of a fungal peroxidase," Nature Biotechnology, Apr. 1999, pp. 379-384, vol. 17, Nature America Inc., New York, NY, USA.
Christians, F. et al., "Directed evolution of thymidine kinase for AZT phosphorylation using DNA family shuffling," Nature Biotechnology, Mar. 1999, pp. 259-264, vol. 17, Nature America Inc., New York, NY, USA.
Cleland, J. et al., "Cosolvent Assisted Protein Refolding," Biotechnology, Dec. 1990, pp. 1274-1278, vol. 8.
Crameri, A. et al., "Molecular evolution of an arsenate detoxification pathway by DNA shuffling," Nature Biotechnology, May 1997, pp. 436-438, vol. 15, Nature America Inc., New York, NY, USA.
Crameri, A. et al., "Improved Green Fluorescent Protein by Molecular Evolution Using DNA Shuffling," Nature Biotechnology, Mar. 1996, pp. 315-319, vol. 14, Nature America Inc., New York, NY, USA.
Crameri, A. et al., "Construction and evolution of antibody-phage libraries by DNA shuffling," Nature Medicine, Jan. 1996, pp. 100-106, vol. 2, No. 1.

Dahlhoff, W. et al., "L-Glucose or D-gluco-Hexadialdose from D-Glucurono-6,3-lactone by Controlled Reductions," Angew. Chem. Int. Ed. Engl., 1980, pp. 546-547, 19 No. 7, Verlag Chemie, GmbH, Weinheim, Germany.
Danon, A. et al. "Enrichment of Rat Tissue Lipids with Fatty Acids that are Prostaglandin Precursors" Biochimica et Biophysica Acta, 1975, 388: 318-330.
De Bernardez-Clark, E. et al., "Inclusion Bodies and Recovery of Proteins from the Aggregated State," ACS Symposium Series Protein Refolding, 199th Natl Mtg American Chemical Society, Apr. 22-27, 1990, pp. 1-20, American Chemical Society, Washington, DC, USA.
Deacon, S. et al., "Enhanced Fructose Oxidase Activity in a Galactose Oxidase Variant," ChemBioChem: A European Journal of Chemical Biology, 2004, pp. 971-979, 5, Wiley-VCH Verlag GmbH & Co., Weinheim, Germany.
Delagrave, S. et al., "Recursive ensemble mutagenesis," Protein Engineering, Apr. 1993, pp. 327-331, vol. 6, No. 3, Oxford University Press.
Delagrave, S. et al., "Searching Sequence Space to Engineer Proteins: Exponential Ensemble Mutagenesis," Bio/Technology, Dec. 1993, pp. 1548-1552, vol. 11, American Society for Cell Biology, New Orleans, LA, USA.
Dordick, J., "Designing Enzymes for Use in Organic Solvents," Biotechnol. Prog., 1992, pp. 259-267, 8, American Chemical Society and American Institute of Chemical Engineers.
Dower, W. et al., "High efficiency transformation of *E. coli* by high voltage electroporation," Nucleic Acids Research, 1988, pp. 6127-6145, vol. 16, No. 13, IRL Press Limited, Oxford, England.
Farinas, E., et al., "Directed Evolution of a Cytochrome P450 Monooxygenase for Alkane Oxidation," Adv. Synth. Catal., 2001, pp. 601-606, vol. 343, No. 6-7.
Fiedler, K., et al., The Role of N-Glycans in the Secretory Pathway, Cell, May 5, 1995, pp. 309-312, vol. 81, Cell Press.
Fisher, M., et al., "Positional Specificity of Rabbit CYP4B1 for ω-Hydroxylation of Short-Medium Chain Fatty Acids and Hydrocarbons," Biochemical and Biophysical Research Communications, 1998, pp. 352-355, vol. 248, No. RC988842.
You, L., et al., "Directed Evolution of Subtilisin E in *Bacillus subtilis* to Enhance Total Activity in Aqueous Dimethylformamide," Protein Engineering, 1996, pp. 77-83, vol. 9, Oxford University Press.
Zhang, J., et al., "Directed Evolution of a Fucosidase from a Galactosidase by DNA Shuffling and Screening," Proc. Natl. Acad. Sci. USA, Apr. 1997, pp. 4504-4509, vol. 94.
Zhang, T., et al., "Circular Permutation of T4 Lysozyme," Biochemistry, 1993, pp. 12311-12318, vol. 32, No. 46, American Chemical Society.
Zhao, H., et al., "Directed Evolution Converts Subtilisin E into a Functional Equivalent of Thermitase," Protein Engineering, 1999, pp. 47-53, vol. 12, No. 1, Oxford University Press.
Zhao, H. et al., "Methods for Optimizing Industrial Enzymes by Directed Evolution", Manual of Industrial Microbiology and Biotechnology, 2nd Edition, 1999, pp. 597-604.
Zhao, H., et al., "Molecular Evolution by Staggered Extension Process (StEP) In Vitro Recombination," Nature Biotechnology, Mar. 1998, pp. 258-261, vol. 16.
Zhao, H., et al., "Optimization of DNA Shuffling for High Fidelity Recombination," Nucleic Acids Research, 1997, pp. 1307-1308, vol. 25, No. 6, Oxford University Press.
Zimmer, T., et al., "The CYP52 Multigene Family of *Candida maltosa* Encodes Functionally Diverse n-Alkane-Inducible Cytochromes P450," Biochemical and Biophysical Research Communications, 1996, pp. 784-789, vol. 224, No. 3, Academic Press, Inc.
Li, Huiying et al., "The Structure of the cytochrome p450BM-3 haem domain complexed with the fatty acid substrate, palmitoleic acid," Nature Structural Biology, 1997, pp. 140-146.
Martin, I. et al., "Detection of honey adulteration with beet sugar using stable isotope methodology," Food Chemistry, 1998, pp. 281-286, vol. 61, No. 3, Elsevier Science Ltd.
Schwaneberg, U., et al., "P450 Monooxygenase in Biotechnology—Single-Step, Large-Scale Purification Method for Cytochrome P450 BM-3 by Anion-Exchange Chromatography," Journal of Chromatography, 1999, pp. 149-159, vol. 848, Elsevier Science B.V.
Tressel, P., et al., "Galactose Oxidase from Dactylium dendroides," Methods in Enzymology, 1982, pp. 163-171, vol. 89, Academic Press.
Bradford, "A Rapid and Sensitive Method for the Quantitation of Microgram Quantities of Protein Utilizing the Principle of Protein-Dye Binding," Analytical Biochemistry, pp. 248-254, 1976.
McPherson, M. et al., "Galactose oxidase of Dactylium dendroides. Gene cloning and sequence analysis," Chemical Abstract Service, XP-002298547, Database accession No. M86819, 1992.
Welinder, K., "Supplement to Amino Acid Sequence Studies of Horseradish Peroxidase," pp. 495-502, 1979.
XP-002298548, "Protein Sequence," Database accession No. 355884-87-6, 2004.
Fox, B., et al., "Methane Monooxygenase from Methylosinus trichosporium OB3b," Methods in Enzymology, 1990, pp. 191-202, vol. 188, Academic Press, Inc.
Fox, B., et al., "Methane Monooxygenase from Methylosinus trichosporium OB3b Purification and Properties of a Three-Component System with High Specific Activity from a Type II Methanotroph," The Journal of Biological Chemistry, Jun. 15, 1989, pp. 10023-10033, vol. 264, No. 17, The American Society for Biochemistry and Molecular Biology, Inc.
Fruetel, J., et al., "Relationship of Active Site Topology to Substrate Specificity for Cytochrome P450terp (CYP108)," The Journal of Biological Chemistry, Nov. 18, 1994, pp. 28815-28821, vol. 269, No. 46, The American Society for Biochemistry and Molecular Biology, Inc.
Gahmberg C., et al., "Nonmetabolic Radiolabeling and Taggin of Glycoconjugates," Methods in Enzymology, 1994, pp. 32-44, vol. 230, Academic Press, Inc.
Gazaryan, I. G., "Heterologous Expressions of Heme Containing Peroxidases," Plant Peroxidase Newsletter, Sep. 1994, pp. 11-13, No. 4, LABPV Newsletters.
Gietz, R., et al., "Studies on the Transformation of Intact Yeast Cells by the LiAc/SS-DNA/PEG Procedure," Yeast, Apr. 15, 1995, pp. 355-360, vol. 11, No. 4, John Wiley & Sons Ltd.
Gillam, E., et al., "Expression of Cytochrome P450 2D6 in *Escherichia coli*, Purification, and Spectral and Catalytic Characterization," Archives of Biochemistry and Biophysics, Jun. 1, 1995, pp. 540-550, vol. 319, No. 2, Academic Press, Inc.
Giver, L., et al., "Combinatorial Protein Design by In Vitro Recombination," Current Opinion in Chemical Biology, 1998, pp. 335-338, vol. 2, Current Biology Ltd.
Giver, L., et al., "Directed Evolution of a Thermostable Esterase," Proc. Natl. Acad. Sci. USA, Oct. 1998, pp. 12809-12813, vol. 95.
Goldman, E., et al., "An Algorithmically Optimized Combinatorial Library Screened by Digital Imaging Spectroscopy," Biotechnology, Dec. 1992, pp. 1557-1561, vol. 10.
Graham-Lorence, S., et al., "An Active Site Substitution, F87V, Converts Cytochrome P450 BM-3 into a Regio- and Stereoselective (14S,15R)-Arachidonic Acid Epoxygenase," The Journal of Biological Chemistry, Jan. 10, 1997, pp. 1127-1135, vol. 272, No. 2, The American Society for Biochemistry and Molecular Biology, Inc.
Gram, H., et al., "In Vitro Selection and Affinity Maturation of Antibodies from a Naive Combinatorial Immunoglobulin Library," Proc. Natl. Acad. Sci. USA, Apr. 1992, pp. 3576-3580, vol. 89.
Green, J., et al., "Substrate Specificity of Soluble Methane Monooxygenase Mechanistic Implications," The Journal of Biological Chemistry, Oct. 25, 1989, pp. 17698-17703, vol. 264, No. 30, The American Society for Biochemistry and Molecular Biology, Inc.
Griebenow, K., et al., Lyophilization-Induced Reversible Changes in the Secondary Structure of Proteins, Proc. Natl. Acad. Sci. USA, Nov. 1995, pp. 10969-10976, vol. 92.
Groves, John et al., "Models and Mechanisms of Cytochrome P450 Action," Cytochrome P450: Structure, Mechanisms, and Biochemistry, 2nd Edition, New York, 1995, pp. 3-48.
Guengerich, F., et al., "Purification of Functional Recombinant P450s from Bacteria," Methods in Enzymology, 1996, pp. 35-44, vol. 272, Academic Press, Inc.
Güssow, D., et al., "Direct Clone Characterization from Plaques and Colonies by the Polymerase Chain Reaction," Nucleic Acids Research, 1989, p. 4000, vol. 17, No. 10, IRL Press.

Haines, Donovan C. et al., "Pivotal Role of Water in the Mechanism of P450BM-3," Biochemistry, 2001, 40, pp. 13456-13465.
Hamilton, G.A., et al., "Galactose Oxidase: The Complexities of a Simple Enzyme," Oxidases and Related Redox Systems, 1973, pp. 103-124, vol. 1, University Park Press.
Hamilton, G.A., et al., "Trivalent Copper, Superoxide, and Galactose Oxidase," Journal of the American Chemical Society, Mar. 15, 1978, pp. 1899-1912, vol. 100, No. 6, American Chemical Society.
Hartmann, Martin et al., "Selective Oxidations of Linear Alkanes with Molecular Oxygen on Molecular Sieve Catalysts—A Breakthrough?," Agnew. Chem. Int. Ed. 2000, pp. 888-890, vol. 39, No. 5.
Haschke, R., et al., "Calcium-Related Properties of Horseradish Peroxidase," Biochemical and Biophysical Research Communications, Feb. 28, 1978, pp. 1039-1042, vol. 80, No. 4, Academic Press, Inc.
Helenius, A., "How N-linked Oligosaccharides Affect Glycoprotein Folding in the Endoplasmic Reticulum," Molecular Biology of the Cell, Mar. 1994, pp. 253-265, vol. 5, No. 3, The American Society for Cell Biology.
Hermes, J., et al., "Searching Sequence Space by Definably Random Mutagenesis: Improving the Catalytic Potency of an Enzyme," Proc. Natl. Acad. Sci. USA, Jan. 1990, pp. 696-700, vol. 87.
Ito, N. et al., "X-Ray Crystallographic Studies of Cofactors in Galactose Oxidase," Methods in Enzymology, Redox-Active Amino Acids in Biology, 1995, pp. 235-262, vol. 258, Academic Press, Inc.
Ito, N. et al., "Crystal Structure of a Free Radical Enzyme, Galactose Oxidase," Journal of Molecular Biology, 1994, pp. 794-814, vol. 238, No. 5, Academic Press Limited.
Ito, N. et al., "Novel thioether bond revealed by a 1.7 Å crystal structure of galactose oxidase," Nature, Mar. 7, 1991, pp. 87-90.
Joo, H. et al., "Laboratory evolution of peroxide-mediated cytochrome P450 hydroxylation," Nature, Jun 17, 1999, pp. 670-673, vol. 399.
Joo, Hyun et al., "A high-throughput digital imaging screen for the discovery and directed evolution of oxygenases." Chemistry and Biology, 1999, pp. 699-706.
Khoslat, C. et al., "Expression of Intracellular Hemoglobin Improves Protein Synthesis in Oxygen-Limited *Escherichia coli*," Bio/Technology, Sep. 1990, pp. 849-853, American Society for Cell Biology, New Orleans, LA, USA.
Kiba, N. et al., "A post-column co-immobilized galactose oxidase/peroxidase reactor for fluorometric detection of saccharides in a liquid chromatographic system," Journal of Chromatography, 1989, pp. 183-187, vol. 463, Elsevier Science Publishes B.V., Amsterdam, The Netherlands.
Kim, J. et al., "Use of 4-(Nitrobenzyl)Pyridine (4-NBP) to Test Mutagenic Potential of Slow-Reacting Epoxides, Their Corresponding Olefins, and Other Alkylating Agents," Bull. Environ. Contam. Toxicol., 1992, pp. 879-885, vol. 49, Springer-Verlag New York Inc.
Klibanov, A. et al., "Stereospecific Oxidation of Aliphatic Alcohols Catalyzed by Galactose Oxidase," Biochemical and Biophysical Research Communications, 1982, pp. 804-808, vol. 108, No. 2, Academic Press, Inc.
Knappik, A. et al., "Engineered turns of a recombinant antibody improve its in vivo folding," Protein Engineering, Jan. 1995, pp. 81-89, vol. 8, No. 1, Oxford University Press.
Koroleva, O. et al., "Properties of Fusarium graminearum Galactose Oxidase," 1984, pp. 500-509, Plenum Publishing Corporation.
Kosman, D., "Chapter 1 Galactose Oxidase," in Lontie, R., Eds., Copper Proteins and Copper Enzymes vol. II, pp. 1-26, CRC Press, Inc., Boca Raton, FL, USA, 1984.
Koster, R. et al., "Organoboron Monosaccharides; XII1. Quantitative Preparation of D-gluco-Hexodialdose from Sodium D-Glucuronate or D-Glucuronic acid," Synthesis, Aug. 1982, pp. 650-652, No. 8, Georg Thieme Verlag.
Kuchner, O. et al., "Directed evolution of enzyme catalysts," Trends in Biotechnology, Dec. 1997, pp. 523-530, vol. 15, Elsevier Science Ltd.
Kuhn-Velten, W., "Effects of Compatible Solutes on Mammalian Cytochrome P450 Stability," 1997, pp. 132-135, Verlag der Zeitschrift für Naturforschung.
Kvittingen, L. et al., "Use of Salt Hydrates to Buffer Optimal Water Level During Lipase Catalysed Synthesis in Organic Media: A Practical Procedure for Organic Chemists," Tetrahedron, 1992, pp. 2793-2802, vol. 48, No. 13, Pergamon Press Ltd., Great Britain.
Lei, S. et al., "Characterization of the Erwinia carotovora pelB Gene and Its Product Pectate Lyase," Journal of Bacteriology, Sep. 1987, pp. 4379-4383, vol. 169, No. 9, American Society for Microbiology.
Leadbetter, E. R., et al. "Incorporation of Molecular Oxygen in Bacterial Cells Utilizing Hydrocarbons for Growth" Nature, Oct. 31, 1959; vol. 184, pp. 1428-1429.
Leung, D. et al., "A Method for Random Mutagenesis of a Defined DNA Segment Using a Modified Polymerase Chain Reaction," Technique, A Journal of Methods in Cell and Molecular Biology, Aug. 1989, pp. 11-15, vol. 1, No. 1, Saunders Scientific Publications.
Lewis, D., "P450 Substrate Specificity and Metabolism," Cytochrome P450: Structure, Function and Mechanism, Aug. 2001, pp. 115-166, Taylor & Francis Publishers.
Li, Q. et al., "Rational evolution of a medium chain-specific cytochrome P-450 BM-3 variant," Biochimica et Biophysica Acta, 2001, pp. 114-121, 1545, Elsevier Science B.V.
Lis, M. et al., "Galactose Oxidase-Glucan Binding Domain Fusion Proteins as Targeting Inhibitors of Dental Plaque Bacteria," Antimicrobial Agents & Chemotherapy, May 1997, pp. 999-1003, vol. 41, No. 5, American Society for Microbiology.
Liu, C. et al., "Sugar-containing Polyamines Prepared Using Galactose Oxidase Coupled with Chemical Reduction," J. Am. Chem. Soc., Jan. 20, 1999, pp. 466-467, vol. 121, No. 2, American Chemical Society.
Mannino, S. et al., "Simultaneous Determination of Glucose and Galactose in Dairy Products by Two Parallel Amperometric Biosensors," Italian Journal of Food Science, 1999, pp. 57-65, vol. 11, No. 1, Chiriotti Editori, s.p.a., Pinerolo, Italy.
Maradufu, A. et al., "A Non-Hydrogen-Bonding Role for the 4-Hydroxyl Group of D-Galactose in its Reaction with D-Galactose Oxidase," Carbohydrate Research, 1974, pp. 93-99, 32, Elsevier Scientific Publishing Company, Amsterdam, The Netherlands.
Maradufu, A. et al., "Stereochemistry of Dehydrogenation by D-Galactose Oxidase," Canadian Journal of Chemistry, Oct. 1971, pp. 3429-3437, vol. 49, No. 19, NCR Research Press, Ottawa, Canada.

A

B

GenBank Accession No:

```
P14779      TIKEMPQPKTFGELKNLPLLNTDKPVQALMKIADELGEIFKFEAPGRVTR  50
D69799      ----IPQPKTFGPLGNLPLIDKDKPTLSLIKLAEEQGPIFQIHTPAGTTI  46
O08336      ----IPQPKTYGPLKNLPHLEKEQLSQSLWRIADELGPIFRFDFPGVSSV  46
CAB66201.1  ------------------------PMQDSLRYARRLGPIFRRRAFGKEFV  26
BAA82526.1  ----IPEPPGYPLIGNLGEFTSNPLS-DLNRLADTYGPIFRLRLGAKAPI  45
AAG27132.1  -LRPIPGPKPLPLLGNLFDFDFDNLTKSLGELGKIHGPIYSITFGASTEI  49
                                        . .    * *:      .

            YLSSQRLIKEACDESRFDKNLSQALKFVRDFAGDGLFTSWTHEKNWKKAH  100
            VVSGHELVKEVCDEERFDKSIEGALEKVRAFSGDGLFTSWTHEPNWRKAH  96
            FVSGHNLVAEVCDEKRFDKNLGKGLQKVREFGGDGLFTSWTHEPNWQKAH  96
            FVWGAALAADLADEARFAKHVGLGVANLRPVAGDGLFTAYNHEPNWQLAH  76
            FVSSNSLINEVCDEKRFKKTLKSVLSQVREGVHDGLFTAFEDEPNWGKAH  95
            MVTSREIAQELCDETRFCKLPGGALDVMKAVVGDGLFTAETSNPKWAIAH  99
             : .  :  : .**. ** *     :  ::    *****:    : :*  **

            NILLPSFSQQAMKGYHAMMVDIAVQLVQKWERLNAD-EHIEVPEDMTRLT  149
            NILMPTFSQRAMKDYHEKMVDIAVQLIQKWARLNPN-EAVDVPGDMTRLT  145
            RILLPSFSQKAMKGYHSMMLDIATQLIQKWSRLNPN-EEIDVADDMTRLT  145
            DVLAPGFSREAMAGYHVMMLDVAARLTGHWDLAEASGRAVDVPGDMTKLT  126
            RILVPAFGPLSIRGMFPEMHDIATQLCMKFARHGPR-TPIDTSDNFTRLA  144
            RIITPLFGAMRIRGMFDDMKDICEQMCLRWARFGPD-EPLNVCDNMTKLT  148
             :: * *.   : . .   * *:. ::  ::    .    ::.  ::*:*:

            LDTIGLCGFNYRFNSFYRDQ--PHPFITSMVRALDEAMNKLQRANPDDPA  197
            LDTIGLCGFNYRFNSYYRET--PHPFINSMVRALDEAMHQMQRLDVQDKL  193
            LDTIGLCGFNYRFNSFYRDS--QHPFITSMLRALKEAMNQSKRLGLQDKM  193
            LETIARTGFGHDFGSFERSR--LHPFVTAMVGTLGYAQRLNTVPAPLAPW  174
            LDTLALCAMDFRFYSYYKEE--LHPFIEAMGDFLTESGNRNRRPPFAPNF  192
            LDTIALCTIDYRFNSFYRENGAAHPFAEAVVDVMTESFDQSNLPDFVNNY  198
            *:*:.    :.. * *: :.    ***  ::    :   :

            YDENK-RQFQEDIKVMNDLVDKIIADRKASG---------EQSD-DLLTHM  237
            MVRTK-RQFRYDIQTMFSLVDSIIAERRANG---------DQDEKDLLARM  234
            MVKTK-LQFQKDIEVMNSLVDRMIAERKANP---------DENIKDLLSLM  234
            LLRDASRRNAADIAHLNRTVDDLVRERRANGGTGGGTGSGSGSGDLLDRM  224
            LYRAANEKFYGDIALMKSVADEVVAARKASP----------SDRKDLLAAM  233
            VRFRAMAKFKRQAAELRRQTEELIAARRQNP----------VDRDDLLNAM  239
                    :   :   .: ::  *: .             .  ***   *

            LNGKDPETGEPLDDENIRYQIITFLIAGHETTSGLLSFALYFLVKNPHVL  287
            LNVEDPETGEKLDDENIRFQIITFLIAGHETTSGLLSFATYFLLKHPDKL  284
            LYAKDPVTGETLDDENIRYQIITFLIAGHETTSGLLSFAIYCLLTHPEKL  284
            LETAHPRTGERLSPQNVRRQVITFLVAGHETTSGALSFALHYLAQHPDVA  274
            LNGVDPQTGEKLSDENITNQLITFLIAGHETTSGTLSFAMYQLLKNPEAY  283
            LSAKDPKTGEGLSPESIVDNLLTFLIAGHETTSSLLSFCFYYLLENPHVL  289
            *    .* *** *. :.:  :::***:*******. ***. : *   :*.
```

FIGURE 20A

```
QKAAEEAARVLVD-PVPSYKQVKQLKYVGMVLNEALRLWPTAPAFSLYAK 336
KKAYEEVDRVLTD-AAPTYKQVLELTYIRMILNESLRLWPTAPAFSLYPK 333
KKAQEEADRVLTD-DTPEYKQIQQLKYIRMVLNETLRLYPTAPAFSLYAK 333
ARARAEVDRVWGDTEAPGYEQVAKLRYVRRVLDESLRLWPTAPGFAREAR 324
SKVQKEVDEVVGR-GPVLVEHLTKLPYISAVLRETLRLNSPITAFGLEAI 332
RRVQQEVDTVVGS-DTITVDHLSSMPYLEAVLRETLRLRDPGPGFYVKPL 338
 :.  *.  *          .:: .: *:  :* *:***  . ..*   .

EDTVLGGEYPLEKGDELMVLIPQLHRDKTIWGDDVEEFRPERFENPSA-- 384
EDTVIGGKFPITTNDRISVLIPQLHRDRDAWGKDAEEFRPERFEHQDQ-- 381
EDTVLGGEYPISKGQPVTVLIPKLHRDQNAWGPDAEDFRPERFEDPSS-- 381
EDTVLGGTHPMRRGAWALVLTGMLHRDPEVWGADAERFDPDRFDAKAVRS 374
DDTFLGGKYLVKKGEIVTALLSRGHVDPVVYGNDADKFIPERMLDDEFAR 382
KDEVVAGKYAVNKDQPLFIVFDSVHRDQSTYGADADEFRPERMLKDGFDK 388
.* .:.* . :  .       :     * *    :* *.: * *:*:

IP---QHAFKPFGNGQRACIGQQFALHEATLVLGMMLKHFDFED-HTNYE 430
VP---HHAYKPFGNGQRACIGMQFALHEATLVLGMILKYFTLID-HENYE 427
IP---HHAYKPFGNGQRACIGMQFALQEATMVLGLVLKHFELIN-HTGYE 427
RA---PHTFKPFGTGARACIGRQFALHEATLVLGLLLRRYELRP-EPGYR 420
LNKEYPNCWKPFGNGKRACIGRPFAWQESLLAMVVLFQNFNFTMTDPNYA 432
LP---PCAWKPFGNGVRACVGRPFAMQQAILAVAMVLHKFDLVK-DESYT 434
          :****.* ***:*  ** ::: :.: :::: : :    . .*

LDIKETLTLKPEGFVVKAKSKKIPLGGIPSPST 463
LDIKQTLTLKPGDFHISVQSR------------ 448
LKIKEALTIKPDDFKITVKPRK----------- 449
LRVTERLTLMPEG-------------------- 433
LEIKQTLTIKPDHFYINA--------------- 450
LKYHVTMTVRPVGFTMKVRLRQ----------- 456
*     :*: *
```

FIGURE 20B

Mutation Locations:
V78: helix B' (S72-G83)
H138: β3-1 (H138-V141)
T175: helix F (P172-Q189)
V178: helix F (P172-Q189)
A184: helix F( P172-Q189)
N186: helix F (P172-Q189)
D217: helix G (A197-S226)
S226: helix G (A197-S226)
H236: helix H (L233-N239)
E252: helix I (D250-K282)
R255: helix I (D250-K282)
A290: helix J (N283-L298)
A295: helix J (N283-L298)
L353: helix β1-3 (G350-L356)
G396: loop connecting helix K' and L

Mutant
BM-3 139-3
V78A
H138Y
T175I
V178I
A184V
H236Q
E252G
R255S
A290V
A295T
L353V

SEQUENCE LISTING

```
<160> NUMBER OF SEQ ID NOS: 42

<210> SEQ ID NO 1
<211> LENGTH: 4957
<212> TYPE: DNA
<213> ORGANISM: Bacillus megaterium
<220> FEATURE:
<221> NAME/KEY: CDS
<222> LOCATION: (1544)..(4690)
<300> PUBLICATION INFORMATION:
<308> DATABASE ACCESSION NUMBER: Genbank/J04832
<309> DATABASE ENTRY DATE: 1996-02-13
<313> RELEVANT RESIDUES IN SEQ ID NO: (1)..(4957)

<400> SEQUENCE: 1

agatctttat gaagacatag ctgcagaaga aaaagcaaga gctacatatc aatggttaat      60

tgatatatca gatgatcccg atttaaacga cagcttacga tttttacgag aaagagagat     120

tgttcactca cagcggttcc gcgaggccgt ggagatttta aaagatgaca gagacaggaa     180
```

-continued

```
gaaaatcttt taactagtaa aaaaacatcc cccttggcga atgcaaacga aaggagggat    240

gttttttgtt gtgactgcgt tgattatgcg ctagaactgc agtgacaaga aacaaccttt    300

aatttccctt caacatcttt ccaaactcgc gtataactgt attcacctcc aatagattca    360

ccggttgcca gtgccccatt taacgctact tttgtaacgg taacggcaag ttcttgaaac    420

agtttaactt cttgttccaa cacttccatg cccgctatat caagactttt tgaacgatga    480

acatttatat cttcttcttt tgacaaccat tgcccaaggt gattcacaaa aataagctca    540

tctgaaagta attcttctaa tagctctatg ttattagaaa gcatggctga gcgaagcatt    600

tcttcgtatt ctataactct tgcttgattc atttttaatc ctcctttacg ccttgtgtaa    660

ctcttttcta tttccacgtt gcttttcctt taaacttctt tcattaataa ttcgtgctaa    720

attatgttaa tagaggggat aagtggacta attttctgta agcactaaat attctgaaat    780

actctgttaa ttacctttaa atggtataaa attagaatga aagaaccttt tctttccact    840

tttctagtta tctttttact attaagatgc agtttttttat acttgtaatt gtagcggaat    900

gaacgttcat tccgtttttg aaaagaggtg ataaagtgga atctactcca acaaaacaaa    960

aagcgatttt ttctgcttcg cttctgctgt ttgcagaaag agggtttgat gcaaccacga   1020

tgccaatgat tgcagagaat gccaaagtag gagcaggaac aatttatcgc tactttaaaa   1080

ataaagaaag ccttgtaaat gaattattcc aacagcacgt aaacgagttt ttacagtgca   1140

ttgaaagcgg tctggcaaac gagagagatg gataccgaga tgggtttcat catatctttg   1200

aaggtatggt gacatttact aaaaaccatc ctcgtgctct tggatttatt aaaactcata   1260

gccaaggaac tttttttaaca gaagagagcc gcttagcata tcaaaagctg gtggaatttg   1320

tttgtacgtt cttcagagaa ggacaaaagc aaggtgtgat tagaaatctt cctgaaaatg   1380

cgctaattgc tattttattt ggaagtttca tggaagtata tgaaatgatt gaaaatgact   1440

acttatcttt aactgatgaa cttcttaccg gtgtagaaga gagtctgtgg gcagcactta   1500

gcagacaatc atgaaactta acaagtgaaa gagggataac atg aca att aaa gaa     1555
                                             Thr Ile Lys Glu
                                             1

atg cct cag cca aaa acg ttt gga gag ctt aaa aat tta ccg tta tta     1603
Met Pro Gln Pro Lys Thr Phe Gly Glu Leu Lys Asn Leu Pro Leu Leu
5                   10                  15                  20

aac aca gat aaa ccg gtt caa gct ttg atg aaa att gcg gat gaa tta     1651
Asn Thr Asp Lys Pro Val Gln Ala Leu Met Lys Ile Ala Asp Glu Leu
                25                  30                  35

gga gaa atc ttt aaa ttc gag gcg cct ggt cgt gta acg cgc tac tta     1699
Gly Glu Ile Phe Lys Phe Glu Ala Pro Gly Arg Val Thr Arg Tyr Leu
            40                  45                  50

tca agt cag cgt cta att aaa gaa gca tgc gat gaa tca cgc ttt gat     1747
Ser Ser Gln Arg Leu Ile Lys Glu Ala Cys Asp Glu Ser Arg Phe Asp
        55                  60                  65

aaa aac tta agt caa gcg ctt aaa ttt gta cgt gat ttt gca gga gac     1795
Lys Asn Leu Ser Gln Ala Leu Lys Phe Val Arg Asp Phe Ala Gly Asp
    70                  75                  80

ggg tta ttt aca agc tgg acg cat gaa aaa aat tgg aaa aaa gcg cat     1843
Gly Leu Phe Thr Ser Trp Thr His Glu Lys Asn Trp Lys Lys Ala His
85                  90                  95                  100

aat atc tta ctt cca agc ttc agt cag cag gca atg aaa ggc tat cat     1891
Asn Ile Leu Leu Pro Ser Phe Ser Gln Gln Ala Met Lys Gly Tyr His
                105                 110                 115

gcg atg atg gtc gat atc gcc gtg cag ctt gtt caa aag tgg gag cgt     1939
Ala Met Met Val Asp Ile Ala Val Gln Leu Val Gln Lys Trp Glu Arg
            120                 125                 130
```

-continued

```
cta aat gca gat gag cat att gaa gta ccg gaa gac atg aca cgt tta      1987
Leu Asn Ala Asp Glu His Ile Glu Val Pro Glu Asp Met Thr Arg Leu
        135                 140                 145

acg ctt gat aca att ggt ctt tgc ggc ttt aac tat cgc ttt aac agc      2035
Thr Leu Asp Thr Ile Gly Leu Cys Gly Phe Asn Tyr Arg Phe Asn Ser
    150                 155                 160

ttt tac cga gat cag cct cat cca ttt att aca agt atg gtc cgt gca      2083
Phe Tyr Arg Asp Gln Pro His Pro Phe Ile Thr Ser Met Val Arg Ala
165                 170                 175                 180

ctg gat gaa gca atg aac aag ctg cag cga gca aat cca gac gac cca      2131
Leu Asp Glu Ala Met Asn Lys Leu Gln Arg Ala Asn Pro Asp Asp Pro
                185                 190                 195

gct tat gat gaa aac aag cgc cag ttt caa gaa gat atc aag gtg atg      2179
Ala Tyr Asp Glu Asn Lys Arg Gln Phe Gln Glu Asp Ile Lys Val Met
            200                 205                 210

aac gac cta gta gat aaa att att gca gat cgc aaa gca agc ggt gaa      2227
Asn Asp Leu Val Asp Lys Ile Ile Ala Asp Arg Lys Ala Ser Gly Glu
        215                 220                 225

caa agc gat gat tta tta acg cat atg cta aac gga aaa gat cca gaa      2275
Gln Ser Asp Asp Leu Leu Thr His Met Leu Asn Gly Lys Asp Pro Glu
    230                 235                 240

acg ggt gag ccg ctt gat gac gag aac att cgc tat caa att att aca      2323
Thr Gly Glu Pro Leu Asp Asp Glu Asn Ile Arg Tyr Gln Ile Ile Thr
245                 250                 255                 260

ttc tta att gcg gga cac gaa aca aca agt ggt ctt tta tca ttt gcg      2371
Phe Leu Ile Ala Gly His Glu Thr Thr Ser Gly Leu Leu Ser Phe Ala
                265                 270                 275

ctg tat ttc tta gtg aaa aat cca cat gta tta caa aaa gca gca gaa      2419
Leu Tyr Phe Leu Val Lys Asn Pro His Val Leu Gln Lys Ala Ala Glu
            280                 285                 290

gaa gca gca cga gtt cta gta gat cct gtt cca agc tac aaa caa gtc      2467
Glu Ala Ala Arg Val Leu Val Asp Pro Val Pro Ser Tyr Lys Gln Val
        295                 300                 305

aaa cag ctt aaa tat gtc ggc atg gtc tta aac gaa gcg ctg cgc tta      2515
Lys Gln Leu Lys Tyr Val Gly Met Val Leu Asn Glu Ala Leu Arg Leu
    310                 315                 320

tgg cca act gct cct gcg ttt tcc cta tat gca aaa gaa gat acg gtg      2563
Trp Pro Thr Ala Pro Ala Phe Ser Leu Tyr Ala Lys Glu Asp Thr Val
325                 330                 335                 340

ctt gga gga gaa tat cct tta gaa aaa ggc gac gaa cta atg gtt ctg      2611
Leu Gly Gly Glu Tyr Pro Leu Glu Lys Gly Asp Glu Leu Met Val Leu
                345                 350                 355

att cct cag ctt cac cgt gat aaa aca att tgg gga gac gat gtg gaa      2659
Ile Pro Gln Leu His Arg Asp Lys Thr Ile Trp Gly Asp Asp Val Glu
            360                 365                 370

gag ttc cgt cca gag cgt ttt gaa aat cca agt gcg att ccg cag cat      2707
Glu Phe Arg Pro Glu Arg Phe Glu Asn Pro Ser Ala Ile Pro Gln His
        375                 380                 385

gcg ttt aaa ccg ttt gga aac ggt cag cgt gcg tgt atc ggt cag cag      2755
Ala Phe Lys Pro Phe Gly Asn Gly Gln Arg Ala Cys Ile Gly Gln Gln
    390                 395                 400

ttc gct ctt cat gaa gca acg ctg gta ctt ggt atg atg cta aaa cac      2803
Phe Ala Leu His Glu Ala Thr Leu Val Leu Gly Met Met Leu Lys His
405                 410                 415                 420

ttt gac ttt gaa gat cat aca aac tac gag ctg gat att aaa gaa act      2851
Phe Asp Phe Glu Asp His Thr Asn Tyr Glu Leu Asp Ile Lys Glu Thr
                425                 430                 435

tta acg tta aaa cct gaa ggc ttt gtg gta aaa gca aaa tcg aaa aaa      2899
Leu Thr Leu Lys Pro Glu Gly Phe Val Val Lys Ala Lys Ser Lys Lys
            440                 445                 450
```

-continued

```
att ccg ctt ggc ggt att cct tca cct agc act gaa cag tct gct aaa      2947
Ile Pro Leu Gly Gly Ile Pro Ser Pro Ser Thr Glu Gln Ser Ala Lys
        455                 460                 465

aaa gta cgc aaa aag gca gaa aac gct cat aat acg ccg ctg ctt gtg      2995
Lys Val Arg Lys Lys Ala Glu Asn Ala His Asn Thr Pro Leu Leu Val
    470                 475                 480

cta tac ggt tca aat atg gga aca gct gaa gga acg gcg cgt gat tta      3043
Leu Tyr Gly Ser Asn Met Gly Thr Ala Glu Gly Thr Ala Arg Asp Leu
485                 490                 495                 500

gca gat att gca atg agc aaa gga ttt gca ccg cag gtc gca acg ctt      3091
Ala Asp Ile Ala Met Ser Lys Gly Phe Ala Pro Gln Val Ala Thr Leu
            505                 510                 515

gat tca cac gcc gga aat ctt ccg cgc gaa gga gct gta tta att gta      3139
Asp Ser His Ala Gly Asn Leu Pro Arg Glu Gly Ala Val Leu Ile Val
            520                 525                 530

acg gcg tct tat aac ggt cat ccg cct gat aac gca aag caa ttt gtc      3187
Thr Ala Ser Tyr Asn Gly His Pro Pro Asp Asn Ala Lys Gln Phe Val
        535                 540                 545

gac tgg tta gac caa gcg tct gct gat gaa gta aaa ggc gtt cgc tac      3235
Asp Trp Leu Asp Gln Ala Ser Ala Asp Glu Val Lys Gly Val Arg Tyr
    550                 555                 560

tcc gta ttt gga tgc ggc gat aaa aac tgg gct act acg tat caa aaa      3283
Ser Val Phe Gly Cys Gly Asp Lys Asn Trp Ala Thr Thr Tyr Gln Lys
565                 570                 575                 580

gtg cct gct ttt atc gat gaa acg ctt gcc gct aaa ggg gca gaa aac      3331
Val Pro Ala Phe Ile Asp Glu Thr Leu Ala Ala Lys Gly Ala Glu Asn
            585                 590                 595

atc gct gac cgc ggt gaa gca gat gca agc gac gac ttt gaa ggc aca      3379
Ile Ala Asp Arg Gly Glu Ala Asp Ala Ser Asp Asp Phe Glu Gly Thr
            600                 605                 610

tat gaa gaa tgg cgt gaa cat atg tgg agt gac gta gca gcc tac ttt      3427
Tyr Glu Glu Trp Arg Glu His Met Trp Ser Asp Val Ala Ala Tyr Phe
        615                 620                 625

aac ctc gac att gaa aac agt gaa gat aat aaa tct act ctt tca ctt      3475
Asn Leu Asp Ile Glu Asn Ser Glu Asp Asn Lys Ser Thr Leu Ser Leu
    630                 635                 640

caa ttt gtc gac agc gcc gcg gat atg ccg ctt gcg aaa atg cac ggt      3523
Gln Phe Val Asp Ser Ala Ala Asp Met Pro Leu Ala Lys Met His Gly
645                 650                 655                 660

gcg ttt tca acg aac gtc gta gca agc aaa gaa ctt caa cag cca ggc      3571
Ala Phe Ser Thr Asn Val Val Ala Ser Lys Glu Leu Gln Gln Pro Gly
            665                 670                 675

agt gca cga agc acg cga cat ctt gaa att gaa ctt cca aaa gaa gct      3619
Ser Ala Arg Ser Thr Arg His Leu Glu Ile Glu Leu Pro Lys Glu Ala
            680                 685                 690

tct tat caa gaa gga gat cat tta ggt gtt att cct cgc aac tat gaa      3667
Ser Tyr Gln Glu Gly Asp His Leu Gly Val Ile Pro Arg Asn Tyr Glu
        695                 700                 705

gga ata gta aac cgt gta aca gca agg ttc ggc cta gat gca tca cag      3715
Gly Ile Val Asn Arg Val Thr Ala Arg Phe Gly Leu Asp Ala Ser Gln
    710                 715                 720

caa atc cgt ctg gaa gca gaa gaa gaa aaa tta gct cat ttg cca ctc      3763
Gln Ile Arg Leu Glu Ala Glu Glu Glu Lys Leu Ala His Leu Pro Leu
725                 730                 735                 740

gct aaa aca gta tcc gta gaa gag ctt ctg caa tac gtg gag ctt caa      3811
Ala Lys Thr Val Ser Val Glu Glu Leu Leu Gln Tyr Val Glu Leu Gln
            745                 750                 755

gat cct gtt acg cgc acg cag ctt cgc gca atg gct gct aaa acg gtc      3859
Asp Pro Val Thr Arg Thr Gln Leu Arg Ala Met Ala Ala Lys Thr Val
            760                 765                 770
```

-continued

```
tgc ccg ccg cat aaa gta gag ctt gaa gcc ttg ctt gaa aag caa gcc      3907
Cys Pro Pro His Lys Val Glu Leu Glu Ala Leu Leu Glu Lys Gln Ala
        775                 780                 785

tac aaa gaa caa gtg ctg gca aaa cgt tta aca atg ctt gaa ctg ctt      3955
Tyr Lys Glu Gln Val Leu Ala Lys Arg Leu Thr Met Leu Glu Leu Leu
    790                 795                 800

gaa aaa tac ccg gcg tgt gaa atg aaa ttc agc gaa ttt atc gcc ctt      4003
Glu Lys Tyr Pro Ala Cys Glu Met Lys Phe Ser Glu Phe Ile Ala Leu
805                 810                 815                 820

ctg cca agc ata cgc ccg cgc tat tac tcg att tct tca tca cct cgt      4051
Leu Pro Ser Ile Arg Pro Arg Tyr Tyr Ser Ile Ser Ser Ser Pro Arg
                825                 830                 835

gtc gat gaa aaa caa gca agc atc acg gtc agc gtt gtc tca gga gaa      4099
Val Asp Glu Lys Gln Ala Ser Ile Thr Val Ser Val Val Ser Gly Glu
            840                 845                 850

gcg tgg agc gga tat gga gaa tat aaa gga att gcg tcg aac tat ctt      4147
Ala Trp Ser Gly Tyr Gly Glu Tyr Lys Gly Ile Ala Ser Asn Tyr Leu
        855                 860                 865

gcc gag ctg caa gaa gga gat acg att acg tgc ttt att tcc aca ccg      4195
Ala Glu Leu Gln Glu Gly Asp Thr Ile Thr Cys Phe Ile Ser Thr Pro
    870                 875                 880

cag tca gaa ttt acg ctg cca aaa gac cct gaa acg ccg ctt atc atg      4243
Gln Ser Glu Phe Thr Leu Pro Lys Asp Pro Glu Thr Pro Leu Ile Met
885                 890                 895                 900

gtc gga ccg gga aca ggc gtc gcg ccg ttt aga ggc ttt gtg cag gcg      4291
Val Gly Pro Gly Thr Gly Val Ala Pro Phe Arg Gly Phe Val Gln Ala
                905                 910                 915

cgc aaa cag cta aaa gaa caa gga cag tca ctt gga gaa gca cat tta      4339
Arg Lys Gln Leu Lys Glu Gln Gly Gln Ser Leu Gly Glu Ala His Leu
            920                 925                 930

tac ttc ggc tgc cgt tca cct cat gaa gac tat ctg tat caa gaa gag      4387
Tyr Phe Gly Cys Arg Ser Pro His Glu Asp Tyr Leu Tyr Gln Glu Glu
        935                 940                 945

ctt gaa aac gcc caa agc gaa ggc atc att acg ctt cat acc gct ttt      4435
Leu Glu Asn Ala Gln Ser Glu Gly Ile Ile Thr Leu His Thr Ala Phe
    950                 955                 960

tct cgc atg cca aat cag ccg aaa aca tac gtt cag cac gta atg gaa      4483
Ser Arg Met Pro Asn Gln Pro Lys Thr Tyr Val Gln His Val Met Glu
965                 970                 975                 980

caa gac ggc aag aaa ttg att gaa ctt ctt gat caa gga gcg cac ttc      4531
Gln Asp Gly Lys Lys Leu Ile Glu Leu Leu Asp Gln Gly Ala His Phe
                985                 990                 995

tat att tgc gga  gac gga agc caa atg  gca cct gcc gtt gaa  gca      4576
Tyr Ile Cys Gly  Asp Gly Ser Gln Met  Ala Pro Ala Val Glu  Ala
            1000                 1005                 1010

acg ctt atg aaa  agc tat gct gac gtt  cac caa gtg agt gaa  gca      4621
Thr Leu Met Lys  Ser Tyr Ala Asp Val  His Gln Val Ser Glu  Ala
            1015                 1020                 1025

gac gct cgc tta  tgg ctg cag cag cta  gaa gaa aaa ggc cga  tac      4666
Asp Ala Arg Leu  Trp Leu Gln Gln Leu  Glu Glu Lys Gly Arg  Tyr
            1030                 1035                 1040

gca aaa gac gtg  tgg gct ggg taa attaaaaaga ggctaggata aaagtagttt   4720
Ala Lys Asp Val  Trp Ala Gly
            1045

agttggttga aggaagatcc gaacgatgaa tcgttcggat ctttttattg gtagagtaaa   4780

cgtagatttc atctatttag tgacttgtag cggttgattg gagggcaagg tgaagactcc   4840

aatcaaccgc ggtgtcacat gcaagccata cgaaattcat ttctcccatt tattcgtctt   4900

ttgtccccac ttaattttta tagcgcctta acgtttcttc tgcgtgacag cagatct      4957
```

<210> SEQ ID NO 2
<211> LENGTH: 1048
<212> TYPE: PRT
<213> ORGANISM: Bacillus megaterium

<400> SEQUENCE: 2

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380
```

-continued

```
Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815
```

```
Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
    850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
    930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly  Asp Gly Ser Gln Met  Ala Pro Ala
        995                 1000                1005

Val Glu  Ala Thr Leu Met Lys  Ser Tyr Ala Asp Val  His Gln Val
    1010                 1015                 1020

Ser Glu  Ala Asp Ala Arg Leu  Trp Leu Gln Gln Leu  Glu Glu Lys
    1025                 1030                 1035

Gly Arg  Tyr Ala Lys Asp Val  Trp Ala Gly
    1040                 1045


<210> SEQ ID NO 3
<211> LENGTH: 489
<212> TYPE: PRT
<213> ORGANISM: Oryctolagus cuniculus
<300> PUBLICATION INFORMATION:
<308> DATABASE ACCESSION NUMBER: GenBank/P00182
<309> DATABASE ENTRY DATE: 1998-12-15
<313> RELEVANT RESIDUES IN SEQ ID NO: (1)..(489)

<400> SEQUENCE: 3

Met Asp Leu Leu Ile Ile Leu Gly Ile Cys Leu Ser Cys Val Val Leu
1               5                   10                  15

Leu Ser Leu Trp Lys Lys Thr His Gly Lys Gly Lys Leu Pro Pro Gly
            20                  25                  30

Pro Thr Pro Leu Pro Val Val Gly Asn Leu Leu Gln Leu Glu Thr Lys
        35                  40                  45

Asp Ile Asn Lys Ser Leu Ser Met Leu Ala Lys Glu Tyr Gly Ser Ile
    50                  55                  60

Phe Thr Leu Tyr Phe Gly Met Lys Pro Ala Val Val Leu Tyr Gly Tyr
65                  70                  75                  80

Glu Gly Val Ile Glu Ala Leu Ile Asp Arg Gly Glu Glu Phe Ser Gly
                85                  90                  95

Arg Gly Ile Phe Pro Val Phe Asp Arg Val Thr Lys Gly Leu Gly Ile
            100                 105                 110

Val Phe Ser Ser Gly Glu Lys Trp Lys Glu Thr Arg Arg Phe Ser Leu
```

-continued

```
        115                 120                 125

Thr Val Leu Arg Asn Leu Gly Met Gly Lys Lys Thr Ile Glu Glu Arg
    130                 135                 140

Ile Gln Glu Glu Ala Leu Cys Leu Ile Gln Ala Leu Arg Lys Thr Asn
145                 150                 155                 160

Ala Ser Pro Cys Asp Pro Thr Phe Leu Leu Phe Cys Val Pro Cys Asn
                165                 170                 175

Val Ile Cys Ser Val Ile Phe Gln Asn Arg Phe Asp Tyr Asp Asp Glu
            180                 185                 190

Lys Phe Lys Thr Leu Ile Lys Tyr Phe His Glu Asn Phe Glu Leu Leu
        195                 200                 205

Gly Thr Pro Trp Ile Gln Leu Tyr Asn Ile Phe Pro Ile Leu His Tyr
    210                 215                 220

Leu Pro Gly Ser His Arg Gln Leu Phe Lys Asn Ile Asp Gly Gln Ile
225                 230                 235                 240

Lys Phe Ile Leu Glu Lys Val Gln Glu His Gln Glu Ser Leu Asp Ser
                245                 250                 255

Asn Asn Pro Arg Asp Phe Val Asp His Phe Leu Ile Lys Met Glu Lys
            260                 265                 270

Glu Lys His Lys Lys Gln Ser Glu Phe Thr Met Asp Asn Leu Ile Thr
        275                 280                 285

Thr Ile Trp Asp Val Phe Ser Ala Gly Thr Asp Thr Thr Ser Asn Thr
    290                 295                 300

Leu Lys Phe Ala Leu Leu Leu Leu Leu Lys His Pro Glu Ile Thr Ala
305                 310                 315                 320

Lys Val Gln Glu Glu Ile Glu His Val Ile Gly Arg His Arg Ser Pro
                325                 330                 335

Cys Met Gln Asp Arg Thr Arg Met Pro Tyr Thr Asp Ala Val Met His
            340                 345                 350

Glu Ile Gln Arg Tyr Val Asp Leu Val Pro Thr Ser Leu Pro His Ala
        355                 360                 365

Val Thr Gln Asp Ile Glu Phe Asn Gly Tyr Leu Ile Pro Lys Gly Thr
    370                 375                 380

Asp Ile Ile Pro Ser Leu Thr Ser Val Leu Tyr Asp Asp Lys Glu Phe
385                 390                 395                 400

Pro Asn Pro Glu Lys Phe Asp Pro Gly His Phe Leu Asp Glu Ser Gly
                405                 410                 415

Asn Phe Lys Lys Ser Asp Tyr Phe Met Pro Phe Ser Ala Gly Lys Arg
            420                 425                 430

Ala Cys Val Gly Glu Gly Leu Ala Arg Met Glu Leu Phe Leu Leu Leu
        435                 440                 445

Thr Thr Ile Leu Gln His Phe Thr Leu Lys Pro Leu Val Asp Pro Lys
    450                 455                 460

Asp Ile Asp Pro Thr Pro Val Glu Asn Gly Phe Val Ser Val Pro Pro
465                 470                 475                 480

Ser Tyr Glu Leu Cys Phe Val Pro Val
                485
```

<210> SEQ ID NO 4
<211> LENGTH: 490
<212> TYPE: PRT
<213> ORGANISM: Homo sapiens
<300> PUBLICATION INFORMATION:
<308> DATABASE ACCESSION NUMBER: GenBank/P11712
<309> DATABASE ENTRY DATE: 1989-10-01
<313> RELEVANT RESIDUES IN SEQ ID NO: (1)..(490)

-continued

<400> SEQUENCE: 4

```
Met Asp Ser Leu Val Val Leu Val Leu Cys Leu Ser Cys Leu Leu Leu
1               5                   10                  15

Leu Ser Leu Trp Arg Gln Ser Ser Gly Arg Gly Lys Leu Pro Pro Gly
            20                  25                  30

Pro Thr Pro Leu Pro Val Ile Gly Asn Ile Leu Gln Ile Gly Ile Lys
        35                  40                  45

Asp Ile Ser Lys Ser Leu Thr Asn Leu Ser Lys Val Tyr Gly Pro Val
    50                  55                  60

Phe Thr Leu Tyr Phe Gly Leu Lys Pro Ile Val Val Leu His Gly Tyr
65                  70                  75                  80

Glu Ala Val Lys Glu Ala Leu Ile Asp Leu Gly Glu Glu Phe Ser Gly
                85                  90                  95

Arg Gly Ile Phe Pro Leu Ala Glu Arg Ala Asn Arg Gly Phe Gly Ile
            100                 105                 110

Val Phe Ser Asn Gly Lys Lys Trp Lys Glu Ile Arg Arg Phe Ser Leu
        115                 120                 125

Met Thr Leu Arg Asn Phe Gly Met Gly Lys Arg Ser Ile Glu Asp Arg
    130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
            180                 185                 190

Gln Phe Leu Asn Leu Met Glu Lys Leu Asn Glu Asn Ile Lys Ile Leu
        195                 200                 205

Ser Ser Pro Trp Ile Gln Ile Cys Asn Asn Phe Ser Pro Ile Ile Asp
    210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Met Asp
                245                 250                 255

Met Asn Asn Pro Gln Asp Phe Ile Asp Cys Phe Leu Met Lys Met Glu
            260                 265                 270

Lys Glu Lys His Asn Gln Pro Ser Glu Phe Thr Ile Glu Ser Leu Glu
        275                 280                 285

Asn Thr Ala Val Asp Leu Phe Gly Ala Gly Thr Glu Thr Thr Ser Thr
    290                 295                 300

Thr Leu Arg Tyr Ala Leu Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Ser His Met Pro Tyr Thr Asp Ala Val Val
            340                 345                 350

His Glu Val Gln Arg Tyr Ile Asp Leu Leu Pro Thr Ser Leu Pro His
        355                 360                 365

Ala Val Thr Cys Asp Ile Lys Phe Arg Asn Tyr Leu Ile Pro Lys Gly
    370                 375                 380

Thr Thr Ile Leu Ile Ser Leu Thr Ser Val Leu His Asp Asn Lys Glu
385                 390                 395                 400

Phe Pro Asn Pro Glu Met Phe Asp Pro His His Phe Leu Asp Glu Gly
                405                 410                 415
```

```
Gly Asn Phe Lys Lys Ser Lys Tyr Phe Met Pro Phe Ser Ala Gly Lys
            420                 425                 430

Arg Ile Cys Val Gly Glu Ala Leu Ala Gly Met Glu Leu Phe Leu Phe
        435                 440                 445

Leu Thr Ser Ile Leu Gln Asn Phe Asn Leu Lys Ser Leu Val Asp Pro
    450                 455                 460

Lys Asn Leu Asp Thr Thr Pro Val Val Asn Gly Phe Ala Ser Val Pro
465                 470                 475                 480

Pro Phe Tyr Gln Leu Cys Phe Ile Pro Val
                485                 490


<210> SEQ ID NO 5
<211> LENGTH: 504
<212> TYPE: PRT
<213> ORGANISM: Rattus norvegicus
<300> PUBLICATION INFORMATION:
<308> DATABASE ACCESSION NUMBER: GenBank/P10633
<309> DATABASE ENTRY DATE: 1989-07-01
<313> RELEVANT RESIDUES IN SEQ ID NO: (1)..(504)

<400> SEQUENCE: 5

Met Glu Leu Leu Asn Gly Thr Gly Leu Trp Ser Met Ala Ile Phe Thr
1               5                   10                  15

Val Ile Phe Ile Leu Leu Val Asp Leu Met His Arg Arg His Arg Trp
            20                  25                  30

Thr Ser Arg Tyr Pro Pro Gly Pro Val Pro Trp Pro Val Leu Gly Asn
        35                  40                  45

Leu Leu Gln Val Asp Leu Ser Asn Met Pro Tyr Ser Leu Tyr Lys Leu
    50                  55                  60

Gln His Arg Tyr Gly Asp Val Phe Ser Leu Gln Lys Gly Trp Lys Pro
65                  70                  75                  80

Met Val Ile Val Asn Arg Leu Lys Ala Val Gln Glu Val Leu Val Thr
                85                  90                  95

His Gly Glu Asp Thr Ala Asp Arg Pro Pro Val Pro Ile Phe Lys Cys
            100                 105                 110

Leu Gly Val Lys Pro Arg Ser Gln Gly Val Ile Leu Ala Ser Tyr Gly
        115                 120                 125

Pro Glu Trp Arg Glu Gln Arg Arg Phe Ser Val Ser Thr Leu Arg Thr
    130                 135                 140

Phe Gly Met Gly Lys Lys Ser Leu Glu Glu Trp Val Thr Lys Glu Ala
145                 150                 155                 160

Gly His Leu Cys Asp Ala Phe Thr Ala Gln Ala Gly Gln Ser Ile Asn
                165                 170                 175

Pro Lys Ala Met Leu Asn Lys Ala Leu Cys Asn Val Ile Ala Ser Leu
            180                 185                 190

Ile Phe Ala Arg Arg Phe Glu Tyr Glu Asp Pro Tyr Leu Ile Arg Met
        195                 200                 205

Val Lys Leu Val Glu Glu Ser Leu Thr Glu Val Ser Gly Phe Ile Pro
    210                 215                 220

Glu Val Leu Asn Thr Phe Pro Ala Leu Leu Arg Ile Pro Gly Leu Ala
225                 230                 235                 240

Asp Lys Val Phe Gln Gly Gln Lys Thr Phe Met Ala Leu Leu Asp Asn
                245                 250                 255

Leu Leu Ala Glu Asn Arg Thr Thr Trp Asp Pro Ala Gln Pro Pro Arg
            260                 265                 270

Asn Leu Thr Asp Ala Phe Leu Ala Glu Val Glu Lys Ala Lys Gly Asn
```

275 280 285

Pro Glu Ser Ser Phe Asn Asp Glu Asn Leu Arg Met Val Val Val Asp
290 295 300

Leu Phe Thr Ala Gly Met Val Thr Thr Ala Thr Thr Leu Thr Trp Ala
305 310 315 320

Leu Leu Leu Met Ile Leu Tyr Pro Asp Val Gln Arg Arg Val Gln Gln
325 330 335

Glu Ile Asp Glu Val Ile Gly Gln Val Arg Cys Pro Glu Met Thr Asp
340 345 350

Gln Ala His Met Pro Tyr Thr Asn Ala Val Ile His Glu Val Gln Arg
355 360 365

Phe Gly Asp Ile Ala Pro Leu Asn Leu Pro Arg Phe Thr Ser Cys Asp
370 375 380

Ile Glu Val Gln Asp Phe Val Ile Pro Lys Gly Thr Thr Leu Ile Ile
385 390 395 400

Asn Leu Ser Ser Val Leu Lys Asp Glu Thr Val Trp Glu Lys Pro His
405 410 415

Arg Phe His Pro Glu His Phe Leu Asp Ala Gln Gly Asn Phe Val Lys
420 425 430

His Glu Ala Phe Met Pro Phe Ser Ala Gly Arg Arg Ala Cys Leu Gly
435 440 445

Glu Pro Leu Ala Arg Met Glu Leu Phe Leu Phe Phe Thr Cys Leu Leu
450 455 460

Gln Arg Phe Ser Phe Ser Val Pro Val Gly Gln Pro Arg Pro Ser Thr
465 470 475 480

His Gly Phe Phe Ala Phe Pro Val Ala Pro Leu Pro Tyr Gln Leu Cys
485 490 495

Ala Val Val Arg Glu Gln Gly Leu
500

<210> SEQ ID NO 6
<211> LENGTH: 428
<212> TYPE: PRT
<213> ORGANISM: Pseudomonas sp.
<300> PUBLICATION INFORMATION:
<308> DATABASE ACCESSION NUMBER: GenBank/P33006
<309> DATABASE ENTRY DATE: 1993-10-01
<313> RELEVANT RESIDUES IN SEQ ID NO: (1)..(428)

<400> SEQUENCE: 6

Met Asp Ala Arg Ala Thr Ile Pro Glu His Ile Ala Arg Thr Val Ile
1 5 10 15

Leu Pro Gln Gly Tyr Ala Asp Asp Glu Val Ile Tyr Pro Ala Phe Lys
20 25 30

Trp Leu Arg Asp Glu Gln Pro Leu Ala Met Ala His Ile Glu Gly Tyr
35 40 45

Asp Pro Met Trp Ile Ala Thr Lys His Ala Asp Val Met Gln Ile Gly
50 55 60

Lys Gln Pro Gly Leu Phe Ser Asn Ala Glu Gly Ser Glu Ile Leu Tyr
65 70 75 80

Asp Gln Asn Asn Glu Ala Phe Met Arg Ser Ile Ser Gly Gly Cys Pro
85 90 95

His Val Ile Asp Ser Leu Thr Ser Met Asp Pro Pro Thr His Thr Ala
100 105 110

Tyr Arg Gly Leu Thr Leu Asn Trp Phe Gln Pro Ala Ser Ile Arg Lys
115 120 125

```
Leu Glu Glu Asn Ile Arg Arg Ile Ala Gln Ala Ser Val Gln Arg Leu
    130                 135                 140

Leu Asp Phe Asp Gly Glu Cys Asp Phe Met Thr Asp Cys Ala Leu Tyr
145                 150                 155                 160

Tyr Pro Leu His Val Val Met Thr Ala Leu Gly Val Pro Glu Asp Asp
                165                 170                 175

Glu Pro Leu Met Leu Lys Leu Thr Gln Asp Phe Phe Gly Val His Glu
            180                 185                 190

Pro Asp Glu Gln Ala Val Ala Ala Pro Arg Gln Ser Ala Asp Glu Ala
        195                 200                 205

Ala Arg Arg Phe His Glu Thr Ile Ala Thr Phe Tyr Asp Tyr Phe Asn
    210                 215                 220

Gly Phe Thr Val Asp Arg Arg Ser Cys Pro Lys Asp Asp Val Met Ser
225                 230                 235                 240

Leu Leu Ala Asn Ser Lys Leu Asp Gly Asn Tyr Ile Asp Asp Lys Tyr
                245                 250                 255

Ile Asn Ala Tyr Tyr Val Ala Ile Ala Thr Ala Gly His Asp Thr Thr
            260                 265                 270

Ser Ser Ser Ser Gly Gly Ala Ile Ile Gly Leu Ser Arg Asn Pro Glu
        275                 280                 285

Gln Leu Ala Leu Ala Lys Ser Asp Pro Ala Leu Ile Pro Arg Leu Val
    290                 295                 300

Asp Glu Ala Val Arg Trp Thr Ala Pro Val Lys Ser Phe Met Arg Thr
305                 310                 315                 320

Ala Leu Ala Asp Thr Glu Val Arg Gly Gln Asn Ile Lys Arg Gly Asp
                325                 330                 335

Arg Ile Met Leu Ser Tyr Pro Ser Ala Asn Arg Asp Glu Glu Val Phe
            340                 345                 350

Ser Asn Pro Asp Glu Phe Asp Ile Thr Arg Phe Pro Asn Arg His Leu
        355                 360                 365

Gly Phe Gly Trp Gly Ala His Met Cys Leu Gly Gln His Leu Ala Lys
    370                 375                 380

Leu Glu Met Lys Ile Phe Phe Glu Glu Leu Leu Pro Lys Leu Lys Ser
385                 390                 395                 400

Val Glu Leu Ser Gly Pro Pro Arg Leu Val Ala Thr Asn Phe Val Gly
                405                 410                 415

Gly Pro Lys Asn Val Pro Ile Arg Phe Thr Lys Ala
            420                 425


<210> SEQ ID NO 7
<211> LENGTH: 51
<212> TYPE: DNA
<213> ORGANISM: Artificial Sequence
<220> FEATURE:
<223> OTHER INFORMATION: oligonucleotide

<400> SEQUENCE: 7

cgcggatcca tcgatgctta ggaggtcata tgacaattaa agaaatgcct c              51


<210> SEQ ID NO 8
<211> LENGTH: 51
<212> TYPE: DNA
<213> ORGANISM: Artificial Sequence
<220> FEATURE:
<223> OTHER INFORMATION: oligonucleotide

<400> SEQUENCE: 8

ccggaattct taatgatgat gatgatgatg cccagcccac acgtcttttg c              51
```

<210> SEQ ID NO 9
<211> LENGTH: 32
<212> TYPE: DNA
<213> ORGANISM: Artificial Sequence
<220> FEATURE:
<223> OTHER INFORMATION: PCR primer

<400> SEQUENCE: 9
catacaaact acgagctcga tattaaagaa ac 32

<210> SEQ ID NO 10
<211> LENGTH: 32
<212> TYPE: DNA
<213> ORGANISM: Artificial Sequence
<220> FEATURE:
<223> OTHER INFORMATION: PCR primer

<400> SEQUENCE: 10
gtttctttaa tatcgagctc gtagtttgta tg 32

<210> SEQ ID NO 11
<211> LENGTH: 32
<212> TYPE: DNA
<213> ORGANISM: Artificial Sequence
<220> FEATURE:
<223> OTHER INFORMATION: PCR primer

<400> SEQUENCE: 11
acaggatcca tcgatgctta ggaggtcata tg 32

<210> SEQ ID NO 12
<211> LENGTH: 19
<212> TYPE: DNA
<213> ORGANISM: Artificial Sequence
<220> FEATURE:
<223> OTHER INFORMATION: PCR primer

<400> SEQUENCE: 12
gtgaaggaat accgccaag 19

<210> SEQ ID NO 13
<211> LENGTH: 30
<212> TYPE: DNA
<213> ORGANISM: Artificial Sequence
<220> FEATURE:
<223> OTHER INFORMATION: PCR primer pTBamHd

<400> SEQUENCE: 13
gaaccggatc catgacaatt aaagaaatgc 30

<210> SEQ ID NO 14
<211> LENGTH: 26
<212> TYPE: DNA
<213> ORGANISM: Artificial Sequence
<220> FEATURE:
<223> OTHER INFORMATION: PCR primer Rev3250

<400> SEQUENCE: 14
ctattctcac tccgctgaaa ctgttg 26

<210> SEQ ID NO 15
<211> LENGTH: 32
<212> TYPE: DNA
<213> ORGANISM: Artificial Sequence
<220> FEATURE:
<223> OTHER INFORMATION: PCR primer pT235 F
<220> FEATURE:
<221> NAME/KEY: misc_feature
<222> LOCATION: (15)..(17)
<223> OTHER INFORMATION: n is a, c, g, or t

<400> SEQUENCE: 15
gcgatgattt attannncat atgctaaacg ga 32

<210> SEQ ID NO 16
<211> LENGTH: 32
<212> TYPE: DNA
<213> ORGANISM: Artificial Sequence
<220> FEATURE:
<223> OTHER INFORMATION: PCR primer pT235_R
<220> FEATURE:
<221> NAME/KEY: misc_feature
<222> LOCATION: (16)..(18)
<223> OTHER INFORMATION: n is a, c, g, or t

<400> SEQUENCE: 16
tccgtttagc atatgnnnta ataaatcatc gc 32

<210> SEQ ID NO 17
<211> LENGTH: 38
<212> TYPE: DNA
<213> ORGANISM: Artificial Sequence
<220> FEATURE:
<223> OTHER INFORMATION: PCR primer pT471_F
<220> FEATURE:
<221> NAME/KEY: misc_feature
<222> LOCATION: (19)..(21)
<223> OTHER INFORMATION: n is a, c, g, or t

<400> SEQUENCE: 17
cagtctgcta aaaaagtann naaaaaggca gaaaacgc 38

<210> SEQ ID NO 18
<211> LENGTH: 38
<212> TYPE: DNA
<213> ORGANISM: Artificial Sequence
<220> FEATURE:
<223> OTHER INFORMATION: PCR primer pT471_R
<220> FEATURE:
<221> NAME/KEY: misc_feature
<222> LOCATION: (18)..(20)
<223> OTHER INFORMATION: n is a, c, g, or t

<400> SEQUENCE: 18
gcgttttctg ccttttttnnn tactttttta gcagactg 38

<210> SEQ ID NO 19
<211> LENGTH: 33
<212> TYPE: DNA
<213> ORGANISM: Artificial Sequence
<220> FEATURE:
<223> OTHER INFORMATION: PCR primer pT1024_F
<220> FEATURE:
<221> NAME/KEY: misc_feature
<222> LOCATION: (16)..(18)
<223> OTHER INFORMATION: n is a, c, g, or t

<400> SEQUENCE: 19
gacgttcacc aagtgnnnga agcagacgct cgc 33

<210> SEQ ID NO 20
<211> LENGTH: 33
<212> TYPE: DNA
<213> ORGANISM: Artificial Sequence
<220> FEATURE:
<223> OTHER INFORMATION: PCR primer pT3074_R
<220> FEATURE:
<221> NAME/KEY: misc_feature
<222> LOCATION: (16)..(18)
<223> OTHER INFORMATION: n is a, c, g, or t

<400> SEQUENCE: 20
gcgagcgtct gcttcnnnca cttggtgaac gtc 33

<210> SEQ ID NO 21
<211> LENGTH: 30
<212> TYPE: DNA
<213> ORGANISM: Artificial Sequence
<220> FEATURE:
<223> OTHER INFORMATION: PCR primer A87F1

<400> SEQUENCE: 21
gcaggagacg ggttatttac aagctggacg 30

<210> SEQ ID NO 22
<211> LENGTH: 30
<212> TYPE: DNA
<213> ORGANISM: Artificial Sequence
<220> FEATURE:
<223> OTHER INFORMATION: PCR primer A87F2

<400> SEQUENCE: 22
cgtccagctt gtaaataacc cgtctcctgc 30

<210> SEQ ID NO 23
<211> LENGTH: 29
<212> TYPE: DNA
<213> ORGANISM: Artificial Sequence
<220> FEATURE:
<223> OTHER INFORMATION: PCR primer F87Gly1

<400> SEQUENCE: 23
gcaggagacg ggttaggtca agctggacg 29

<210> SEQ ID NO 24
<211> LENGTH: 30
<212> TYPE: DNA
<213> ORGANISM: Artificial Sequence
<220> FEATURE:
<223> OTHER INFORMATION: PCR primer F87Gly2

<400> SEQUENCE: 24
cgtccagctt gtacctaacc cgtctcctgc 30

<210> SEQ ID NO 25
<211> LENGTH: 30
<212> TYPE: DNA
<213> ORGANISM: Artificial Sequence
<220> FEATURE:
<223> OTHER INFORMATION: PCR primer F87Trp1

<400> SEQUENCE: 25
gcaggagacg ggttatggac aagctggacg 30

<210> SEQ ID NO 26
<211> LENGTH: 30
<212> TYPE: DNA
<213> ORGANISM: Artificial Sequence
<220> FEATURE:
<223> OTHER INFORMATION: PCR primer F87Trp2

<400> SEQUENCE: 26
cgtccagctt gtccataacc cgtctcctgc 30

<210> SEQ ID NO 27
<211> LENGTH: 30
<212> TYPE: DNA
<213> ORGANISM: Artificial Sequence
<220> FEATURE:
<223> OTHER INFORMATION: PCR primer F87His1

<400> SEQUENCE: 27
gcaggagacg ggttacacac aagctggacg 30

<210> SEQ ID NO 28
<211> LENGTH: 31
<212> TYPE: DNA
<213> ORGANISM: Artificial Sequence
<220> FEATURE:
<223> OTHER INFORMATION: PCR primer F87His2

<400> SEQUENCE: 28
cgtccagctt gtgtgtaacc cgtcctcctg c 31

<210> SEQ ID NO 29
<211> LENGTH: 30
<212> TYPE: DNA
<213> ORGANISM: Artificial Sequence
<220> FEATURE:
<223> OTHER INFORMATION: PCR primer F87Asn1

<400> SEQUENCE: 29
gcaggagacg ggttaaacac aagctggacg 30

<210> SEQ ID NO 30
<211> LENGTH: 30
<212> TYPE: DNA
<213> ORGANISM: Artificial Sequence
<220> FEATURE:
<223> OTHER INFORMATION: PCR primer F87Asn2

<400> SEQUENCE: 30
cgtccagctt gtgtttaacc cgtctcctgc 30

<210> SEQ ID NO 31
<211> LENGTH: 30
<212> TYPE: DNA
<213> ORGANISM: Artificial Sequence
<220> FEATURE:
<223> OTHER INFORMATION: PCR primer F87Asp1

<400> SEQUENCE: 31
gcaggagacg ggttagatac aagctggacg 30

<210> SEQ ID NO 32
<211> LENGTH: 29
<212> TYPE: DNA
<213> ORGANISM: Artificial Sequence
<220> FEATURE:
<223> OTHER INFORMATION: PCR primer F87Asp2

<400> SEQUENCE: 32
cgtccagctg tatctaaccc gtctcctgc 29

<210> SEQ ID NO 33
<211> LENGTH: 30
<212> TYPE: DNA
<213> ORGANISM: Artificial Sequence
<220> FEATURE:
<223> OTHER INFORMATION: PCR primer F87Arg1

<400> SEQUENCE: 33
gcaggagacg ggttacgtac aagctggacg 30

<210> SEQ ID NO 34
<211> LENGTH: 30
<212> TYPE: DNA
<213> ORGANISM: Artificial Sequence
<220> FEATURE:
<223> OTHER INFORMATION: PCR primer F87Arg2

<400> SEQUENCE: 34
cgtccagctt gtacgtaacc cgtctcctgc 30

<210> SEQ ID NO 35
<211> LENGTH: 30
<212> TYPE: DNA
<213> ORGANISM: Artificial Sequence
<220> FEATURE:
<223> OTHER INFORMATION: PCR primer F87Val1

<400> SEQUENCE: 35
gcaggagacg ggttagttac aagctggacg 30

<210> SEQ ID NO 36
<211> LENGTH: 30
<212> TYPE: DNA
<213> ORGANISM: Artificial Sequence
<220> FEATURE:
<223> OTHER INFORMATION: PCR primer F87Val2

<400> SEQUENCE: 36
cgtccagctt gtaactaacc cgtctcctgc 30

<210> SEQ ID NO 37
<211> LENGTH: 30
<212> TYPE: DNA
<213> ORGANISM: Artificial Sequence
<220> FEATURE:
<223> OTHER INFORMATION: PCR primer F87Ile1

<400> SEQUENCE: 37
gcaggagacg ggttaattac aagctggacg 30

<210> SEQ ID NO 38
<211> LENGTH: 30
<212> TYPE: DNA
<213> ORGANISM: Artificial Sequence
<220> FEATURE:
<223> OTHER INFORMATION: PCR primer F87Ile2

<400> SEQUENCE: 38
cgtccagctt gtaattaacc cgtctcctgc 30

<210> SEQ ID NO 39
<211> LENGTH: 30
<212> TYPE: DNA
<213> ORGANISM: Artificial Sequence
<220> FEATURE:
<223> OTHER INFORMATION: PCR primer F87Lys1

<400> SEQUENCE: 39
gcaggagacg ggttaaaaac aagctggacg 30

<210> SEQ ID NO 40
<211> LENGTH: 30

-continued

<212> TYPE: DNA
<213> ORGANISM: Artificial Sequence
<220> FEATURE:
<223> OTHER INFORMATION: PCR primer F87Lys2

<400> SEQUENCE: 40
cgtccagctt gtttttaacc cgtctcctgc 30

<210> SEQ ID NO 41
<211> LENGTH: 32
<212> TYPE: DNA
<213> ORGANISM: Artificial Sequence
<220> FEATURE:
<223> OTHER INFORMATION: PCR primer Bamfor

<400> SEQUENCE: 41
acaggatcca tcgatgctta ggaggtcata tg 32

<210> SEQ ID NO 42
<211> LENGTH: 19
<212> TYPE: DNA
<213> ORGANISM: Artificial Sequence
<220> FEATURE:
<223> OTHER INFORMATION: PCR primer Sacrev

<400> SEQUENCE: 42
gtgaaggaat accgccaag 19

CYTOCHROME P450 OXYGENASES

This application claims priority from, and is a continuation of U.S patent application Ser. No. 11/800,970, filed May 7, 2007 (now issued as U.S. Pat. No. 7,691,616), which is a continuation of U.S patent application Ser. No. 10/201,213, filed Jul. 22, 2002 (now issued as U.S. Pat. No. 7,226,768), which is a non-provisional of U.S. Application Ser. No. 60/306,766, filed Jul. 20, 2001, and U.S. Provisional Application No. 60/308,429, filed Jul. 27, 2001. Each of these prior applications is hereby incorporated by reference in its entirety.

FIELD OF THE INVENTION

The invention relates to novel uses for cytochrome P450 BM-3. In addition, the invention relates to novel variants of cytochrome P450 enzymes which are more resistant to organic solvents and/or are capable of oxidizing alkanes or alkenes.

BACKGROUND

The term paraffin (from Latin parum affinis=slight affinity) accurately reflects the nature of alkanes: these compounds are notoriously inert, and activating their C—H bonds presents a difficult chemical obstacle. In fact, one of the great challenges of contemporary catalysis is the controlled oxidation of hydrocarbons (Shilov 1997). Processes for controlled, stereo- and regioselective oxidation of hydrocarbon feed stocks to more valuable and useful products such as alcohols, ketones, acids, and peroxides would have a major impact on the chemical and pharmaceutical industries. However, selective oxyfunctionalization of hydrocarbons thus remains one of the great challenges for contemporary chemistry. Despite decades of effort, including recent advances (Chen et al., 2000; Hartman and Ernst, 2000; Thomas et al., 2001), chemical catalysts for alkane functionalization are characterized by low yields, poor selectivity and harsh conditions.

Biocatalysts (enzymes) that oxidize alkanes allow organisms to utilize hydrocarbons as a source of energy and cellular building blocks (Ashraf et al., 1994; Watkinson and Morgan, 1990). Enzymes have unique properties that distinguish them from most chemical catalyst. Most impressive is their ability to catalyze specific, and often difficult, chemical reactions in water at room temperature and atmospheric pressure. Forty years of screening alkane-assimilating organisms (Leadbetter and Foster, 1959) have identified a variety of multi-subunit, membrane-associated enzyme complexes, which have inspired curiousity and mimicry for their ability to catalyze selective oxidations at room temperature and ambient pressure (Scheller et al., 1996; Stevenson et al., 1996; Fox et al., 1990; Fisher et al., 1998; Benson et al., 1979). However, low catalyst turnover rates and limited stability make applications of biocatalytic C—H bond activation feasible only in a very few industrial processes where high value compounds are produced (Schmid et al., 2001).

Monooxygenases have unique properties that distinguish them from most chemical catalysts. Most impressive is their ability to catalyze the specific hydroxylation of non-activated C—H; one of the most useful biotransformation reactions, which is often difficult to achieve by chemical means, especially in water, at room temperature under atmospheric pressure. However, for chemical synthesis, organic solvents, not aqueous solutions, are generally used. The use of organic solvents has many advantages, most importantly are a) higher solubility of often in aqueous solutions poor soluble nonpolar compounds; b) suppression of water-dependent side reactions; c) alteration in enantioselectivity; and d) elimination of microbial contaminations (Dordick, 1992). The main drawback of enzymes functioning in organic solvents is their drastically reduced catalytic activity caused by dehydration of the enzyme (Klibanov, 1997). Little is known about this process and mainly hydrolytic enzymes such as esterases and lipases were used to study and improve their activity and stability in organic solvents (Kvittingen et al., 1992). Cofactor dependent oxidative enzymes have multiple domains and highly regulated electron transfer mechanisms to transport the reduction equivalent to the catalytic heme center (Munro et al., 1996; Beratan, 1996; Moser et al., 1995). Organic solvents can interfere by affecting redox potentials and interactions between single domains. However, no theory has been developed to explain the influence of organic solvents toward complex oxidative enzymes. Thus, the low organic solvent resistance of enzymes, in particular enzymes suitable for oxidation of hydrophobic substances, is a particularly challenging problem.

Cytochrome P450 Monoxygenases

The cytochrome P450 monooxygenases ("P450s") is a group of widely-distributed heme enzymes that inserts one oxygen atom of $O_2$ into a diverse range of hydrophobic substrates, often with high regio- and stereoselectivity. The second oxygen atom is reduced to H2O. The active sites of all cytochrome P450s contain an iron protoporphryin IX with cysteinate as the fifth ligand; the final coordination site is left to bind and activate molecular oxygen (Groves et al., 1995). For many of the P450-catalyzed reactions, no chemical catalysts come close in performance (Lewis, 1996). These enzymes, however, are often only poorly active towards non-natural substrates and cannot tolerate normal process conditions, including organic solvents (Lewis, 1996; Kuhn-Velten, 1997). Simply put, they are a process engineering nightmare.

One particular P450 enzyme, cytochrome P450 BM-3 from *Bacillus megaterium* (EC 1.14.14.1) also known as CYP102, is a water-soluble, catalytically self-sufficient P450 containing a monooxygenase domain (64 kD) and a reductase domain (54 kD) in a single polypeptide chain (Narhi and Fulco, 1986 and 1987; Miura and Fulco, 1975; Ruettinger et al., 1989). The minimum requirements for activity are substrate, dioxygen and the cofactor nicotinamide adenine dinucleotide phosphate (NADPH). Nucleotide and amino acid sequences for P450 BM-3 can be found in, and are hereby incorporated by reference from, the GenBank database under the accession Nos. J04832 (SEQ ID NO:1) and P14779 (SEQ ID NO:2), respectively.

P450 BM-3 hydroxylates fatty acids of chain length between C12 and C18 at subterminal positions, and the regioselectivity of oxygen insertion depends on the chain length (Miura and Fulco, 1975; Boddupalli et al., 1990). The optimal chain length of saturated fatty acids for P450 BM-3 is 14-16 carbons, and the enzyme was initially believed to have no activity towards fatty acids smaller than C12 (Miura and Fulco, 1975). P450 BM-3 is also known to hydroxylate the corresponding fatty acid amides and alcohols and forms epoxides from unsaturated fatty acids (Miura and Fulco, 1975; Capdevila et al., 1996; Graham-Lorence et al., 1997; Ruettinger and Fulco, 1981). The enzyme was reported to be inactive towards alkanes and methyl esters lacking the polar functionality of the natural substrates (Miura and Fulco, 1975). However, there were indications that P450 BM-3 could accept shorter-chain alkanes, although with very low activity (Munro et al., 1993).

Powerful techniques for creating enzymes with modified or improved properties are now available, such as directed evolution (Arnold, 1998), in which iterative cycles of random mutagenesis, recombination and functional screening for improved enzymes accumulate the mutations that confer the desired properties. Mutant P450 BM-3 enzymes with modified activity have now been reported in the literature. For example, an F87A (Phe87→Ala87) mutant was found to display a higher activity for the 12-pCNA substrate (Farinas et al., 2001; Schwaneberg et al., 1999). In addition, by reengineering the fatty acid binding site to accommodate fatty acids with a chain-length shorter than 12 (Li et al., 2001; Ost et al., 2000), Li and coworkers (2001) found mutants that are capable to hydroxylate indole which dimerizes in the presence of oxygen to indigo and indinlbin, and Carmichael and Wong (2001) found P450 BM-3 mutants that could oxidize polycyclic aromatic hydrocarbons ("PAHs") such as phenanthrene, fluoranthene, and pyrene. In addition, the Schmid group recently reported mutants of P450 BM-3 that can hydroxylate a variety of nonnatural substrates, including octane, several aromatic compounds and heterocyclic compounds (Appel et al., 2001). In addition, P450 BM-3 mutants for epoxidation of substrates such as long-chain unsaturated fatty acids (Miura and Fulco, 1975; Capdevila et al., 1996; Graham-Lorence et al., 1997; Ruettinger and Fulco, 1981) and styrene (Fruetel, J A et al., 1994) have been suggested.

Many of the wild-type and mutant P450 BM-3 substrates have, if the performance of the catalyst is sufficient, bright prospective applications as products or intermediates in fine chemical synthesis (Schneider et al., 1999). Unfortunately, until now, the alkane hydroxylation activities of P450 BM-3 mutants are still limited, especially for lower alkanes. Moreover, many of P450 BM-3 substrates (fatty acids, alcohols, amides, C>12 alkanes, polyaromatic hydrocarbons, heterocycles, etc.), are notoriously insoluble in aqueous solution and require for solubilization an organic co-solvent, and the organic solvent resistance of P450 BM-3 in water miscible co-solvents is low and insufficient for industrial applications. To date, no P450 BM-3 mutants with improved or altered solvent resistance have been identified.

Thus, there is a need in the art for industrially useful oxidation catalysts for alkane hydroxylation and alkene epoxidation; particularly on hydrocarbon substrates that are shorter than its preferred substrates, the fatty acids. While various alkane hydroxylases are known, for example w-hydroxylase and methane monooxygenase, none of these naturally-occurring enzymes have the practical advantages of an enzyme such as P450 BM-3, which is highly expressed in recombinant form in bacteria and contains all its functional domains in a single polypeptide chain. There is also a need for oxygenase enzymes that can operate efficiently in organic co-solvents. This invention addresses these and other needs in the art.

SUMMARY OF THE INVENTION

The present invention is based on the discovery of P450 BM-3 variants that have improved alkane oxidation activity, alkene oxidation activity, and/or improved stability in organic co-solvents.

Accordingly, the invention provides an isolated nucleic acid encoding a cytochrome P450 variant which has a higher capability than the corresponding wild-type cytochrome P450 to oxidize at least one substrate selected from an alkane comprising a carbon-chain of no more than 8 carbons and an alkene comprising a carbon-chain of no more than 8 carbons, wherein the wild-type cytochrome P450 comprises an amino acid sequence having at least 60% sequence identity to SEQ ID NO:2 (Le., the wild-type sequence of P450 BM-3), and the cytochrome P450 variant comprises an amino acid substitution at a residue corresponding to a residue of SEQ ID NO:2 selected from V78, H236, and E252. In one embodiment, the amino acid sequence has at least 80% sequence identity to SEQ ID NO:2. Preferably, the amino acid sequence is SEQ ID NO:2. In another embodiment, the higher capability is a higher maximum turnover rate of the substrate into an oxidized product, and the maximum turnover rate of the variant is at least 5 times, preferably at least 10 times, the maximum turnover rate of the wild-type. When the substrate is an alkane, the capability to oxidize is preferably the capability to hydroxylate, and the alkane can be selected from one or more of octane, hexane, cyclohexane, pentane, butane, and propane. When the substrate is an alkene, the capability to oxidize can be either or both of the capability to epoxidate or hydroxylate, and the alkene can be selected from one or more of 1-hexene, 2-hexene, 3-hexene, cyclohexene, isoprene, allyl chloride, propene, and styrene.

In another embodiment, the cytochrome P450 variant comprises amino acid substitutions at residues corresponding to at least two residues of SEQ ID NO:2 selected from V78, H236, and E252, preferably at all of these residues, and, even more preferably, the amino acid substitution is selected from V78A, H236Q, and E252G. When the wild-type sequence is that of P450 BM-3, the cytochrome P450 variant can comprise amino acid substitutions at two residues selected from V78, H236, and E252, preferably all of these residues, and, even more preferably, the amino acid substitutions are V78A, H236Q, and E252G. In addition, the cytochrome P450 variant may comprise at least one further amino acid substitution at a residue selected from H138, T175, V178, A184, N186, F205, D217, S226, 8255, A290, A295, L353, and G396, Optionally, the amino acid substitution at these residues is selected from one or more of H138Y, T175I, V178I, A184V, N186D, F205C, D217V, S226I, S226R, R255S, A290V, A295T, L353V, and G396M. In preferred embodiments, the cytochrome P450 variant comprises the amino acid substitutions V78A, H138Y, T175I, V1781, A184V, H236Q, E252G, R255S, A290V, A295T, and L353V, or the amino acid substitutions V78A, T175I, A184V, F205C, S226R, H236Q, E252G, R255S, A290V, and L353V.

The invention also provides an isolated nucleic acid encoding a cytochrome P450 variant which has a higher organic solvent-resistance than the corresponding wild-type cytochrome P450, wherein the wild-type cytochrome P450 comprises an amino acid sequence has at least 60% sequence identity to SEQ ID NO:2, and the cytochrome P450 variant comprises an amino acid substitution at a residue corresponding to a residue of SEQ ID NO:2 selected from T235, R471, E494, and S1024. In one embodiment, the amino acid sequence has at least 80% sequence identity to SEQ ID NO:2. Preferably, the amino acid sequence is SEQ ID NO:2. The organic solvent-resistance may be, for example, a higher maximum turnover rate of a substrate into an oxidized product in a solution comprising an organic solvent, and the oxidized product may be a hydroxylated product. In another embodiment, the organic solvent is selected from THF, DMSO, methanol, ethanol, propanol, dioxane, and dimethylformamide. For example, when the solution comprises 25% (v/v) DMSO, the hydroxylation activity of the cytochrome P450 BM-3 variant can be at least twice the hydroxylation activity of wild-type cytochrome P450 BM-3. Also, when the solution comprises 2% (v/v) THF, the hydroxylation activity of the cytochrome P450 BM-3 variant can be at least twice the hydroxylation activity of wild-type cytochrome P450 BM-3.

In particular embodiments, the cytochrome P450 variant may comprise amino acid substitutions at residues corresponding to at least two residues of SEQ ID NO:2 selected from T235, R471, E494, and S1024; preferably at least three residues, an the amino acid substitutions at residues may correspond to T235, R471, E494, and S1024 of SEQ ID NO:2. Alternatively, when the wild-type sequence is SEQ ID NO:2, the cytochrome P450 variant may comprise amino acid substitutions at least two residues selected from T235, R471, E494, and S1024, preferably three, and, even more preferably, the cytochrome P450 variant comprises amino acid substitutions at T235, R471, E494, and S1024. Optionally, the amino acid substitutions can be T235A, R471A, E494K, and S1024E. In any of the foregoing embodiment, the cytochrome P450 variant further may further comprise an amino acid substitution at residue F87, for example, F87A. In a preferred embodiment, the cytochrome P450 variant comprises the mutations F87A, T235A, R471A, E494K, and S1024E.

The invention also provides for an isolated nucleic acid encoding a variant of a parent cytochrome P450 oxygenase, the variant having (i) a higher ability than the parent to oxidize a substrate selected from an alkane comprising a carbon-chain of no more than 8 carbons or alkene comprising a carbon-chain of less than 8 carbons; and (ii) at least one amino acid substitution in a secondary structural element of the cytochrome P450 heme domain selected from the helix B' domain, the helix H domain, and the helix I domain, wherein the parent comprises an amino acid sequence having at least 60% sequence identity to SEQ ID NO:2. Preferably, the amino acid sequence of the parent has at least 80% sequence identity to SEQ ID NO:2. Even more preferably, the amino acid sequence of the parent is SEQ ID NO:2. The amino acid substitution can, for example, be at a residue corresponding to a residue of SEQ ID NO:2 selected from V78, H236, and E252, and correspond to V78A, H236Q, or E252G. Optionally, the variant further comprises at least one amino acid substitution at a residue corresponding to a residue of SEQ ID NO:2 selected from H138, T175, V178, A184, F205, S226, R255, A290, A295, and L353, such as, for example, V78A, H138Y, T175I, V178I, A184V, F205C, S226R, H236Q, E252G, R255S, A290V, A295T, and L353V. Preferably, the amino acid substitutions are at residues corresponding to amino acid residues V78, H236, and E252 of SEQ ID NO:2, such as, for example, V78A, H236Q, and E252G.

The invention also provides for an isolated nucleic acid encoding a variant of a parent cytochrome P450 oxygenase, the variant having: (i) a higher organic solvent resistance than the parent; and (ii) at least one amino acid substitution in a secondary structural element of the selected from the helix H domain of the cytochrome P450 heme domain and the helix of the Ravin domain; wherein the parent comprises an amino acid sequence having at least 60% sequence identity to SEQ ID NO:2. In one embodiment, the amino acid sequence of the parent has at least 80% sequence identity to SEQ ID NO:2. Preferably, the amino acid sequence of the parent is SEQ ID NO:2. The amino acid substitution can be at a residue corresponding to a residue of SEQ ID NO:2 selected from T235 and E494, and the cytochrome P450 variant may optionally comprise a further amino acid substitution at a residue corresponding to a residue of SEQ ID NO:2 selected from R471 and S 1024. If so, the amino acid substitution can be selected from T235A and E494K, and the further amino acid substitution can be selected from R471A and S1024E. In a preferred embodiment, the amino acid substitution is selected from T235A and E494K, and the further amino acid substitution is selected from R471A and S1024E. In another preferred embodiment, the variant further comprises an amino acid substitution at a residue corresponding to residue F87 of SEQ ID NO:2, such as, for example, F87A, F87G, F87V, F87I, F87F, F87W, F87D, F87N, F87H, F87K, or F87R. A preferred variant comprises amino acid substitutions at residues corresponding to amino acid residues T235, R471, E494, and S1024 of SEQ ID NO:2, and the amino acid substitutions are preferably T235A, R471A, E494K, and S1024E, with or without the amino acid substitution F87A.

The invention provides for an isolated nucleic acid encoding a cytochrome P450 variant, the cytochrome P450 variant comprising the amino acid substitutions V78A, H236Q, and E252G of SEQ ID NO:2, wherein the variant may further comprise the amino acid substitutions H138Y, T1751, V178I, A184V, N186D, D217V, S226I, R255S, A290V, A295T, L353V, and G396M, or the amino acid substitutions T175I, A184V, F205C, S226R, R255S, A290V, L353V.

The invention also provides for an isolated nucleic acid encoding a cytochrome P450 variant, the cytochrome P450 variant comprising the amino acid substitutions T235A, R471A, E494K, and S1024E of SEQ ID NO:2, optionally comprising the amino acid substitution F87A.

Finally, the invention also provides for amino acid sequences comprising the above-mentioned amino acid substitutions.

The above features and many other advantages of the invention will become better understood by reference to the following detailed description when taken in conjunction with the accompanying drawings.

BRIEF DESCRIPTION OF THE DRAWINGS

FIGS. 20A and B. Sequence alignments of P450 BM-3 (GenBank Accession No. P14779 (SEQ ID NO:2)) with CYP 2C3 (GenBank P00182, SEQ ID NO:3), CYP 2C9 (GenBank P11712; SEQ ID NO:4), CYP 2D1v (GenBank P10633; SEQ ID NO:5), and CYP 108 (GenBank P33006; SEQ ID NO:6).

DETAILED DESCRIPTION OF THE INVENTION

Figure 1:
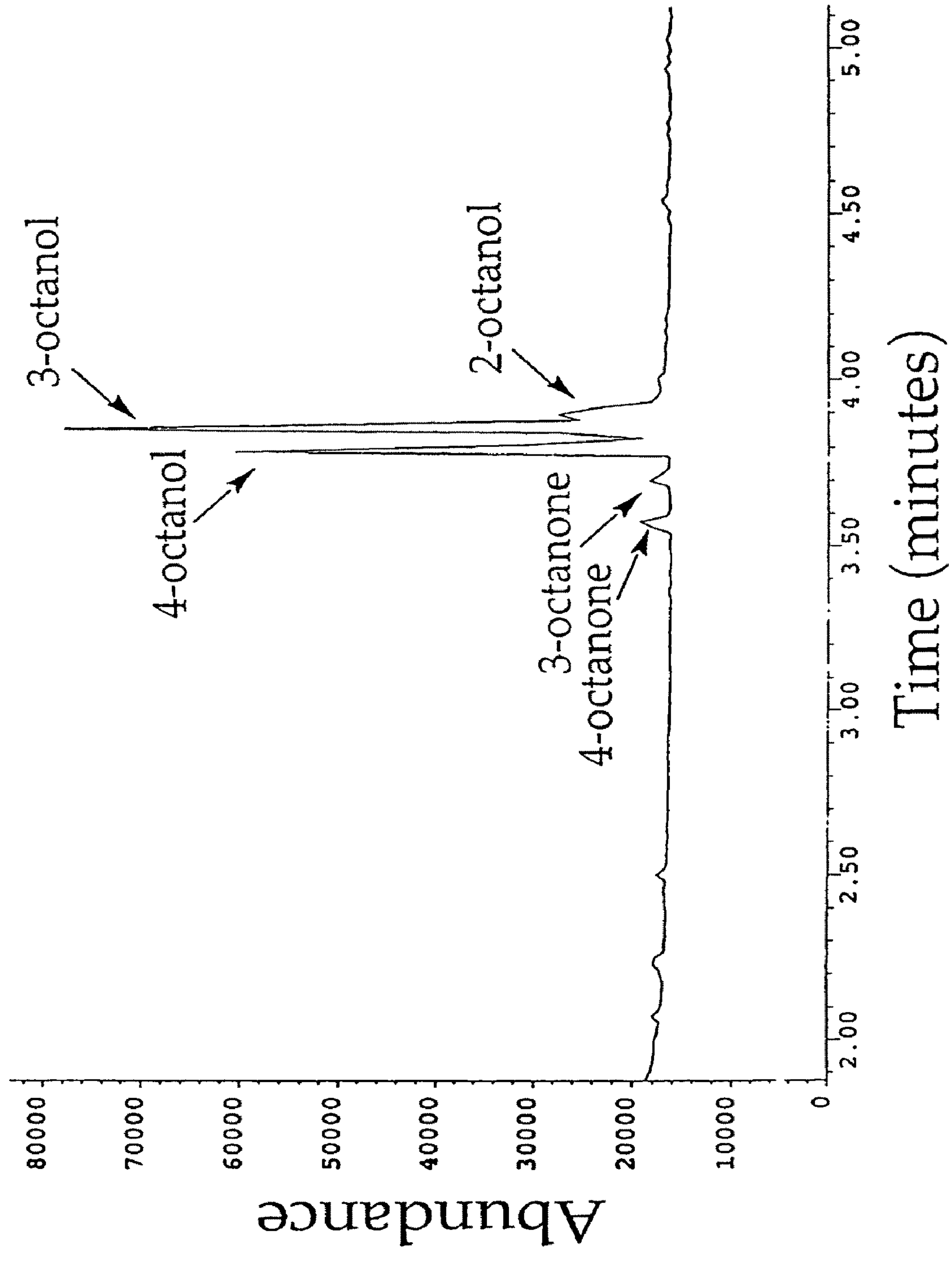
FIG. 1. Gas chromatogram of the oxidation products of octane, catalyzed by wild-type P450 BM-3.

The invention provides novel variants or mutants of P450 BM-3 which are capable of oxidizing alkanes, alkane derivatives, and/or saturated or unsaturated hydrocarbons. Accordingly, the invention provides variant P450 BM-3 enzymes which have a higher oxidation activity towards at least one alkane, alkane derivative, alkene, or alkene derivative than wild-type P450 BM-3. Preferably, the variant P4590 BM-3 has a higher oxidation activity towards a saturated hydrocarbon such as octane, hexane, cyclohexane, propane, ethane, and/or butane, or towards an unsaturated hydrocarbon such as propene, hexene, cyclohexene, isoprene, allyl chloride, and/or styrene, or derivatives thereof, than wild-type P450 BM-3. In one embodiment, the P450 BM-3 variants comprise mutations at one or more of the following residues of SEQ ID NO:2, counting the starting methionine as position 0 ("zero"): V78, H138, T175, V178, A184, N186, F205, D217, S226, H236, E252, R255, A290, A295, L353, and G396. Preferably, the mutation or mutations are selected from V78A, H138Y, T175I, V178I, A184V, N186D, F205C, D217V, S226I, S226R, H236Q, E252G, R255S, A290V, A295T, L353V, and G396M. The P450 BM-3 variants can comprise at least one, preferably at least three, and more preferably at least 5, and even more preferably at least all of these amino acid mutations. In a particularly preferred embodiment, the P450 BM-3 variant comprises the mutations V78A, H236Q, and the E252G mutations. See also Table 1A.

In addition, the invention provides P450 BM-3 variants with a higher organic solvent resistance in at least one water-miscible co-solvent than wild-type P450 BM-3. Preferably, the P450 BM-3 variants of the invention have a higher organic solvent resistance towards water-miscible co-solvents such as, but not limited to, DMSO, THF, methanol, ethanol, propanol, dioxane, and dimethylfonamide. In a preferred embodiment, the P450 BM-3 variant comprises mutations at one or more of the following residues of SEQ ID NO:2, counting the starting methionine as position 0 ("zero"): F87, T235, R471, E494, and S1024. The mutation at F87 can be, for example, F87A, F87G, F87V, F87I, F87F, F87W, F87D, F87N, F87H, F87K, F87. The mutations at T235, R471, and E494 can be, for example, T235A, R471C, R471A, and E494K. The mutation at S1024 can be, for example, S1024R, S1024T, S1024K, and S1024E. In a preferred embodiment, the novel P450 BM-3 variants comprise mutations in at least one, preferably at least three of amino acid residues F87, T235, R471, E494, and S1024. Most preferably, the variant comprises the mutations T235A, R471A, E494K, and S1024E, with or without the mutation F87A. See also Table 1A.

TABLE 1A

| Preferred Cytochrome P450 Mutated Amino Acid Residues and Mutations | |
|---|---|
| Amino Acid Residue of SEQ ID NO: 2 | Amino Acid Mutation |
| V78 | V78A |
| F87 | F87A |
| H138 | H138Y |
| T175 | T175I |
| V178 | V178I |
| A184 | A184V |
| N186 | N186D |
| F205 | F205C |
| D217 | D217V |
| S226 | S226I, S226R |
| T235 | T235A |
| H236 | H236Q |
| E252 | E252G |
| R255 | R255S |
| A290 | A290V |
| A295 | A295T |
| L353 | L353V |
| G396 | G396M |
| R471 | R471A |
| E494 | E494K |
| S1024 | S1024E |

In addition, the invention provides for P450 BM-3 mutants having specific nucleic acid and amino acid sequences. The nucleic acid sequences include those which encode for the P450 BM-3 variants in Table 1B. The amino acid sequences include those which have the combinations of amino acid mutations in Table 1B, where all mutations refer to SEQ ID NO:2, counting the starting methionine residue as position 0 ("zero").

TABLE 1B

| Preferred P450 BM-3 Variants | |
|---|---|
| Designation | Amino Acid Mutations in Wild-Type P450 BM-3 (SEO ID NO: 2) |
| ix139-3 | V78A, H138Y, T175I, V178I, A184V, H236Q, E252G, R255S, A290V, A295T, L353V |
| ix139-37 | V78A, T175I, A184V, N186D, D217V, H236Q, E252G, A290V, L353V, G396M |
| ix139_43J | V78A, T175I, A184V, S226I, H236Q, E252G, A290V, L353V V78A, T175I, A184V, F205C, S226R, H236Q, E252G, R255S, A290V, L353V |
| F87A5F5 | F87A, T235A, R471A, E494K, S1024E |
| F87ABC1F10 | F87A, T235A, R471A, S1024T |
| W5F5 | T235A, R471A, E494K, S1024E |

Moreover, the invention provides for novel variants of P450 enzymes other than P450 BM-3, which have a higher activity for alkane oxidation and/or higher solvent resistance than the corresponding wild-type enzyme. These novel variants can be identified when aligned with the respective non-BM-3 amino acid sequence with that of P450 BM-3 (SEQ ID NO:2), amino acid positions in the non-BM-3 sequence that are aligned with one or more of the following amino acid residues in SEQ ID NO:2 are identified: V78, F87, H138, T175, V178, A184, N186, F205, D217, S226, T235, H236, E252, R255, A290, A295, L353, G396M, R471, E494, and S1024. Mutations in amino acid residues of the non-BM-3 enzyme which are aligned with and identical to the aforementioned BM-3 amino acid residues results in novel P450 variants according to the invention. See FIG. 20. Preferably, the mutation in the non-BM-3 sequence results in one or more of the following amino acid substitutions: V78'A, F87'A, F87'G, F87'V, F87'I, F87'F, F87'W, F87'D, F87'N, F87'H, F87'K, F87'R, H138'Y, T175'I, V178'I, A184'V, N186'D, F205'C, D217'V, S226'I, S226'R, T235'A, H236'Q, E252'G, R255'S, A290'V, A295'T, L353'V, G396'M, R471'C, R471'A, E494'K, S1024'R, S1024'T, S1024'K, and S1024'E, where the amino acid residue is the amino acid residue aligned with the corresponding P450-BM-3 residue (denoted by prime (') sign). Preferred, non-limiting examples of such novel "non-BM-3" enzymes are listed in Table 2.

TABLE 2

| Preferred Non-P450 BM-3 Variants | | | |
|---|---|---|---|
| Wild-Type Enzyme | Wild-Type Amino Acid Sequence | Mutation(s) | Aligned P450 BM-3 Mutation(s) |
| CYP 2C3 | SEQ ID NO: 3 | H266Q | H236'Q |
| CYP2C9 | SEQ ID NO: 4 | E285G | E252'G |
| CYP 2D1v | SEQ ID NO: 5 | E296G, L398V | E252'G, L353'V |
| CYP 108 | SEQ ID NO: 6 | A293V | A290'V |

In addition, the invention provides for variants of non-BM-3 enzymes, wherein the wild-type sequences are at least 30, preferably at least 50, more preferably at least 70, even more preferably at least 90%, and optimally at least 95% identical to SEQ ID NO: 2. Preferred, non-limiting examples of such novel "non-BM-3 P450s" and their heme domains are described herein, listed in Table 2 and depicted in FIG. 20. In one embodiment, the oxidase activity of a P450 variant for one or more alkane- or alkene-substrates is at least five, more preferably at least 10, and even more preferably at least 15 times that of the corresponding wild-type cytochrome P450. In another embodiment, the organic solvent resistance of a P450 variant is at least two, preferably at least 3, and even more preferably at least five times that of the corresponding wild-type cytochrome P450.

In addition, the "non-BM-3 P450" may be a P450 BM-3 variant, which has one or more mutations as compared to wild-type P450 BM-3. Such variants, including variants displaying more than 60% sequence identity to SEQ ID NO:2, are described in, e.g., PCT application PCT/US02/11954, filed Apr. 16, 2002.

Wild-Type Cytochrome P450 Enzymes

Crystal structures of wildtype P450 BM-3 with and without substrate reveal large conformational changes upon substrate binding at the active site (Haines et al., 2001; Li and Poulos, 1997; Paulsen and Ornstein, 1995; and Chang and Loew, 2000). The substrate free structure displays an open access channel with 17 to 21 ordered water molecules. Substrate recognition serves as a conformational trigger to close the channel, which dehydrates the active site, increases the redox potential, and allows dioxygen to bind to the heme.

The activity of P450 BM-3 on saturated fatty acids follows the order C15=C16>C14>C17>C13>C18>C12 (Oliver et al., 1997). On the C16 fatty acid, $k_{cat}$=81 $s^{-1}$ and $K_m$=1.4×$10^{-6}$ M ($k_{cat}/K_m$=6.0×$10^7$ $M^{-1}s^{-1}$). With the C12 fatty acid, kcat=26 $s^{-1}$, $K_m$=136×$10^{-6}$ M and $k_{cat}/K_m$=1.9×$10^5$ $M^{-1}s^{-1}$ (Oliver et al., 1997).

P450 BM-3 may be compared to naturally-occurring enzyme that hydroxylates linear alkanes. For example, *Pseudomonas oleovorans* is able to oxidize n-alkanes using hydroxylase machinery comprising an integral membrane oxygenase (ω-hydroxylase), a soluble NADH-dependent reductase and a soluble metalloprotein (rubredoxin) which transfers electrons from the reductase to the hydroxylase (Staij en et al., 2000). The ω-hydroxylase has been cloned from *P. oleovorans* into *Escherichia coli*, where it has been expressed and purified (Shanklin et al., 1997). The specific activity of this ω-hydroxylase for octane (5.2 units/mg hydroxylase (Shanklin et al., 1997)) is ~13 times greater than that of P450 BM-3 (0.4 units/mg enzyme) (See Example 1). (The specific activity of the complete *P. oleovorans* system, including the rubredoxin and the reductase, is of course less than 5.2 units/mg). Thus, wildtype P450 BM-3 is inefficient relative to this (and other) naturally occurring enzyme for alkane hydroxylation.

A tyrosine (Tyr51) at the entrance to the substrate-binding pocket makes a hydrogen bond to the carboxylate group of the substrate in the crystal structure of the enzyme bound with palmitoleic acid (Li and Poulos, 1997). Arg 47, also at the entrance to the binding pocket, may form an ionic interaction as well. Nonpolar alkane substrates must rely solely on hydrophobic partitioning into the enzyme's extended substrate channel, and poor substrate recognition may contribute to P450 BM-3's sluggish activity on octane and other alkanes or alkenes.

Directed Evolution

The present invention provides evolved enzymes which oxidize alkanes to a higher degree, or which have a higher resistance to organic solvents and/or co-solvents, than the corresponding wild-type enzyme(s). As described in Example 3, a P450 BM-3 variant according to the invention has been generated which surpasses the activity of the alkane hydroxylase from *P. oleovorans* on octane. The mutant also showed similar high activity on hexane, cyclohexane, and pentane, which was not shown to be a substrate for P450 BM-3 before, and is also efficient on butane and propane. Thus, the cytochrome P450 variants of the invention show that it is possible to reach activities on unreactive nonnatural substrates that are close to the activity of the native enzyme, e.g., P450 BM-3, on its best natural substrates (for P450 BM-3; long chain fatty acids), which are about 1000 times higher than that of eukaryotic P450s and one of the highest activities of P450s known so far.

The strategy described here also provides improvements of the P450 BM-3 activity on a number of substrates, including shorter chain alkenes such as propene, allyl chloride, isoprene, 1-hexene and styrene. It should also be possible to target other key properties such as regioselectivity, enantiosetectivity and catalyst stability.

A preferred technique to improve the alkane-oxidation and co-solvent resistance of wild-type or parent cytochrome P450 enzymes, including P450 BM-3, is directed evolution. General methods for generating libraries and isolating and identifying improved proteins according to the invention using directed evolution are described briefly below. More extensive descriptions can be found in, for example, Arnold (1998); U.S. Pat. Nos. 5,741,691; 5,811,238; 5,605,793 and 5,830,721; and International Applications WO 98/42832, WO 95/22625, WO 97/20078, WO 95/41653 and WO 98/27230.

The basic steps in directed evolution are (1) the generation of mutant libraries of polynucleotides from a parent or wild-type sequence; (2) (optional) expression of the mutant polynucleotides to create a mutant polypeptide library; (3) screening/selecting the polynucleotide or polypeptide library for a desired property of a polynucleotide or polypeptide; and (4) selecting mutants which possess a higher level of the desired property; and (5) repeating steps (1) to (5) using the selected mutant(s) as parent(s) until one or more mutants displaying a sufficient level of the desired activity have been obtained. The property can be, but is not limited to, alkane oxidation capability and solvent-resistance.

The parent protein or enzyme to be evolved can be a wild-type protein or enzyme, or a variant or mutant. The parent polynucleotide can be retrieved from any suitable commercial or non-commercial source. The parent polynucleotide can correspond to a full-length gene or a partial gene, and may be of various lengths. Preferably the parent polynucleotide is from 50 to 50,000 base pairs. It is contemplated that entire vectors containing the nucleic acid encoding the parent protein of interest may be used in the methods of this invention.

Any method can be used for generating mutations in the parent polynucleotide sequence to provide a library of evolved polynucleotides, including error-prone polymerase chain reaction, cassette mutagenesis (in which the specific region optimized is replaced with a synthetically mutagenized oligonucleotide), oligonucleotide-directed mutagenesis, parallel PCR (which uses a large number of different PCR reactions that occur in parallel in the same vessel, such that the product of one reaction primes the product of another reaction), random mutagenesis (e.g., by random fragmentation and reassembly of the fragments by mutual priming); site-specific mutations (introduced into long sequences by random fragmentation of the template followed by reassembly of the fragments in the presence of mutagenic oligonucleotides); parallel PCR (e.g., recombination on a pool of DNA sequences); sexual PCR; and chemical mutagenesis (e.g., by sodium bisulfite, nitrous acid, hydroxylamine, hydrazine, formic acid, or by adding nitrosoguanidine, 5-bromouracil, 2-aminopurine, and acridine to the PCR reaction in place of the nucleotide precursor; or by adding intercalating agents such as proflavine, acriflavine, quinacrine); irradiation (X-rays or ultraviolet light, and/or subjecting the polynucleotide to propagation in a host cell that is deficient in normal DNA damage repair function); or DNA shuffling (e.g., in vitro or in vivo homologous recombination of pools of nucleic acid fragments or polynucleotides). Any one of these techniques can also be employed under low-fidelity polymerization conditions to introduce a low level of point mutations randomly over a long sequence, or to mutagenize a mixture of fragments of unknown sequence.

Once the evolved polynucleotide molecules are generated they can be cloned into a suitable vector selected by the skilled artisan according to methods well known in the art. If a mixed population of the specific nucleic acid sequence is cloned into a vector it can be clonally amplified by inserting each vector into a host cell and allowing the host cell to amplify the vector and/or express the mutant or variant protein or enzyme sequence. Any one of the well-known procedures for inserting expression vectors into a cell for expression of a given peptide or protein may tie utilized. Suitable vectors include plasmids and viruses, particularly those known to be compatible with host cells that express oxidation enzymes or oxygenases. *E. coli* is one exemplary preferred host cell. Other exemplary cells include other bacterial cells such as *Bacillus* and *Pseudomonas*, archaebacteria, yeast cells such as *Saccharomyces cerevisiae*, insect cells and filamentous fungi such as any species of *Aspergillus* cells. For some applications, plant, human, mammalian or other animal cells may be preferred. Suitable host cells may be transformed, transfected or infected as appropriate by any suitable method including electroporation, $CaCl_2$ mediated DNA uptake, fungal infection, microinjection, microprojectile transformation, viral infection, or other established methods.

The mixed population of polynucleotides or proteins may then be tested or screened to identify the recombinant polynucleotide or protein having a higher level of the desired activity or property. The mutation/screening steps can then be repeated until the selected mutant(s) display a sufficient level of the desired activity or property. Briefly, after the sufficient level has been achieved, each selected protein or enzyme can be readily isolated and purified from the expression system, or media, if secreted. It can then be subjected to assays designed to further test functional activity of the particular protein or enzyme. Such experiments for various proteins are well known in the art, and are described below and in the Examples below.

The evolved enzymes can be used in biocatalytic processes for, e.g., alkane hydroxylation and alkene epoxidation, or for improving yield of reactions involving oxidation of substrates with low solubility in aqueous solutions. The enzyme variants of the invention can be used in biocatalytic processes for production of chemicals from hydrocarbons, particularly alkanes and alkenes, in soluble or immobilized form. Furthermore, the enzyme variants can be used in live cells or in dead cells, or it can be partially purified from the cells. One preferred process would be to use the enzyme variants in any of these forms (except live cells) in an organic solvent, in liquid or even gas phase, or for example in a super-critical fluid like $CO_2$. The organic solvent would dissolve high concentrations of the non-polar substrate, so that the enzyme could work efficiently on that substrate.

Recycling the cofactor can present difficulties for such a process. However, cofactor recycling methods well known in the art can be applied. For example, an enzyme capable of regenerating the cofactor, using a second substrate can be used. Alternatively, the enzyme can be used in living cells, and the cofactor recycling can be accomplished by feeding the cells the appropriate substrate(s). The NADPH and oxygen can also be replaced by a peroxide, for example hydrogen peroxide, butyl peroxide or cumene peroxide, or by another oxidant. Mutations that enhance the efficiency of peroxide-based oxidation by BM-3 or other cytochrome P450 enzymes can serve to enhance the peroxide shunt activity of the enzyme variants described here. The mutations described here can be combined with such mutations, for example, and tested for their contributions to peroxide-driven alkane and alkene oxidation.

Screening Assays

The method of screening for identifying mutants or variants, for further testing or for the next round of mutation, will depend on the desired property sought. For example, in this invention, recombinant nucleic acid which encode cytochrome P450 enzymes with improved alkane-oxidation capability and/or solvent-resistance can be screened for alkane-oxidation activity or for activity or stability in a solvent/co-solvent mixture. Such tests are well known in the art. Examples of suitable tests are provided in the Examples and discussed below.

In a broad aspect, a screening method to detect oxidation comprises combining, in any order, substrate, oxygen donor, and test oxidation enzyme. The assay components can be placed in or on any suitable medium, carrier or support, and are combined under predetermined conditions. The conditions are chosen to facilitate, suit, promote, investigate or test the oxidation of the substrate by the oxygen donor in the presence of the test enzyme, and may be modified during the assay. The amount of oxidation product, i.e., oxidized substrate, is thereafter detected using a suitable method. Further, as described in WO 99/60096, a screening method can comprise a coupling enzyme such as horseradish peroxidase to enable or enhance the detection of successful oxidation. In some embodiments, one or more cofactors, coenzymes and additional or ancillary proteins may be used to promote or enhance activity of the test oxidation enzyme, coupling enzyme, or both.

In a preferred embodiment, it is not necessary to recover test enzyme from host cells that express them, because the host cells are used in the screening method, in a so-called "whole cell" assay. In this embodiment, substrate, oxygen donor, and other components of the screening assay, are supplied to the transformed host cells or to the growth media or support for the cells. In one form of this approach, the test enzyme is expressed and retained inside the host cell, and the substrate, oxygen donor, and other components are added to the solution or plate containing the cells and cross the cell membrane and enter the cell. Alternatively, the host cells can be lysed so that all intracellular components, including any recombinantly expressed intracellular enzyme variant, can be in direct contact with any added substrate, oxygen donor, and other components.

Resulting oxygenated products are detected by suitable means. For example, the oxidation product may be a colored, luminescent, or fluorescent compound, so that transformed host cells that produce more active oxidation enzymes "light up" in the assay and can be readily identified, and can be distinguished or separated from cells which do not "light up" as much and which produce inactive enzymes, less active enzymes, or no enzymes. A fluorescent reaction product can be achieved, for example, by using a coupling enzyme, such as laccase or horseradish peroxidase, which forms fluorescent polymers from the oxidation product. A chemiluminescent agent, such as luminol, can also be used to enhance the detectability of the luminescent reaction product, such as the fluorescent polymers. Detectable reaction products also include color changes, such as colored materials that absorb measurable visible or UV light.

Figure 2:
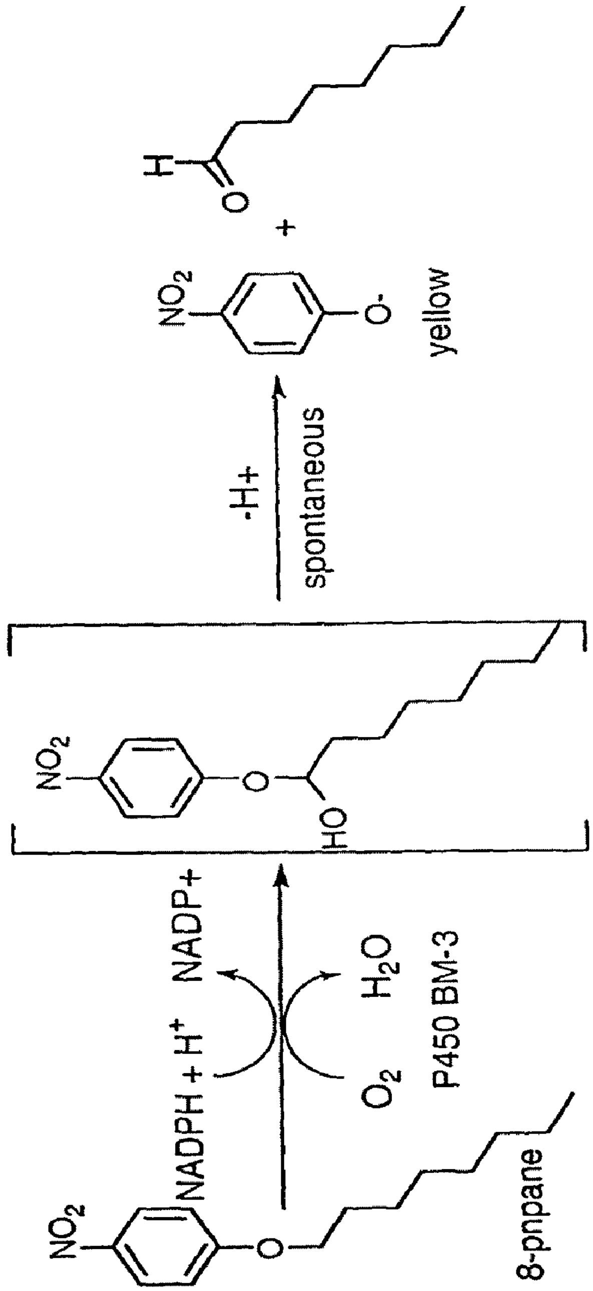
FIG. 2. The screening assay for alkane oxidation activity uses the substrate analog δ-pnpane (p-nitrophenoxyoctane). Terminal hydroxylation generates the unstable hemiacetal, which decomposes to the aldehyde and p-nitrophenolate, which is monitored at 410 nm.
Figure 3:
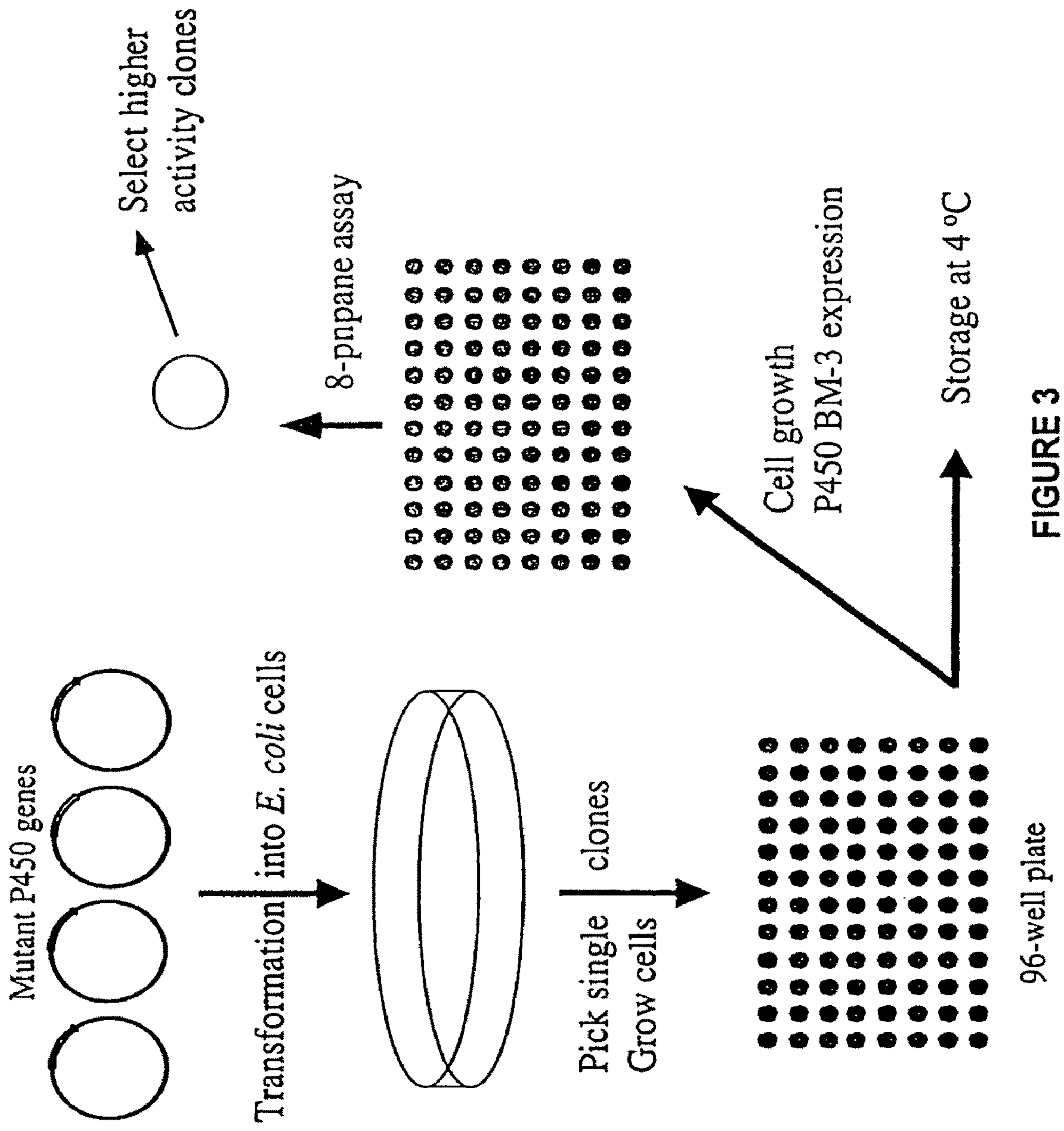
FIG. 3. P450 BM-3 screening procedure. Library of P450 BM-3 mutant genes is transformed into *E. coli* and plated on agar, from which single colonies are picked into 96-well plates and grown overnight. From these plates, samples are taken to inoculate fresh 96-well plates, in which the enzymes are expressed and assayed for hydroxylation activity. The plates from the overnight growth are stored at 4° C. and used to isolate active clones identified in the assay.

To improve the activity of P450 BM-3 or other cytochrome P450 enzymes towards alkanes by directed evolution, a rapid, reproducible screen that is sensitive to small changes (<2-fold) in activity is desirable (Arnold, 1998). Therefore, an alkane analog such as 8-pnpane (see FIG. 2 and Example 1), can be prepared that generates yellow color upon hydroxylation. This "surrogate" substrate with a C8 backbone and a p-nitrophenyl moiety is an analog of octane, and allows use of a colorimetric assay to conveniently screen large numbers of P450 BM-3 or other cytochrome P450 variants mutants for increased hydroxylation activity in microliter plates (Schwaneberg et al., 1999; Schwaneberg et al., 2001). Hydroxylation of 8-pnpane generates an unstable hemiacetal which dissociates to form (yellow) p-nitrophenolate and the corresponding aldehyde (FIG. 2). The hydroxylation kinetics of hundreds of mutants can then be monitored simultaneously in the wells of a microtiter plate using a plate reader (FIG. 3) (Schwaneberg et al., 2001). This method is particularly suitable for detecting P450 variant with improved alkane-oxidation activity.

To screen for improved solvent-resistance, in particular for P450 BM-3 variants, a substrate such as 12-pNCA can be added together with an organic co-solvent (e.g., tetrahydrofurane (THF), DMSO, ethanol, methanol, acetone, etc.) and 12-pNCA conversion initiated by adding a Isocitric co-factor regeneration solution (e.g., Isocitric acid 20 mM; $dH_2O$, NADP+3 mM, Isocitric dehydrogenase 0.8 U/ml). After visible color development, the reaction can be stopped by adding UT-buster (NaOH 1.5 M, 1.5 M Urea, 50% (v/v) DMSO), and absorption at 410 nm recorded.

Enzyme variants displaying improved levels of the desired activity or property in the screening assay(s) can then be expressed in higher amounts, retrieved, optionally purified, and further tested for the activity or property of interest.

Activity Assays

The cytochrome P450 variants created by directed evolution and selected for a desired property or activity can be further evaluated by any suitable test or tests known in the art to be useful to assess the property or activity. For example, the enzyme variants can be evaluated for their alkane-oxidation capability, alkene-oxidation capability, and/or organic-solvent resistance.

An assay for alkane-oxidation capability essentially comprises contacting the cytochrome P450 variant with a specific amount of alkane substrate, or a substrate which is an alkane analog such as 8-pnpane, in the presence of an oxygen donor, and any other components (e.g., NADPH) that are necessary or desirable to include in the reaction mixture, such as NADPH and buffering agents. After a sufficient incubation time, the amount of oxidation product formed, or, alternatively, the amount of intact non-oxidized substrate remaining, is estimated. For example, the amount of oxidation product and/or substrate could be evaluated chromatographically, e.g., by mass spectroscopy (MS) coupled to high-pressure liquid chromatography (HPLC) or gas chromatography (GC) columns, or spectrophotometrically, by measuring the absorbance of either compound at a suitable wavelength. By varying specific parameters in such assays, the Michaelis-Menten constant ($K_m$) and/or maximum catalytic rate ($V_{max}$) can be derived for each substrate as is well known in the art. Preferred substrates include, but are not limited to, methane, ethane, propane, butane, pentane, hexane, heptane, octane, and cyclohexane. In addition, in particular by HPLC and GC techniques, particularly when coupled to MS, can be used to determine not only the amount of oxidized product, but also the identity of the product. For example, octane can be oxidized to octanol where the hydroxyl group is positioned on any of the carbon atoms in the octanol molecule.

Alkene-oxidation can be evaluated by methods similar to those described for alkanes, simply by replacing an alkane with the corresponding alkene, and designing an assay which promotes and detects epoxide formation of the alkene. For example, an assay which detects NADPH consumption may be used. Preferred alkene substrates include ethene, propene, butene, pentene, hexene, heptene, and octene.

Organic solvent resistance of a cytochrome P450 variant is advantageously evaluated by conducting an oxidation reaction in the presence of a certain amount of organic solvent or co-solvent. This amount can be varied from, e.g., about 0.1% to about 99.9% (v/v) organic solvent or co-solvent, more preferably from about 0.5% to about 50% (v/v) organic solvent or co-solvent, and, most preferably, from about 1% to about 10% (v/v) organic solvent or co-solvent, of the total reaction volume. The amount of oxidation product is then detected as a measure of the organic-solvent resistance of the enzyme ,variant. Such assays can be conducted using various amounts of solvent or co-solvent, and on enzyme variants stored for various periods of time in solutions comprising a certain amount of organic solvent or co-solvent. Preferred organic co-solvents include THF, DMSO, acetone, acetonitrile, and ethanol.

P450 BM-3 Variants

Described herein are several mutations that have been identified to improve the alkane-oxidation activity and/or alkene-oxidation activity. Thus, a P450 BM-3 variant of the invention can comprise at least one of these mutations, optionally in combination with another mutations selected from the ones described in Table 1A, a mutation not described in Table 1A, or no other mutation. The variant P450 BM-3 enzymes of the invention can have a higher oxidation activity towards a saturated hydrocarbon, e.g., octane, hexane, cyclohexane, propane, ethane, and/or butane, than wild-type P450 BM-3. Preferred amino acid mutations are those listed in Table 1A. The skilled artisan could easily identify P450 BM-3 variants, including variants comprising truncated, deleted, and inserted amino acid sequences, that comprise one or more of these mutations and that show enhanced alkane-oxidation activity in a suitable assay as compared to wild-type P450 BM-3.

As identified in Example 3, the particularly active P450 BM-3 mutants IX139-3 and "J" comprised 11 and 10 amino acid mutations, respectively; V78A, H138Y, T175I, V178I, A184V, H236Q, E252G, R255S, A290V, A295T, and L353V for IX139-3; and V78A, T175I, A184V, F205C, S226R, H236Q, E252G, R255S, A290V, and L353V for "J". Using wildtype P450 BM-3 as the parent, a clone with approximately 2-fold increased activity for 8-pnpane was isolated. A single base mutation, threonine (T) to glycine (G), was found, which resulted in the amino substitution H236Q. Using H236Q as the parent for the 2nd generation, 9 mutants were identified in the 2nd generation with at least a 2-fold increase in ,activity. Recombining the 9 clones from the 2nd generation, a single clone was identified with 3 amino acid substitutions at V78A, H236Q, and E252G. These mutations, were noted as particularly effective mutations for improving alkane-oxidation activity, since these mutations were preserved throughout the evolutionary process. For example, H236Q was found in the first generation of mutants, and was preserved throughout the process, and the mutations V87A and E252G were discovered in the recombination of 9 clones from the $2^{nd}$ generation mutants, and thereafter preserved. Accordingly, a P450 BM-3 mutant comprising at least one, preferably at least two, and most preferably all three of these mutations, or a nucleic acid encoding such mutants, is a preferred embodiment of the invention.

In addition, the invention provides P450 BM-3 variants with a higher organic solvent resistance, especially towards water-miscible co-solvents such as DMSO and THF. A P450 BM-3 variant with improved organic solvent-resistance according to the invention comprises at least one of the mutations in Table 1A, optionally in combination with other mutations selected from the ones described in Table 1A, a mutation not described in Table 1 A, or no other mutation. As noted in Example 2, P450 BM-3 variants having particularly improved solvent resistance (F87A5F5 and W5F5) comprised R471A, E494K, and S1024E mutations, optionally with the mutation F87A. Accordingly, a P450 BM-3 mutant comprising at least one, preferably at least two, and most preferably all three of these mutations, with or without the F87A mutation, or a nucleic acid encoding such mutants, is a preferred embodiment of the invention. A skilled artisan could easily identify P450 BM-3 variants, including variants comprising truncated, deleted, and inserted amino acid sequences, that comprise one or more of the mutations in Table 1A and that show improved organic solvent-resistance in a suitable assay as compared to wild-type P450 BM-3.

Directed evolution techniques can thus significantly improve the organic solvent resistance of P450 BM-3 and its mutant P450 BM-3 F87A toward DMSO and THF, or any other organic solvents or co-solvents. It was also identified herein that position F87—located at the end of the substrate access channel directly above the heme—plays a size-dependent key role in modulating the monooxygenase activity in organic co-solvents. Because the mutations are located at the interface between the reductase domain and the P450 domain, it is believed, while not being limited to any theory, that the mutations create tighter domain bonding, which support electron transfer from the reductase to the heme in the presence of cosolvent.

Notably, except for mutation 1024 (which is not in the crystallized reductase fragment) all of the mutations improving organic solvent resistance are located at the interface between heme domain and reducase. It is therefore possible that the mutations "stabilize" the orientation of heme to reducase allowing an electron transfer from the reducase to the heme. Potentially, and without being bound to any theory, this electron-transfer could be essential, or at least important, for activity.

Preferably, the P450 BM-3 variants of the invention have an at least two-fold improvement in the capability to oxidize a chosen alkane (e.g., octane, hexane, pentane, butane, cyclohexane, or propane), and/or an at least two-fold improvement in the organic solvent-resistance, as compared to wild-type P450 BM-3. Even more preferably, the improvement for either or both of these properties is at least 3-fold, at least 4-fold, at least 5-fold, at least 10-fold, or at least 15-fold.

The P450 mutations of the present invention are wholly unexpected. For example, Schmid and coworkers recently described the engineering of P450 BM-3 to hydroxylate short chain (C8-C10) fatty acids not accepted by the wildtype enzyme (Li et al., 2001). Guided by the x-ray crystal structure, they focused on eight individual amino acids within the binding pocket to perform saturation mutagenesis. This approach successfully discovered mutations (Val26Thr, Arg47Phe, Ala74Gly, Leu188Lys, Phe87Ala) that altered the enzyme's substrate specificity. An indole-hydroxylating triple mutant of BM-3 (Phe87Val, Leu188Gln, Ala74Gly) was also shown to hydroxylate octane (Appel et al., 2001). Random mutagenesis, however, can discovery other, often subtle ways to modify activity. For example, sequencing the gene for the P450 BM-3 variants (Table 1) revealed that none of the more active mutants described herein contained any of the mutations found by Schmid and coworkers. Furthermore, the best mutants described here were considerably more active on octane than the triple mutant reported by Schmid and coworkers (Appel et al., 2001).

Attempts to engineer catalyst specificity are often limited to altering amino acids directly involved in substrate recognition and binding. Only one residue that is in direct contact with substrate in the wildtype enzyme has been mutated in IX139-3 (V78A). In fact, many of the mutations discovered herein were not found in the substrate binding channel, as suggested by the structure of P450 BM-3 with the bound fatty acid substrate. Some are in the hydrophobic core of the protein. Furthermore, several of the mutations are found in the F and G helices and the loop connecting them. This region undergoes the largest movements upon substrate binding (Li and Poulos, 1997). Mutations in this region may be responsible for new binding characteristics and activity for alkanes. How these particular substitutions enhance activity towards alkanes is not clear. They would have been very difficult to identify using currently available structure-based design methods. The cytotoxicity of the new variants indicates that enzymes showing such high alkane hydroxylation activity may not be produced by living cells under natural conditions and could only be generated by laboratory evolution strategies.

Non-P450 BM-3 Variants

As described above, the invention also provides for novel non-P450 BM-3 cytochrome P450 oxygenases in which one or more of the amino acid residues listed in Table 1A have been conserved. Conservation of an amino acid residue can show that the residue has an important function for the oxygenase activity and/or stability of the P450 enzyme. Thus, the P450 BM-3 mutations identified herein to improve alkane-oxidation activity and/or solvent resistance can simply be translated onto such non-P450 BM-3 enzymes to yield improved properties according to the invention.

Any method can be used to "translate" the P450 BM-3 mutation onto another cytochrome P450 enzyme, and such methods are well known in the art. For example, sequence alignment software such as SIM (alignment of two protein sequences), LALIGN (finds multiple matching subsegments in two sequences), Dotlet (a Java applet for sequence comparisons using the dot matrix method); CLUSTALW (available via the World Wide Web as freeware), ALIGN (at Genestream (IGH)), DIALIGN (multiple sequence alignment based on segment-to-segment comparison, at University of Bielefeld, Germany), Match-Box (at University of Namur, Belgium), MSA (at Washington University), Multalin (at INRA or at PBIL), MUSCA (multiple sequence alignment using pattern discovery, at IBM), and AMAS (Analyse Multiply Aligned Sequences). A person of skill can choose suitable settings, or simply use standard default settings, in these programs to align P450 BM-3 with another cytochrome P450 enzyme. See FIG. 20 for representative sequence alignments, and Table 2 for representative non-P450 BM-3 mutations.

Alternatively, such sequence alignments of P450 BM-3 with other cytochrome P450 enzymes can be taken from the literature, and amino acid residues corresponding to the mutated amino acid residues of the invention identified. For example, such information can be derived from de Montellano (1995) (see, especially, FIG. 1 on page 187).

While some P450 enzymes may not share significant sequence similarities, particular domains such as the heme-containing domains of P450s do display close structural similarity (Miles et al., 2000). Therefore, the positions of the various mutations described here could be translated to similar positions in different P450s having very low sequence similarity to P450 BM-3 using molecular modeling of those P450s based on sequence homology. Examples of using such techniques to model various P450s based on sequence homology with P450 BM-3 are available (Lewis et al., 1999). The same mutations described here, when placed in their corresponding positions in other P450 structures (as determined by modeling) would confer similar improvements in alkane-/alkene oxidation activity and organic solvent resistance.

In this regard, FIG. 21 shows a topological view of a cytochrome P450 enzyme, including the various domains of cytochrome P450 enzymes and the mutations contemplated by the present invention in each of those domains. While the topological view presented in FIG. 21 is that of $P450_{BM-P}$, with only minor modifications, this topology diagram may be used for other P450s. Briefly, FIG. 10 shows where mutations disclosed herein were made and these are summarized in Table 3 below.

TABLE 3

| Locations of Selected P450 BM-3 Mutations | |
|---|---|
| Domain | Amino Acid Residue |
| Heme domain: helix B' | V78 |
| Heme domain: loop connecting helices B' and C | F87 |
| Heme domain: β3-1 | H138 |
| Heme domain: helix F | T175 |
| Heme domain: helix F | V178 |
| Heme domain: helix F | A184 |
| Heme domain: helix F | N186 |
| Heme domain: helix G | D217 |
| Heme domain: helix G | S226 |
| Heme domain: helix H | H236 |
| Heme domain: helix I | E252 |
| Heme domain: helix I | R255 |
| Heme domain: helix J | A290 |
| Heme domain: helix J | A295 |
| Heme domain: β1-3 | L353 |
| Heme domain: loop connecting helices K' and L | G396 |
| — | R471 |
| Helix in flavin domain | E494 |
| — | S1024 |

Figure 10:
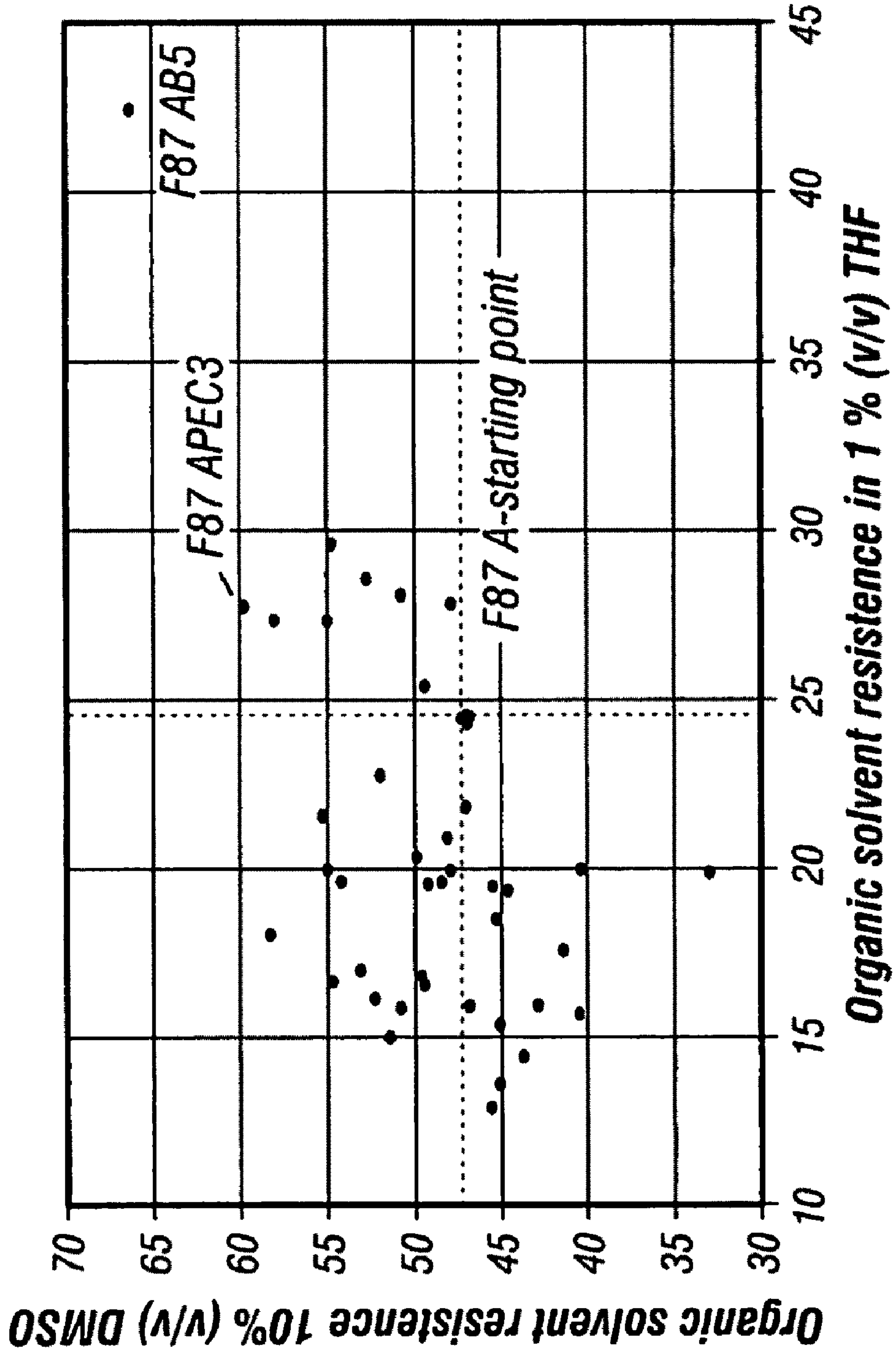
FIG. 10. Re-screen results of 1st mutant generation, investigating organic solvent resistance in 1% (v/v) (see Example 2).

Therefore, based on the topological view presented in FIG. 10, a P450 variant may be prepared by making one or more mutations in one or more of the domains of P450 identified in Table 3 above. Further, the topological view of FIG. 10 allows one to compare BM-3 variants with other P450 enzymes and identify those residues of non-BM-3 enzymes that could be mutated according to the secondary and tertiary structural motifs within the enzyme(s).

Thus, the invention provides novel non-P450 BM-3 cytochrome P450 oxygenases in which one or more of the amino acid residues listed in Table 1A have been conserved. Conservation of an amino acid residue can show that the residue has an important function for the oxygenase activity and/or stability of the P450 enzyme. The P450 BM-3 mutations identified herein to improve utilization of hydrogen peroxide as oxygen source and/or thermostability can simply be translated onto such non-P450 BM-3 enzymes to yield improved properties according to the invention.

Once the corresponding amino acid residues have been identified, a person of skill can test various mutations of these amino acid residues to identify those that yield improved alkane-oxidation capability or improved organic solvent-resistance as compared to the cytochrome P450 wild-type enzyme. Preferred amino acid substitutions are those that correspond to a substitution listed in Table 1A for P450 BM-3 mutations.

EXAMPLES

The invention is illustrated in the following examples, which are provided by way of illustration and are not intended to be limiting.

Example 1

Directed Evolution of a Cytochrome P450 Monooxygenase for Alkane Oxidation

This Example describes the discovery of P450 BM-3 variants. P450 BM-3 variants were created and identified by directed evolution techniques, specifically iterative cycles of random mutagenesis and recombination, and functional screening.

All chemical reagents were procured from Aldrich, Sigma, or Fluka. Enzymes were purchased from New England Biolabs, Stratagene, and Boehringer Mannheim. The 1H NMR spectrum was recorded on a Varian 300 MHz nuclear magnetic resonance spectrometer with a Mercury console. Quantitative Technologies Inc. (Whitehouse, N.J.) performed elemental analysis.

A. Random Library Generation and Screening of P450 BM-3

P450 BM-3 modified to contain a His6 tag was amplified from pT-USC1 BM-3 (Schwaneberg et al., Anal Biochem 1999a, 269:359-366) by PCR techniques using a proofreading polymerase Pfu to introduce a BamHI upstream of the start codon and an EcoRI site immediately downstream from the stop codon. The two oligonucleotides used were as follows:

```
                    (BamHI site underlined, SEQ ID NO: 7)
5'-CGCGGATCCATCGATGCTTAGGAGGTCATATGACAATTAAAGAA
ATGCCTC-3'

                     (EcoRI site underline, SEQ ID NO: 8)
5'-CCGGAATTCTTAATGATGATGATGATGATGCCCAGCCCACACGTC
TTTTGC-3'
```

The PCR product was digested with BamHI and EcoRI. The P450 BM-3 gene was ligated into expression vector pCWOri (+) (Barnes, 1996) (p BM-3 WT18-6), which is under the control of double Ptac promoter and contains an ampicillin resistance coding region. A silent mutation was introduced to construct a SacI site 130 bases upstream of the end of the herne domain. The QuikChange (Stratagene) protocol was followed and the primers were as follows:

```
                     (SacI site underlined; SEQ ID NO: 9)
5'-CATACAAACTACGAGCTCGATATTAAAGAAAC-3'

                    (SacI site underlined; SEQ ID NO: 10)
5'-GTTTCTTTAATATCGAGCTCGTAGTTTGTATG-3'
```

Synthesis of p-nitrophenoxvoctane (8 pnpane)

1-bromooctane (1 g, 5.18 mmole) and 4-nitrophenol, sodium salt (0.92 g, 5.71 mmole) were refluxed in DMSO (30 ml) at 120° C. for 5 hours. The DMSO was distilled off to near dryness. The resulting brown residue was loaded onto a silica column and eluted with 10:1 mixture of petroleum ether and diethylether. The yield was 30%. 1H NMR ($CDCl_3$, peaks at =8.18 (m, 2H), 6.93 (m, 2H), 4.04 (t, 2H), 1.81 (p, 2H), 1.33 (m, 10H), 0.89 (t, 3H)). Elemental analysis calculated for $C_{14}H_{21}O_3N$: C, 66.91; H, 8.42; N, 5.57. Found: C, 66.97; H, 8.34; N, 5.52.

Expression and Purification of P450 BM-3 Variants

The P450 BM-3 gene, which includes a silent mutation to introduce a SacI site 130 by upstream of the end of the heme domain, was cloned behind the double tac promoter of the expression vector pCWori (p BM-3_WT18 6) (Farinas et al., 2001). This plasmid was used for production of wildtype protein and as a starting clone for directed evolution. For protein production, Terrific Broth (TB) media (500 ml) supplemented with trace elements (125 μL: 0.5 g $MgCl_2$, 30.0 g $FeCl_2$ $6H_2O$, 1.0 g $ZnCl_2$ $4H_2O$, 0.2 g $CoCl_2$ 6H2O, 1.0 g $NaMoO_4$ $2H_2O$, 0.5 g $CaCl_2$ $2H_2O$, 1.0 g $CuCl_2$ and 0.2 g $H_2BO_3$ in 1L HCl solution (90% v/v distilled water: concentrated HCl)) (Joe et al., 1999) was inoculated with 500 μl of an overnight culture of *E. coli* BL21 containing the expression plasmid. After shaking for 10 hours at 35° C. and 250 rpm,. aminolevulinic acid hydrochloride (ALA) (0.5 mM) was added, and expression was induced by addition of IPTG (1mM) and cells were harvested by centrifugation after a total cultivation time of 30 hours.

After 30 hours, the cells were harvested by centrifugation and the supernatants discarded. The pellets were washed with Tris HCl (15 ml, pH 8.3). Cells were resuspended in Tris HCl (15 ml, pH 8.3), sonicated (2×45 sec; output control=7, duty cycle 40%; Sonicator, Heat Systems Ultrasonic, Inc.) and centrifuged. The supernatants were further cleared through a 0.45 μM filter. The filtrate was diluted 15 mL water and purified by published procedures (Farinas 2001). P450 BM-3 concentrations were measured from the CO difference spectra (Omura 1963).

Library Construction

For the first 2 generations, mutagenic PCR was performed on the heme domain in a 100 mL reaction as described in Zhao et al. (1999) with some modifications. The mutated P450 BM 3 fragment was 1291 base pairs. The reaction contained $MgCl_2$ (7 mM) and the following forward and reverse primers (40 pmol each):

```
                             (Forward, SEQ ID NO: 11)
5' ACAGGATCCATCGATGCTTAGGAGGTCATATG 3'

                             (Reverse, SEQ ID NO: 12)
5' GTGAAGGAATACCGCCAAG 3'.
```

The reaction also contained p BM-3 WT18-6 (10 ng), dNTPs (0.2 mM dGTP, 0.2 mM dATP, 1 mM dCTP, 1 mM dTTP), and Taq polymerase (5 units, Roche), KCl (50 mM), and Tris-HCl (10 mM, pH 8.3, 20° C.). MnCl2 (0.0, 0.05, and 0.1 mM) was added to the PCR mixture to alter the error rate of the polymerase. PCR was performed in a thermocycler (PTC200, MJ Research, Waltham, Mass.) for 30 cycles (95° C., 45 s; 50° C., 30 s; 72° C., 2 min). The PCR product was restricted with BamHI and Sad and ligated into expression vector pCWOri (+). The resulting plasmid was transformed into *E. coli* strain DH5α and the colonies were selected on agar plates containing ampicillin (100 mg/ml).

For the $3^{rd}$ generation, 9 mutants from the $2^{nd}$ generation showing at least 2-fold improved activity on 8-pnpane were recombined by staggered extension process (StEP) (Zhao HM, et al. Nature Biotechnol 1998; 16:258 261). Recombination was done in 50 μL reactions as described (Zhao et al., 1999). Each reaction contained buffer (Qiagen 1× PCR buffer), template (10 ng each), forward and reverse primer (final 0.15 mM), dNTPs (200 μM each) and Taq DNA polymerase (2.5 units, Qiagen). PCR was performed in a thermocycler (PTC200, MJ Research, Waltham, Mass.) (1. 95° C., 2 min; 2. 95° C. 30 s; 3. 50° C., 10 s; repeat steps 2 and 3 100×). The PCR product was restricted with BamHI and SacI and ligated into expression vector pCWOri (+). The resulting plasmid was transformed into *E. coli* strain DH5α and the colonies were selected on agar plates containing ampicillin (100 mg/ml).

For the $4^{th}$ and $5^{th}$ generation, error prone PCR was also performed using the GeneMorph PCR Mutagenesis Kit (Stratagene) applying conditions of high error rate (1-10 ng template DNA). The PCR product was restricted with BamHI and SacI and ligated into expression vector pCWOri (+). The resulting plasmid was transformed into *E. coli* strain DH5α and the colonies were selected on agar plates containing ampicillin (100 mg/ml).

Recombination was done in 50 mL reactions as described (Zhao et al., 1999). Each reaction contained buffer (Qiagen 1× PCR buffer), template (10 ng each), forward and reverse primer (final 0.15 mM), dNTPs (200 μM each) and Taq DNA polymerase (2.5 units, Qiagen). PCR was performed in a thermocycler (PTC200, MJ Research, Waltham, Mass.) (1. 95° C., 2 min; 2. 95° C. 30 s; 3. 50° C., 10 s; repeat steps 2 and 3 100×).

Screening for Hydroxylation Activity

Cultivation and Expression of P450 BM-3 Mutant Libraries

For the first three rounds of evolution, a robot (Qpix, Genetix) picked and inoculated colonies into 1 ml deep-well plates containing LB media (400 ml) and ampicillin (100 mg/ml). The plates were incubated at 37° C., 270 RPM, and 80% relative humidity. After 24 hours, the culture liquid (50 ml) was added to TB (450 ml) containing, ampicillin (100 mg ampicillin/ml), thiamine (5 mg/ml), and trace elements (0.25 ml/ml). After growth at 37° C. for 1 hour, -aminolevulinic acid hydrochloride (1 mM) and isopropyl—thiogalactopyranoside (1 mM) was added. The temperature was shifted to 30° C. and the cultures were grown for 24 hours.

For the $4^{th}$ and $5^{th}$ generations the screening procedure was modified to the following procedure. The plates with the picked colonies were incubated in LB (containing 100 μg/L ampicillin) at 30° C., 270 RPM, and 80% relative humidity. After 24 hours, TB (500 ml) containing, ampicillin (100 mg ampicillin/ml), thiamine (5 mg/ml), and trace elements (0.25 ml/ml), δ-aminolevulinic acid hydrochloride (1 mM) and 10 μM isopropyl-thiogalactopyranoside, was inoculated with the preculture using a 96 inoculation pin and grown for 24 hours.

Preparation of Cell Lysates

For the first three generations, the plates were centrifuged and supernatants were discarded. Cell pellets were washed with Tris-HCl (350 ml, pH 8.3), frozen at −20° C. for at least 8 hours and then resuspended in 400 μl Tris-HCl (350 ml, pH 8.3) containing lysozyme (0.5 mg/ml), deoxyribonuclease I (0.1 mg/ml) and $MgCl_2$ (10 mM). After incubation at 37° C. for 45 minutes, the plates were centrifuged and the lysate (150 ml) was transferred to a 96-well plate. For the final generations, the frozen cell pellets were resuspended in phosphate buffer (1 mL, 0.1 M, pH 8.0) containing lysozyme (0.5 mg/mL0, DnaseI (0.1 μL/mL) and $MgCl_2$ (10 mM). The lysates were centrifuged and the supernatants were diluted for activity measurements in 96 well microtiter plates.

High Throughput Determination of Enzymatic Activity

For the first three generations, 8-pnpane (150 μM) in DMSO (1%) was added to the lysate and incubated at room temperature. After 5 minutes, NADPH (1 mM) was added and the absorbance at 410 nm was measured with a microplate spectrophotometer (SPECTRAmax, Molecular Devices).

For the final generations, mutant libraries were screened using 8-pnpane as described above. Also, a cofactor (NADPH) depletion assay was used to determine the turnover rates. The lysates were diluted into 96 well microtiter plates containing phosphate buffer (200 μL, 0.1 M, pH 8.0), alkane substrate (0.5-1.0 mM), and DMSO (1%). The liquid alkanes were added to the buffer using alkane stock solutions in DMSO, whereas gaseous alkanes were bubbled into buffer for ~45 minutes to obtain saturated solutions. The reaction was initiated by addition of NADPH (200 μM), and the oxidation of NADPH was monitored at 340 nm. Only the mutants active in both screens were isolated and recharacterized.

Rescreening

The most active clones from the primary screen were streaked out on agar plates to get single colonies. Four to 8 single colonies were recultured in deep well plates and rescreened as described above. In the rescreen all clones were also assayed for hydroxylation of the target substrate octane. The same dilutions of lysates in buffer were used as in the 8-pnpane assay. A stock octane substrate solution (225 μM) in DMSO (1%) was added to-the lysates. After addition of NADPH (0.75 mM), in the same buffer as used for the lysates, the oxidation of NADPH to $NADP^+$ was followed using the microplate spectrophotometer for 3 min at 340 nm. As a control the same assays were performed without addition of the alkane substrate to verify that NADPH consumption was coupled to the presence of substrate.

For propane oxidation, the cells were already lysed in a buffer, where the 0.1 M Tris-HCl from the lysis buffer described above was replaced by 30 mM phosphate buffer pH 7.4 to avoid organic substances (which could conceivably become substrates for the enzyme) in the buffer. Phosphate buffer was saturated with propane by bubbling propane into the buffer for 1 hour. Thirty μl of the bacterial lysates were pipeted into 96 well microtiter plates and 120 μl of the propane saturated buffer were added. The reaction was started again by addition of 50 μl of 3 mM NADPH and followed at 340 nm for 3 min.

Agar Plate Colony Development

Cells were grown on LB agar plates containing 100 μg/ml ampicillin, 1 mM aminolevulinic acid hydrochloride and 10 μM isopropyl thiogalactopyranoside. The latter two substances are not necessary if the activity resulting from a leaky promoter system is high enough. A substrate solution was prepared containing 30 mM phosphate buffer pH 7.4, 100 μM polymyxin B sulfate as a cell permeabilizer, 2 mM NADPH and 5 mM alkane substrate. The substrate solution was sonicated before use to emulsify most of the substrate in the buffer system.

A nitrocellulose membrane was soaked with this substrate solution and placed on the colonies on the agar plate. The optimal reaction time was estimated by testing the assay on control agar plates with colonies of clones with different hydroxylation activity before starting the main screen. After the reaction time the color reagent (0.5 mg/ml NBT in 30 mM phosphate buffer pH 7.4 and some crystals of the catalyst PMS) was pipeted directly onto the nitrocellulose membrane. Colonies located under white spots on the membrane were picked with a toothpick and streaked out on fresh agar plates to get single colonies for the re-screen.

Determination of the Maximum Initial Rates for Hydroxylation

The enzymes were purified and quantified as described above. First, the substrate concentration corresponding to the maximum turnover rate was determined by monitoring NADPH consumption with a plate reader in the presence of enzyme in phosphate buffer (0.1 M pH 8.0) and varying amounts of substrate in methanol (1%). After identifying the concentration of substrate that coincides with the maximum rate, the rate was measured using an UV-Vis spectrophotometer and 1 cm path length quartz cuvettes. A typical reaction solution contained enzyme (700 μL, 0.35-3.5 μM) in potassium phosphate buffer (0.1 M, pH 8.0) and substrate in methanol (1%). The reaction was initiated by the addition of NADPH (300 μL, 200 μM), and the absorption at 340 nm was monitored.

The amount of $H_2O_2$ was determined using 2,2'-azino-di-[3-ethyl-benzothiazidine-6-sulfonic acid/horseradish peroxidase assay by following published procedures (Yeom, H. & Sligar, S. G. Oxygen activation by cytochrome P450BM-3: effects of mutating an active site acidic residue. Arch Biochem Biophys 337, 209-216. (1997).

B. Wild-Type P450 BM-3 Alkane Oxidation Assay

Octane Oxidation by P450 BM-3

The enzymes were purified and quantified as described above. The oxidation was performed with solutions containing octane in DMSO (1 mM octane; 1% DMSO), P450 BM-3 (2-3 μM), and NADPH (1-5 mM) in Tris-HCl (50 mM) containing NaCl (340 mM). A concentrated solution of octane in DMSO was added to the enzyme. The resulting solution was incubated for 30 minutes at room temperature. Octane oxidation was initiated by the addition of NADPH in aqueous solution. After a specific time, the solution was extracted three times with of $CH_2Cl_2$ (333 mL) containing decanol (1 mM) as an internal standard. The organic layer was dried over anhydrous Na2SO4, and the products were analyzed by GC/MS.

Catalytic activity of P450 BM-3 was measured spectrophotometrically by monitoring the rate of NADPH oxidation, as described (Matson et al. (1977). The assay solution contained 0.1 nmole P450 BM-3, octane in DMSO, and 0.8 mM NADPH, 50 mM NaCl in 0.1 M Tris-HCl, pH 8.2.

Production of $H_2O_2$ during the hydroxylation reaction was determined using the iron(III) thiocyanate assay (Fruetel et al., 1994). $1.0\times10^{-9}$ mole P450 BM-3 was incubated with $1.0\times10^{-6}$ mole octane for 5 minutes. The reaction was initiated by addition of $2.5\times10^{-7}$ mole NADPH to the enzyme solution. Every 2 minutes a 0.2 ml aliquot from the reaction was added to 1.0 ml aqueous iron(II) solution (5.0 grams $FeSO_4(NH_4)_2\times6H_2O$, 45.0 ml degassed $H_2O$, 5 ml concentrated $H_2SO_4$). Subsequently, 0.4 ml of a 10% aqueous solution of KSCN was added to the solution, and the absorbance was measured at 480 nm.

C. Assay for 1X139-3 Catalytic Activity with Alkanes

Determination of the Maximum Initial Rates for Liquid Alkane Hydroxylation by 1X139-3

The enzymes were purified and quantified as described above. First, the substrate concentration corresponding to the maximum turnover rate was determined by monitoring NADPH consumption with a plate reader in the presence of enzyme in phosphate buffer (0.1 M pH 8.0) and varying amounts of substrate in methanol (1%). After identifying the concentration of substrate that coincides with the maximum rate, the rate was measured using an UV-Vis spectrophotometer and 1 cm path length quartz cuvettes. A typical reaction solution contained enzyme (700 μL, 0.35-3.5 μM) in potassium phosphate buffer (0.1 M, pH 8.0) and substrate methanol (1%). The reaction was initiated by the addition of NADPH (300 μL, 200 μM), and the absorption at 340 nm was monitored. The substrates examined were pentane, hexane, cyclohexane, and octane.

The amount of $H_2O_2$ was determined using 2,2'-azino-dit3-ethyl-benzothiazidine-6-sulfonic acid/horseradish peroxidase assay by following published procedures (Yeom & Sligar, 1997).

Determination of the Maximum Initial Rate for Gaseous Alkane Hydroxylation by IX IX139-3

Potassium phosphate buffer (0.1 M, pH 8.0) was saturated with the gaseous alkane (propane or butane) by bubbling the substrate into the solution for 1 hour. A typical reaction contained alkane saturated buffer (700 μL) and enzyme (0.5 μM). Addition of NADPH (300 μL, 200 μM) in buffer initiated the reaction, and the rate of NADPH oxidation was follow at 340 nm.

GC/MS Analysis

Biocatalytic oxidations were performed under oxygen limited conditions in sealed vials. For octane, hexane, or cyclohexane conversions, the solution contained alkane (1 mM) in DMSO (1% DMSO) and enzyme (1 μM) in potassium phosphate buffer (100 mM, pH 8.0). The solution was stirred at room temperature for 5 minutes, and the reaction was initiated by the addition of NADPH (1 mM).

Reactions with gaseous alkanes were carried out in a sealed 20 mL vial containing enzyme (1.0 μM) in potassium phosphate buffer (5 mL, 100 mM, pH 8.0). The headspace was filled with either propane or butane. The reaction was initiated with the addition of NADPH (1 mM). The reaction mixture was analyzed directly by GC/MS using an Hewlett Packard 5890 Series II gas chromatograph coupled with an Hewlett Packard 5972 Series Mass Selective Detector. The GC was fitted with HP FFAP column (crosslinked FFAP, 30 m×0.25 mm×0.25 mm film thickness). The condition for octane is as follows: Isothermic at 120° C. for 6 minutes. The condition for hexane and cyclohexane: (1) 100° C. for 5 minutes to 50° C. (2) 100° C. to 200° C. at 2,° C./min. (3) Lsothermic at 200° C. for 2 minutes. The condition for propane and butane: (1) 30° C. for 3 minutes. (2) 30° C. to 150° C. at 20° C./min. Authentic standards were used to identify the products by retention time. Products were further verified by matching the fragmentation distributions with a database in the software provided with the instrument manufacturer.

Initially for octane oxidation by wildtype, the products were identified with GC/MS using a Hewlett Packard 5890 Series II gas chromatograph coupled with a Hewlett Packard 5989A mass spectrometer. The GC was fitted with an HP 1 column (crosslinked methyl silicone gum, 12 m×0.2 mm×0.33 mm). The temperature gradient is as follows: 1) 40 to 50° C. at 15° C., 2) 50 to 75° C. at 10° C./min, 3) 75 to 160° C./min. Authentic standards were used to identify retention times of the products. The products were further verified by matching the fragmentation distributions with a database in the software provided by the instrument manufacturer.

D. Results

Wildtype P450 BM-3 is Active Towards Octane

In the presence of purified P450 BM-3 and NADPH, octane was consumed within 2 hr and gave several products detectable by GC/MS (FIG. 1). The total yield of product detected was about 50%, with alcohols accounting for about 90% of the product and ketones representing 10%. The major hydroxylated products were 4-octanol, 3-octanol, and 2-octanol. 1-Octanol was not detected under the experimental conditions applied. The product ratio was, approximately, 8:9:1; 4-octanol: 3-octanol: 2-octanol. 4-Octanone and 3-octanone were also present in the product mixture. A possible mechanism for the formation of the ketones is hydroxylation of the alcohol to generate a gem-diol which dehydrates to the corresponding ketone (Boddupalli et al., 1992; March, 1992a). Another possible mechanism is via the pinacol rearrangement (March, 1992b). However, it is also possible that traces of protein impurities were responsible for this oxidation, and further tests were therefore performed to validate the results.

It was tested whether P450 BM-3 catalyzes the oxidation of 3-octanol to 3-octanone. Upon addition of NADPH to a solution of P450 BM-3 and 3-octanol, a peak at 3.7 min appeared. This peak had the same retention time as an authentic sample of 3-octanone. Furthermore, the fragmentation pattern of the peak matched that of 3-octanone found in the mass spectrum database. Solutions containing only P450 BM-3 and 3-octanol, but no NADPH, do not produce any detectable 3-octanone. Similar results were obtained with 4-octanol as the substrate.

The activity of P450 BM-3 towards octane was measured spectrophotometrically by monitoring the rate of NADPH consumption. The following results were obtained: $k_{cat}$=0.7 $s^{-1}$, $K_m$=2.0×$10^{-5}$ M and $k_{cat}/K_m$=3.5×$10^4$ $M^{-1}s^{-1}$. Thus, on octane, the P450 BM-3 enzyme has a kcat 120-fold less and a Km that is 15 times larger (kcat/Km~2000 times less) than on its preferred C16 fatty acid substrate.

P450 BM-3 Catalyzes Hydroxylation of Octane without Uncoupling

Hydrogen peroxide production during catalysis by P450 BM-3 was also monitored in order to determine whether the rate of NADPH oxidation was affected by uncoupling (Oliver et al., 1997; Fruetel et al., 1994). $H_2O_2$ was not detected under the experimental conditions, which indicates that the P450 catalyzes the hydroxylation of octane without significant uncoupling. This was consistent with previous reports that indicated efficient coupling for P450 BM-3 acting on unnatural substrates such as styrene or alkyl trimethylammonium compounds (Oliver et al., 1997; Fruetel et al., 1994).

Directed Evolution Improves the Activity of Cytochrome P450 BM-3 Towards Octane and Other Substrates Mutant library construction was focused on the P450 BM-3 heme domain, which contains the substrate binding site and the monooxygenase activity. The libraries were generated by error prone PCR (Zhao et al., 1999), using $MnCl_2$ concentrations of 0.0, 0.05, and 0.1 mM, which yielded 70, 60, and 50% active transformants, respectively. The library generated with no added $MnCl_2$, corresponding to about 2 base changes per gene (0.15% error rate), was chosen for screening (Zhao et al., 1999).

Two thousand clones of the first generation library were screened and 23 of the most active clones were selected for further analysis. Since the screen was sensitive to total activity, which includes increased expression as well as changes in specific activity, enzyme concentrations were estimated from the CO difference spectra for binding to the reduced P450

Figure 4:
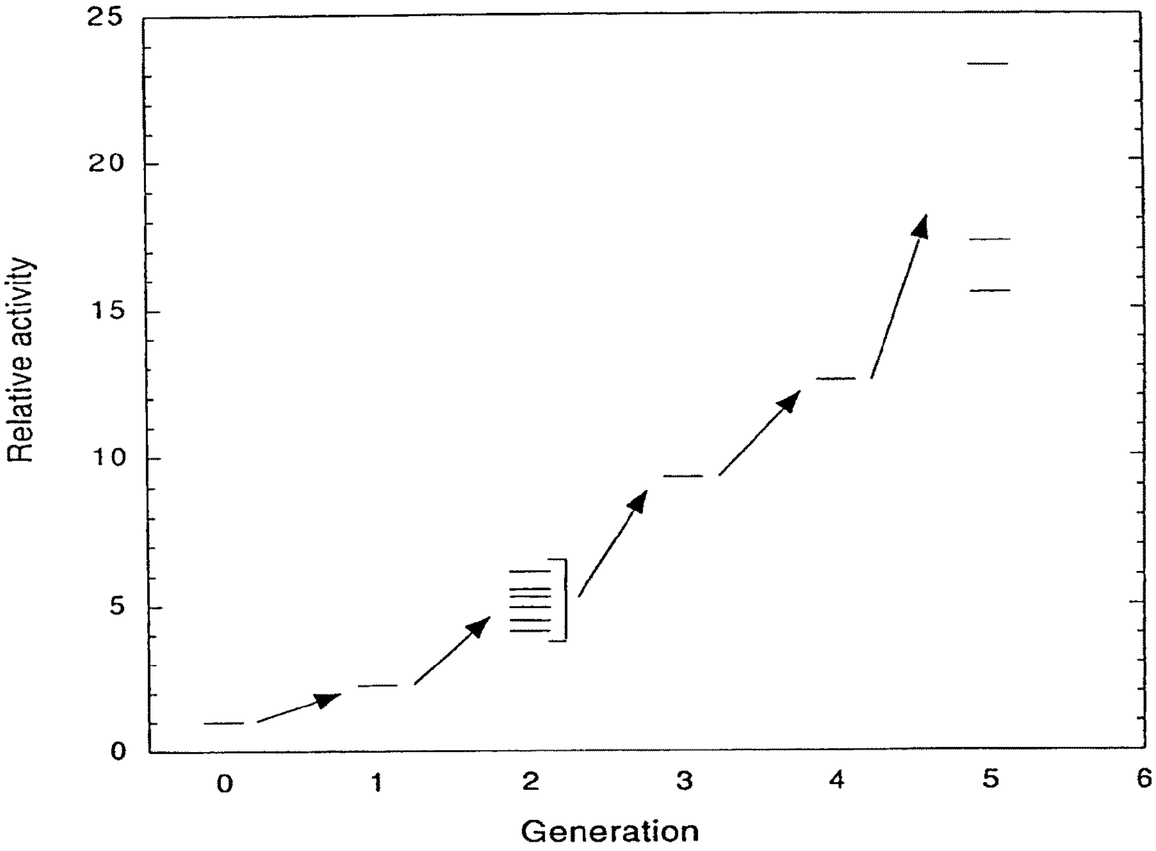
FIG. 4. Progression of activity for P450 BM-3, as measured on 8-pnpane.

BM-3 in order to calculate specific activities (Omura and Sato, 1964). The best variant, VIII118 2C9, displayed approximately twice the specific activity of the wildtype enzyme (FIG. 4).

The $2^{nd}$ generation library was also created with error-prone PCR using VIII118 2C9 as the template, and 9 mutants were isolated that were between 1.8 and 2.5 times more active than VIII118 2C9. IX18_18 was found to be 2.38 times more active than VIII118 2C9, and it was used for comparison for the $3^{rd}$ generation library.

The $3^{rd}$ generation was produced by StEP recombination (Zhao et al., 1999), using 9 variants from the $2^{nd}$ generation, and the most active mutant (1X35_4) was found to be 1.74 times more active than IX118_18. IX35_4 was used for comparison for the $4^{th}$ generation.

The $4^{th}$ generation was constructed by error-prone PCR using the IX35_4 as the template. The GeneMorph PCR Mutagenesis Kit (Stratagene) was used to create the libraries. The most active variant (IX 79_1) was 1.35 times as active compared to IX35_4. IX79_1 was used for comparison for the $5^{th}$ generation library.

After some generations the evolved P450 BM-3 variants began showing high cytotoxicity. This caused large differences between the activities measured in the high throughput screen and then again after normalization to CO binding. As a result, the improvements in activity became smaller in generation 4, which might indicate that there is a "plateau", i.e., a rather low limit to the activity which is possible for a P450 BM-3 variant created by this approach alone.

Even in the case of the strongly regulated promoter used in this study, there is always some leakiness of the promoter. Even small amounts of toxic proteins produced by the leaky promoter could cause large (negative) physiological effects on the different clones during growth in the 96 deep well plates. Therefore, the screening procedure was redesigned after generation four, as described under "Materials and Methods."

The $5^{th}$ generation was produced using IX79_1 as the template. Again, Genemorph was used to create the libraries. Using a modified screening procedure in generation five resulted in highly improved variants for alkane hydroxylation. The best three clones are between 1.24-1.86 times more active than IX79_1. The best clone from the $5^{th}$ generation (IX139-3) was 23 times more active than wildtype. The same library of the $5^{th}$ generation was used for a second screen using mutant IX139-3 for comparison.

Selected clones, including the three best clones from the first screen (IX139-3, IX139-37 and IX139-43), were recombined by StEP to produce the library of the $6^{th}$ generation. Several hundred clones of this new library have been analyzed using the microtiter plate assays, and results indicate further improvement of the alkane hydroxylating activity. For example, the mutant "J" (V78A, T175I, A184V, F205C, S226R, H236Q, E252G, R255S, A290V, and L353V) was shown to be 2.0 and 1.6 fold more active for NADPH consumption for propane and butane, respectively.

All improved clones found in the primary screen were rescreened for NADPH consumption by hydroxylation of octane. Only clones showing improved activity in presence of octane and a low background without octane were selected as templates for new generations. This gave some certainty that this was the right track for optimizing alkane hydroxylation activity. An assay for propane hydroxylation was included in the screening program in the sixth generation. The mutations, and the amino acid substitutions they lead to in the evolved P450 BM-3 enzymes, are listed below (Table 4).

TABLE 4

Selected Cytochrome P450 Mutants Created By Directed Evolution
Mutations were verified by sequencing one strand of DNA.

| Generation | Clone | Amino Acid Mutation | Codon Mutation |
|---|---|---|---|
| Wild-type | viii18_6 | | |
| 1st Gen., ep PCR, taq | viii118 2C9 | His236Gln | CAT→CAG |
| 2nd Gen., ep PCR, taq | viii159 7A4 | Met30Ile | ATG→ATT |
| | | Asp232Gly | GAT→GGT |
| | | His236Gln | CAT→CAG |
| | | Met416Leu | ATG→TTG |
| | viii159 7G4 | Glu64Ala | GAA→GCA |
| | | Ile220Thr | ATT→ACT |
| | | His236Gln | CAT→CAG |
| | | Thr411Ala | ACG→GCG |
| | viii159 10A6 | Val78Ala | GTA→GCA |
| | | Phe162Ser | TTT→TCT |
| | | Lys224Ile | AAA→ATA |
| | | His236Gln | CAT→CAG |
| | | Lys306Glu | AAA→GAA |
| | viii159 10A11 | Thr10? | ACG→NCG |
| | | Glu13? | GAG→GNG |
| | | Met118Leu | ATG→TTG |
| | | Gly154Gly* | GGT→GGA |
| | | His236Gln | CAT→CAG |
| | viii159 12A5 | His236Gln | CAT→CAG |
| | | Ile258Thr | ATT→ACT |
| | ix18_12 | Pro45Pro* | CCT→CC(T/C) |
| | | His171Gln | CAT→CAG |
| | | His236Gln | CAT→CAG |
| | | Asp370Glu | GAT→GAA |
| | ix18_18 | Gln73Gln* | CAA→CAG |
| | | His236Gln | CAT→CAG |
| | | Ile259Val | ATT→GTT |
| | | Leu272Leu* | CTT→CTC |
| | | Lys289Lys* | AAA→AAG |
| | | Glu380Gly | GAA→GGA |
| | ix18_34A | Lys187Glu | AAG→GAG |
| | | His236Gln | CAT→CAG |
| | ix18_38 | Lys59Lys* | AAA→AAG |
| | | Lys97Lys* | AAA→AAG |
| | | His236Gln | CAT→CAG |
| | | Glu252Gly | GAG→GGG |
| | | Lys289Lys* | AAA→AAG |
| 3rd gen, step | ix35_4 | Val78Ala | GTA→GCA |
| | | His236Gln | CAT→CAG |
| | | Glu252Gly | GAG→GGG |
| 4th gen, genemorph | ix79_1 | Val78Ala | GTA→GCA |
| | | Phe107Phe* | TTC→TTT |
| | | Thr175Ile | ACA→ATA |
| | | Ala184Val | GCA→GTA |
| | | His236Gln | CAT→CAG |
| | | Glu252Gly | GAG→GGG |
| | | Ala290Val | GCA→GTA |
| | | Leu353Val | CTA→GTA |
| 5th gen, genmorph | ix139-3 | Val78Ala | GTA→GCA |
| | | Phe107Phe* | TTC→TTT |
| | | His138Tyr | CAT→TAT |
| | | Thr175Ile | ACA→ATA |
| | | Val178Ile | GTC→ATC |
| | | Ala184Val | GCA→GTA |
| | | His236Gln | CAT→CAG |
| | | Glu252Gly | GAG→GGG |
| | | Arg255Ser | CGC→AGC |
| | | Ala290Val | GCA→GTA |
| | | Ala295Thr | GCA→ACA |
| | | Leu353Val | CTA→GTA |
| | | Gln397Gln* | CAG→CAA |
| | ix139-37 | Val78Ala | GTA→GCA |
| | | Phe107Phe* | TTC→TTT |
| | | Asn159Asn* | AAC→AAT |
| | | Thr175Ile | ACA→ATA |
| | | Ala184Val | GCA→GTA |
| | | Asn186Asp | AAC→GAC |
| | | Arg203Arg* | CGC→CGT |
| | | Asp217Val | GAT→GTT |
| | | His236Gln | CAT→CAG |
| | | Glu252Gly | GAG→GGG |
| | | Ala290Val | GCA→GTA |

TABLE 4-continued

Selected Cytochrome P450 Mutants Created By Directed Evolution
Mutations were verified by sequencing one strand of DNA.

| Generation | Clone | Amino Acid Mutation | Codon Mutation |
|---|---|---|---|
| | | Leu353Val | CTA→GTA |
| | | Gly396Met | GGT→AGT |
| | | Thr427Thr* | ACA→ACT |
| | ix139_43 | Glu4Glu* | GAA→GAG |
| | | Val78Ala | GTA→GCA |
| | | Phe107Phe* | TTC→TTT |
| | | Thr175Ile | ACA→ATA |
| | | Ala184Val | GCA→GTA |
| | | Ser226Ile | AGC→ATC |
| | | His236Gln | CAT→CAG |
| | | Glu252Gly | GAG→GGG |
| | | His266His* | CAC→CAT |
| | | Ala290Val | GCA→GTA |
| | | Leu353Val | CTA→GTA |

*Silent mutation
"N": Nucleotide is unclear
"?": Amino acid is unclear

Evolved P450 BM-3 Variants Hydroxylate Various Substrates

The chosen screen was sensitive to hydroxylation of the methylene adjacent to the oxygen atom of the surrogate the p-nitrophenoxyoctane substrate. Activity towards octane, hexane, and cyclohexane was therefore measured, by measuring the rate of NADPH oxidation, which was assumed to be fully coupled to alkane oxidation. As a result, relative activities determined using NADPH oxidation were assumed to equal the relative activities on the different substrates.

Figure 5:
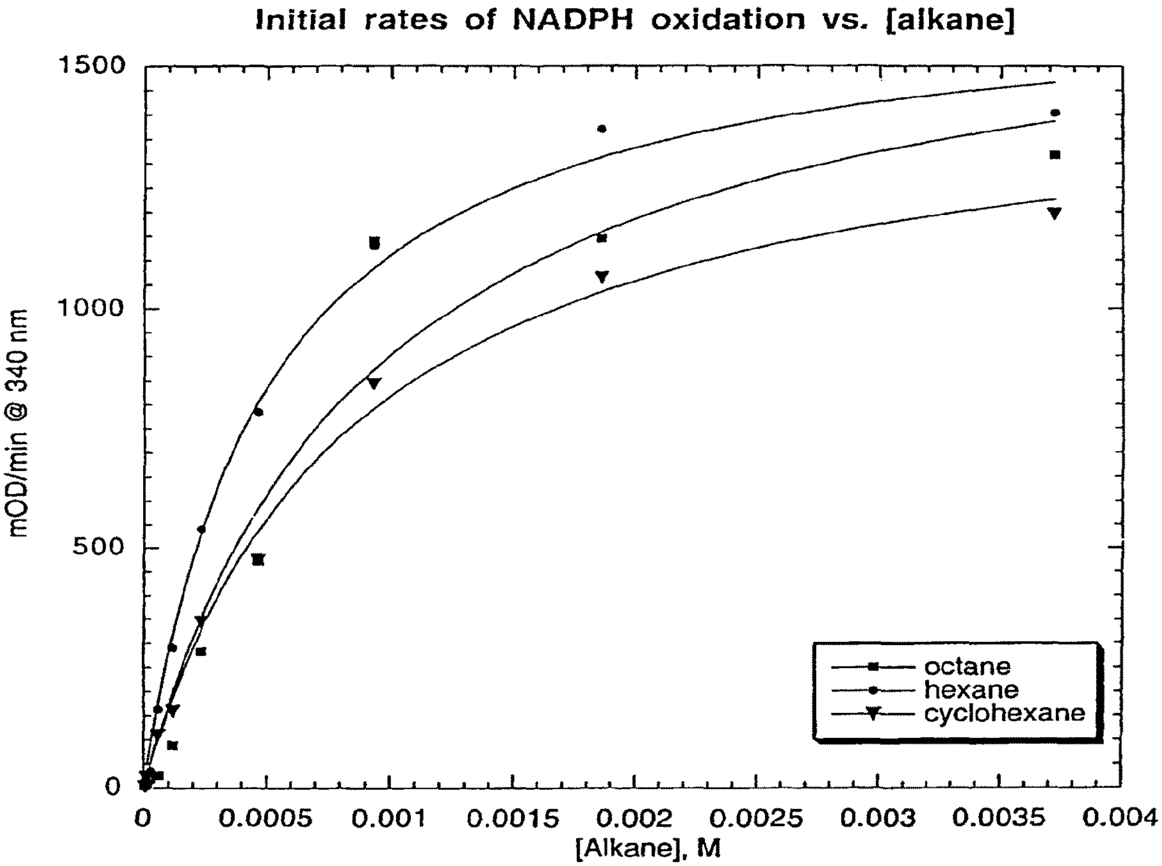
FIG. 5. Initial rates of NADPH oxidation vs alkane concentration for purified P450 BM-3 mutant IX139-3. Octane: $k_{cat}$=35.6 $s^{-1}$, Km=9.1×$10^{-4}$ M and $k_{cat}/K_m$=3.9×$10^4$ $M^{-1}s^{-1}$. Hexane: $k_{cat}$=34.3 $s^{-1}$, $K_m$=4.9×$10^{-4}$ M and $k_{cat}/K_m$=7.0×$10^4$ $M^{-1}s^{-1}$. Cyclohexane: $k_{cat}$=31.0 $s^{-1}$, $K_m$=8.4×$10^{-5}$ M and $k_{cat}/K_m$=3.7×$10^5$ $M^{-1}s^{-1}$.

Compared to wildtype, for octane oxidation, the $k_{cat}$ for IX139-3 improved 50 times, while the $K_m$ increased 45-fold (FIG. 5). The wildtype kinetic values for hexane and cyclohexane were of the same magnitude as for octane.

Figure 6:
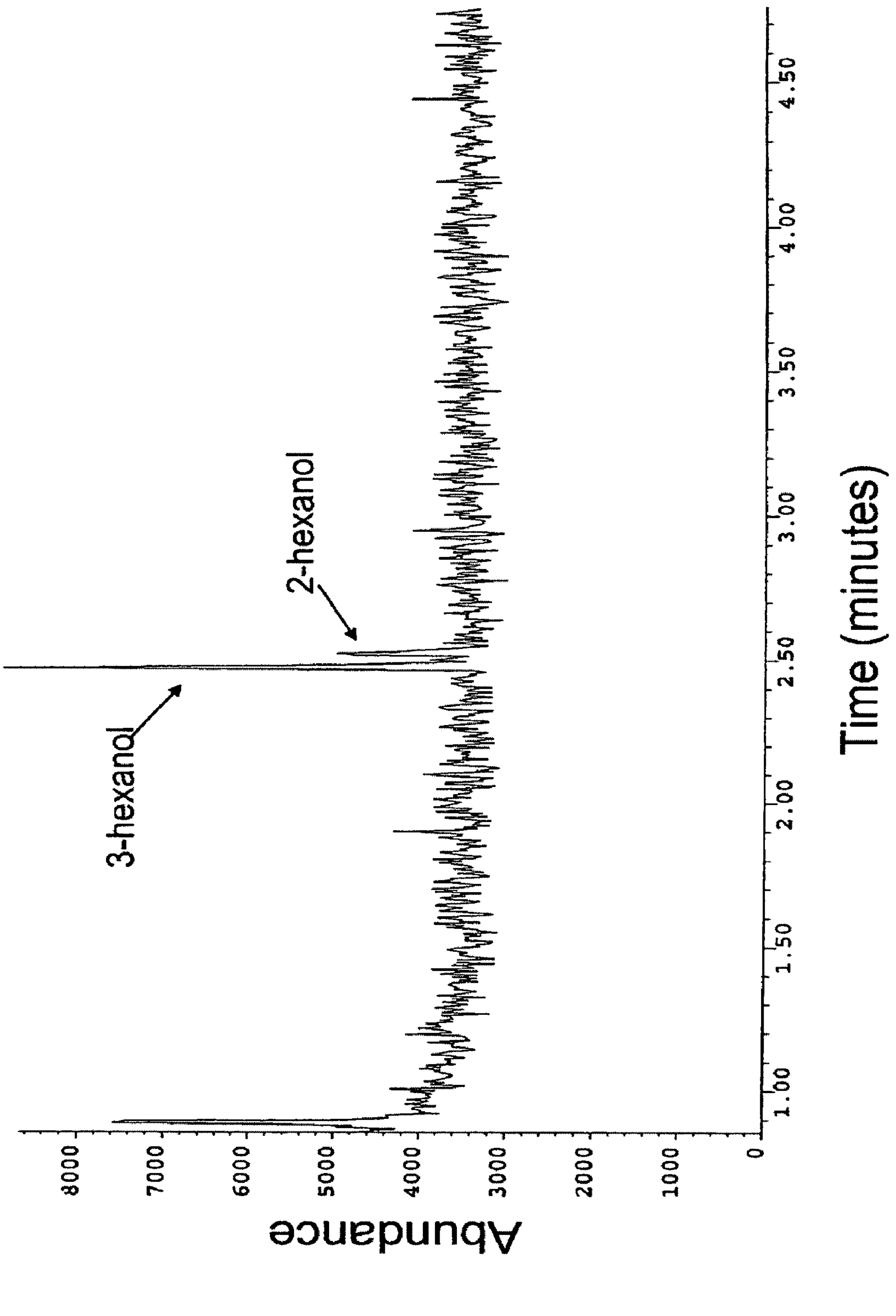
FIG. 6. Gas chromatogram of the oxidation products of hexane, catalyzed by DC79_1.

Results showing that hexane and cyclohexane were oxidized by IX79_1 were verified with GC/MS. Samples containing the cell lysate of IX79_1, hexane, and NADPH produced 2- and 3-hexanol (FIG. 6). 1-Hexanol was not detected. No products were found with IX79_1 and hexane alone, as a control.

Figure 7:
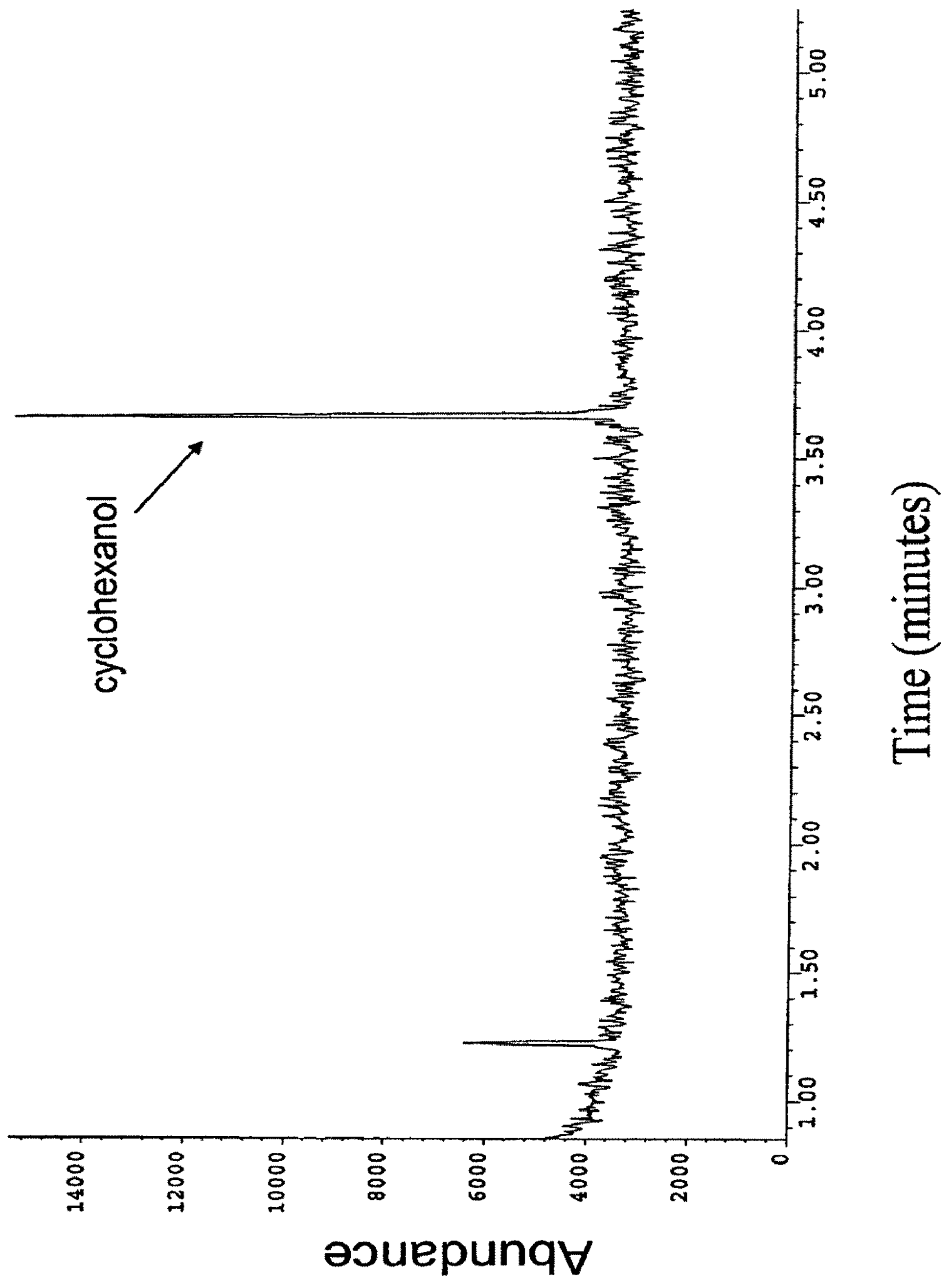
FIG. 7. Gas chromatogram of the oxidation products of cyclohexane, catalyzed by IX79_1.

IX79_1 in the presence of cyclohexane and NADPH produced cyclohexanol, and cyclohexanone was not detected (FIG. 7). Again, no products were detected with IX79_1 and cyclohexane alone.

Figure 8:
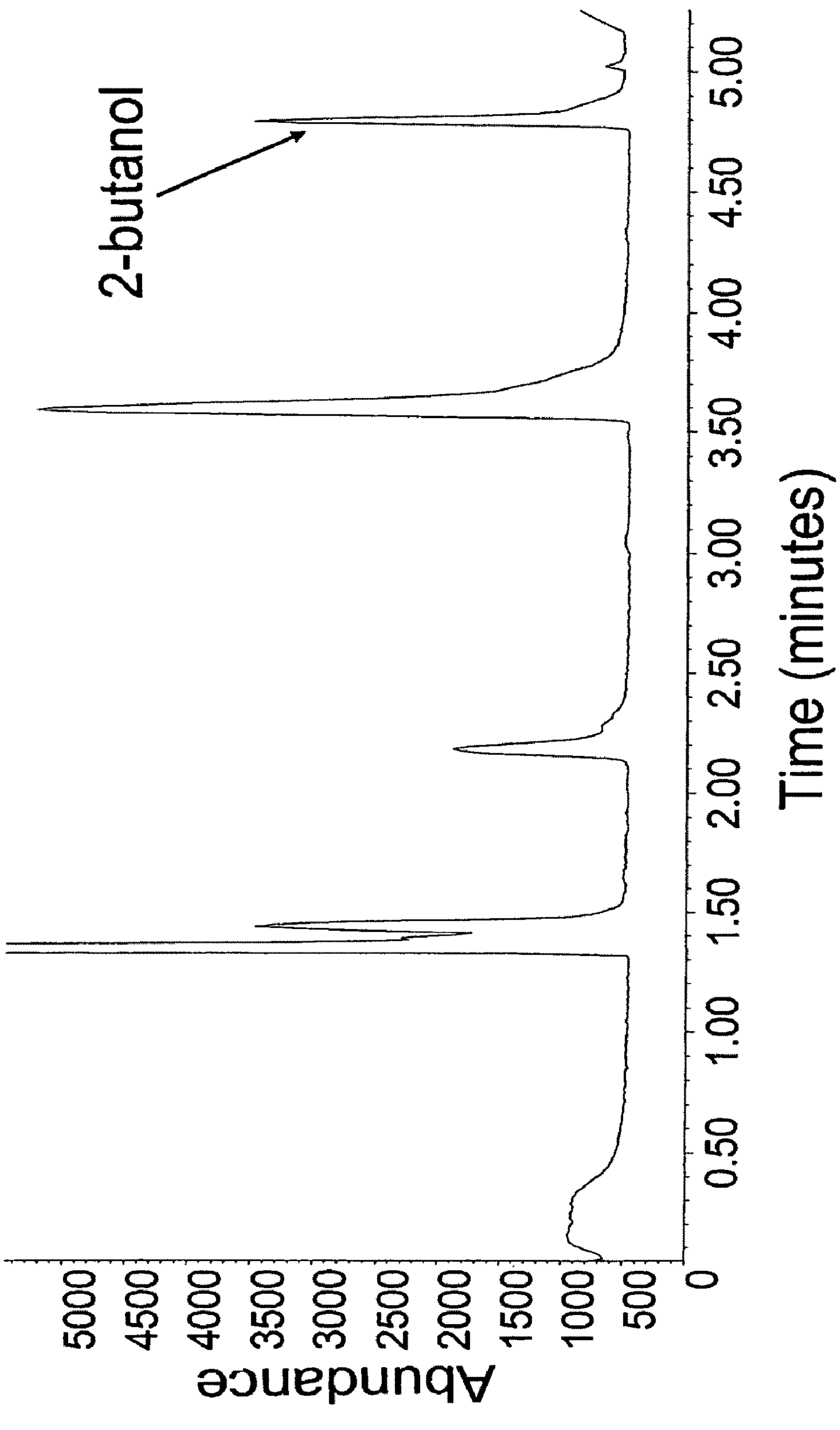
FIG. 8. Gas chromatogram of the oxidation products of butane, catalyzed by IX139-3.

Results also showed that IX139-3 was able to oxidize propane and butane, as verified with GC/MS. The reaction mixture contained enzyme, propane or butane, and in the presence of NADPH produced 2-propanol and 2-butanol (FIG. 8), respectively. Terminal hydroxylation was not detected under these reaction conditions.

Since the activity towards medium chain alkanes had already reached a significant level in generation five and IX139-3 displayed detectable activity for propane oxidation, it was decided to include propane into the screening program in the sixth generation. NADPH consumption assays of the sixth generation showed that mutant IX139-3 and some new variants also oxidized propane.

Agar Plate Colony Assay for Screening Mutant Libraries

This assay was based on the formation of the purple dye formazan upon reaction of NADPH with Nitro Blue Tetrazolium (NBT) salt in presence of the catalyst, phenazine methosulfate (oxidized, PMS) This color reaction is known as a photometric standard assay for dehydrogenase activity resulting in reduction of their cofactor NADP+ to NADPH.

In the present investigations it was used to measure depletion of NADPH that accompanies the P450-catalyzed oxidation of substrate. Bacterial colonies which are locally using up the cofactor from filter paper soaked with NADPH and substrate for hydroxylation reactions remained white after reaction of the remaining NADPH in the filter by reaction with NBT. This screen resulted in white spots on a purple filter paper caused by bacterial colonies consuming NADPH. The screen will be used for prescreening libraries of future generations. Positive clones could be verified with the other assay systems that look directly at oxidized product formation, since clones showing strongly uncoupled NADPH consumption, and no substrate oxidation, might appear as improved hydroxylation variants (false positives).

Example 2

Directed Evolution of a Cytochrome P450 Monooxygenase for Organic Solvent Resistance The total activity of P450 BM-3 in 96-well plates is-relatively low, especially in the presence of an organic solvent that further reduces the fraction of active enzymes. The mutant F87A converts the 12-pNCA substrate 4-5fold faster than the wild-type, the $K_m$ value is 1.5-fold lower, and the chromophore from 2-pNCA substrate is released completely and not only to 33% (Farinas, 2001; Schwaneberg, 1999a). Therefore, the F87A mutant and not the wildtype was used as a starting point of the in vitro directed evolution. The evolutionary experiment to discover more organic solvent resistant variants was performed under very restrictive conditions in order to preserve the valuable properties of the parents, a for monooxygenases remarkably high total activity and thermostability. The thermostability was under selective pressure by using the temperature inducible PRPL-promoter system, and only clones that showed a high activity and a high organic solvent resistance were used as parents for further generations.

Experimental

All chemicals were of analytical reagent grade or higher quality and were purchased from Fluka, Sigma or Aldrich. THF (Aldrich, 99.9%) and DSMO (Mallincicrodt AR, 99.9%) were of highest available purity grade. Enyzmes were purchased from New England Biolabs, Stratagene, and Boehringer Mannheim.

Cultivation and Expression in 96-Well Plates

The P450 BM-3 and P450 BM-3 F87A genes are under the control of the strong temperature inducible PRPL-promoter. Mutated BM-3 F87A variants were cloned into the pUSCI BM-3 vector by using BamHI//EcoRI or Age//EcoRI restriction sites. Transformed clones grown on LBamp plates (Genetix) were transferred via a colony picker (QPix; Genetix) into 96 well plates (flat bottom; Rainin) containing 120 µl LB culture supplemented with 12 µg ampicillin per well. After growth for 12 hours at 37° C. in a shaked incubator (280 rpm) 3 µl of each culture was transferred with a grooved 96-pin deep-well replicator tool (V&P-Scientific) into 2 ml deep-well plates (Becton Dickinson) containing 400-500 µl of enriched TBamp medium. TBamp solution was supplemented with 75 µl trace element solution (0.5 g $CaCl_2 \times 2H_2O$, 0.18 g $ZnSO_4 \times 7H_2O$, 0.10 g $MnSO_4$, $H_2O$, 20.1 g $Na_2$-EDTA, 16.7 g $FeCl_3 \times 6H_2O$, 0.16 g $CuSO_4 \times 5H_2O$, 0.18 g $CoCl_2 \times 6H_2O$, add 1 L $H_2O$ and autoclaVe) and 2 mg aminolaevulinic acid per 50 ml TB. *E. coli* cells were grown in this medium for 6 h at 37° C. then induced for 14 h at 42° C. All deep-well plates were covered with a taped lid. The original LBamp plates were stored until further use at 80° C. after adding 100 µl glycerol (sterile, 50% (v/v)).

Screening Procedures

All experiments were performed in organic solvent resistant polypropylene flat bottom 96 well plates (Greiner Bio-one). From each plate a blank pre-reading was recorded prior. performing assay procedures.

Fast prescreen procedure. Deep well cultures were mixed well by a liquid handling machine (Multirnek 96; Beckman) and 90 µl cell culture was transferred to each well of the reference and assay plate. To each well 40 µl Tris/HCl buffer (25 mM; containing 200 µM polymyxin B) and 5 µl 12-pNCA (15 mM, dissolved in DMSO) were pipetted using the Multimek. In addition 4.5 µl THF or 45 µl DMSO were transferred to each well of the assay plate. After an incubation time of 12 min the 12-pNCA conversion is initiated by adding 20 µl of a Isocitric co-factor regeneration solution (Isocitric acid 20 mM; $dH_2O$, $NADI^+$ 3 mM, Isocitric dehydrogenase 0.8 U/ml). The reaction was stopped after visible color development by the addition of 50 µl NaOH (1.5 M). After 8-12 h incubation and removal of the bubbles using the Bunsen burner the absorption at 410 nm of the clear solution was recorded. The P450 BM-3 variants revealing a high activity and a high organic solvent resistance were used for rescreening.

Rescreen procedure. Deep well cultures were in contrast to the prescreening method centrifuged at 4000 rpm for 10-20 min to remove the brownish TB media. The cell pellets were frozen overnight at 20° C. and resuspended in 200 µl lysomix (pH 7.5, 25 mM Tris/HCl or 25 mM $K_xPO_4$ supplemented with 1-50 mg lysozyme (Sigma) per 100 ml). 90 µl cell suspension per well was transferred to the reference plate and the assay plate. To lyse the *E. coli* cells the plates were incubated at 37° C. for 1 h. To each well 30 µl Tris/HCl buffer (25 mM) and 5 µl 12-pNCA (15 mM, dissolved in DMSO) were pipetted using the Multimek96. 15 µl THF solution (15% (v/v); $ddH_2O$) were additionally added to each well of the assay plate. After an incubation time of 12 min the 12-pNCA conversion is initiated by adding 20 µl of a Isocitric co-factor regeneration solution (Isocitric acid 20 mM; $dH_2O$, NADP+ 3 mM, Isocitric dehydrogenase 0.8 U/ml). The reaction was stopped after visible color development by the addition of 100 µl UT-buster (NaOH 1.5 M, 1.5 M Urea, 50% (v/v) DMSO). After 8-12 h incubation and removal of the bubbles using the Bunsen burner the absorption at 410 mn of the clear solution was recorded. The P450 BM-3 variants revealing a high activity and a high organic solvent resistance were cultured and expressed in shaking flasks for further characterization.

Shaking Flask Cultures and Purification

Fifty and 500 ml cultures were inoculated with a 1:100 dilution of an overnight Luria-Bertani (LB) culture of recombinant *E. coli* DH5 containing the pT-USC1 BM-3 variant. The cells were shaken at 300 rpm at 37° C. At an OD578=0.8-1 the cells were induced by increasing the temperature to 42° C. After 8 h, the cells were harvested by centrifugation at 4-8° C. The cell pellet was resuspended in Tris-HCl (15 ml, 0.1 M, pH 7.8) and lysed by sonication (3×2 minutes; output control=5, duty cycle 40%; Sonicator, Heat Systems—Ultrasonic, Inc.). The lysate was centrifuged at 23,300 g for 30 min. The supernatant was further cleared through a low protein binding filter (0.45 µM). The filtrate was loaded on a SuperQ650M anion exchanger column (TosoHaas) and purified as previously described (Schwaneberg, 1999b).

Photometric Enzyme Assays

Figure 9:
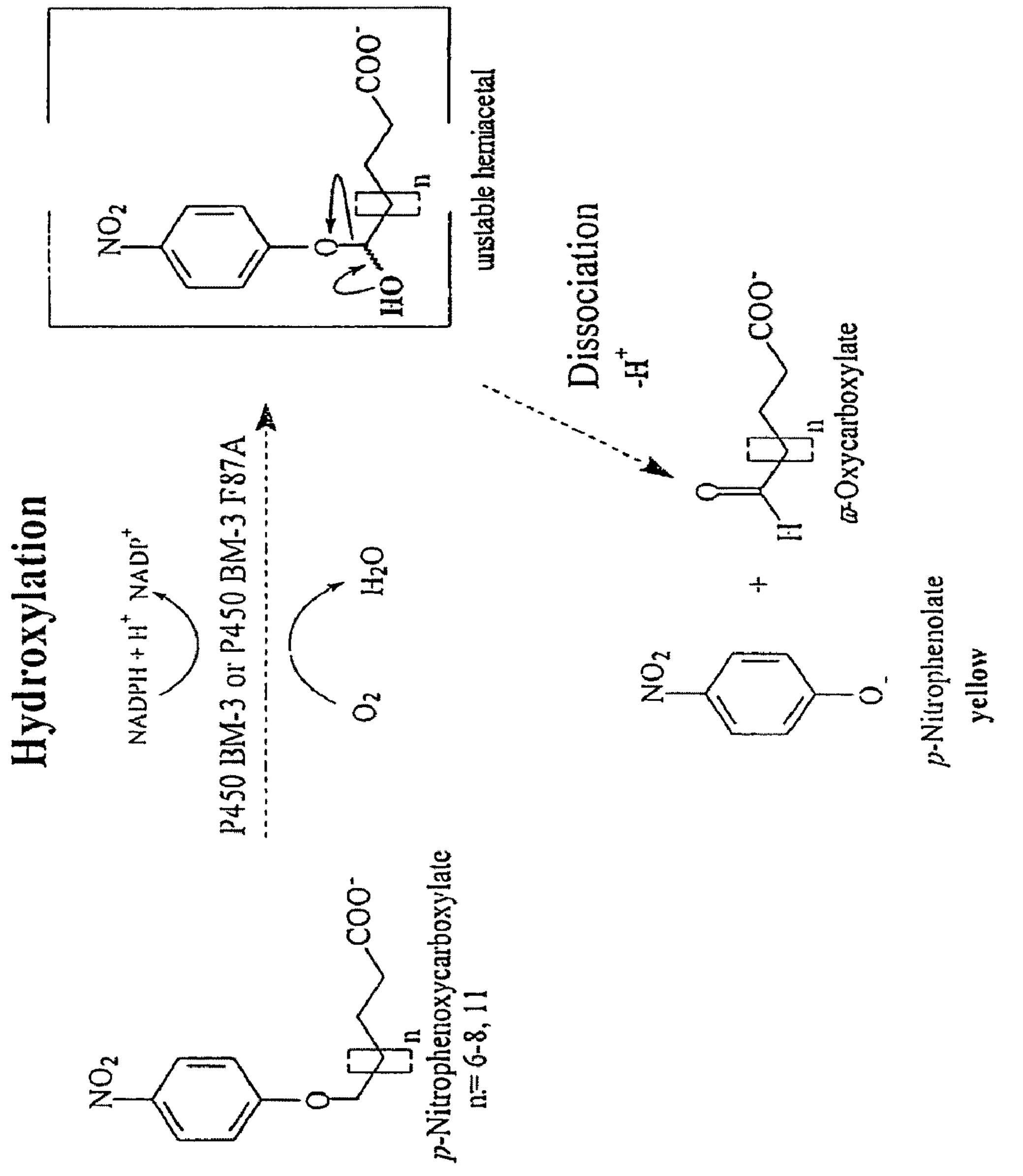
FIG. 9. Alternative representation of the pNCA assay principle (see also FIG. 2).

All photometric assays were carried out under aerobic conditions. UV/vis measurements were performed in a Shimadzu spectrophotometer (BioSpec-1601). P450 BM-3 F87A concentrations were measured by CO-difference spectra, as reported by Omura and Sato using $\epsilon$=91 $mM^{-1}cm^{-1}$ (Omura and Sato, 1964). Conversion of the p-nitrophenoxydodecanoic acid (12-pNCA) was monitored at 410 nm using a ThermomaxPlus plate reader (Molecular Devices) and an $\epsilon$=13,200 $M^{-1}cm^{-1}$ (Schwaneberg et al., 1999a). The principle of the p-nitrophenoxycarboxylic acid (pNCA) assay system is described in FIG. 9. ω-Hydroxylation of pNCA by P450 BM-3 leads to an unstable hemiacetal intermediate, which spontaneously dissociates into the ω-oxycarboxylic acid and the yellow chromophore p-nitrophenolate. This assay system allows a continuous photometric detection of the P450 BM-3 activity, as measured by the maximum turnover rate, i.e., the number of product molecules generated per minute (Schwaneberg et al., 1999a).

TABLE 5

PCR Primers. "N" means that any nucleotide (A, T, G, or C) can be used.

| Designation | Sequence (5'→3') | SEQ ID NO: |
|---|---|---|
| For error-prone PCR | | |
| pTBamHd | GAA CCG GAT CCA TGA CAA TTA AAG AAA TGC | 13 |
| Rev3250 | CTA TTC TCA CTC CGC TGA AAC TGT TG | 14 |
| For saturation mutagenesis at hot positions: | | |
| pT235_F | GCG ATG ATT TAT TAN NNC ATA TGC TAA ACG GA | 15 |
| pT235_R | TCC GTT TAG CAT ATG NNN TAA TAA ATC ATC GC | 16 |
| pT471_F | CAG TCT GCT AAA AAA GTA NNN AAA AAG GCA GAA AAC GC | 17 |

TABLE 5-continued

| PCR Primers. "N" means that any nucleotide (A, T, G, or C) can be used. | | |
|---|---|---|
| Designation | Sequence (5'→3') | SEQ ID NO: |
| pT471_R | GCG TTT TCT GCC TTT TTN NNT ACT TTT TTA GCA GAC TG | 18 |
| pT1024_F | GAC GTT CAC CAA GTG NNN GAA GCA GAC GCT CGC | 19 |
| pT3074_R | GCG AGC GTC TGC TTC NNN CAC TTG GTG AAC GTC | 20 |
| For back-mutation of F87 position: | | |
| A87F1 | GCA GGA GAC GGG TTA TTT ACA AGC TGG ACG | 21 |
| A87F2 | CGT CCA GCT TGT AAA TAA CCC GTC TCC TGC | 22 |
| F87Gly1 | GCA GGA GAC GGG TTA GGT CAA GCT GGA CG | 23 |
| F87Gly2 | CGT CCA GCT TGT ACC TAA CCC GTC TCC TGC | 24 |
| F87Trp1 | GCA GGA GAC GGG TTA TGG ACA AGC TGG ACG | 25 |
| F87Trp2 | CGT CCA GCT TGT CCA TAA CCC GTC TCC TGC | 26 |
| F87His1 | GCA GGA GAC GGG TTA CAC ACA AGC TGG ACG | 27 |
| F87His2 | CGT CCA GCT TGT GTG TAA CCC GTC CTC CTG C | 28 |
| F87Asn1 | GCA GGA GAC GGG TTA AAC ACA AGC TGG ACG | 29 |
| F87Asn2 | CGT CCA GCT TGT GTT TAA CCC GTC TCC TGC | 30 |
| F87Asp1 | GCA GGA GAC GGG TTA GAT ACA AGC TGG ACG | 31 |
| F87Asp2 | CGT CCA GCT GTA TCT AAC CCG TCT CCT GC | 32 |
| F87Arg1 | GCA GGA GAC GGG TTA CGT ACA AGC TGG ACG | 33 |
| F87Arg2 | CGT CCA GCT TGT ACG TAA CCC GTC TCC TGC | 34 |
| F87Val1 | GCA GGA GAC GGG TTA GTT ACA AGC TGG ACG | 35 |
| F87Val2 | CGT CCA GCT TGT AAC TAA CCC GTC TCC TGC | 36 |
| F87Ile1 | GCA GGA GAC GGG TTA ATT ACA AGC TGG ACG | 37 |
| F87Ile2 | CGT CCA GCT TGT AAT TAA CCC GTC TCC TGC | 38 |
| F87Lys1 | GCA GGA GAC GGG TTA AAA ACA AGC TGG ACG | 39 |
| F87Lys2 | CGT CCA GCT TGT TTT TAA CCC GTC TCC TGC | 40 |

Mutgenesis Conditions

For all the PCR reactions the thermocycler PTC 200 (MJ Reseach) was employed.

Protocol 1: First Mutant Generation

| Component | Volume (µl) |
|---|---|
| ddH2O | 42.5X-Y |
| Buffer (10X) | 5 |
| dNTP (10 mM) | 1 |
| pT_USC1 BM-3 | 1 (of a mini-prep) |
| RO | X (27 pmol) |
| Rev3250 | Y (27 pmol) |
| $MnCl_2$ | 0.04 mM |
| Taq polymerase | 5 U |
| Total volume | 50 |

PCR program: 94° C. for 4 min

94° C. for 1:10 min; 55° C. for 1:30 min 72° C. for 4 min (30 cycles)

72° C. for 10 min (1 cycle)

Protocol 2 (Gene Morph Kit): Second Mutant Generation

| Components | Volume (µl) |
|---|---|
| $ddH_2O$ | 40.5X-Y |
| Buffer 10X (Provided in kits) | 5 |
| dNTP mix (Provided in kits) | 1 |
| Plasmid | 2.5 |
| pT_BamHI | X (20 pmol) |
| Rev3250 | Y (20 pmol) |
| Mutazyme (Provided in kits) | 1 |
| Total volume | 50 |

PCR program: 95° C. for 30 s (1 cycle)

95° C. for 30 s; 55° C. for 30 s; 72° C. for 3:30 min (30 cycles)

72° C. for 10 min (1 cycle)

Protocol 3: Site Directed and Saturation Mutagenesis

| Components | Volume (μl) |
|---|---|
| ddH2O | 41XY |
| Pfu Buffer (10x) (From Stratagene) | 5 |
| Plasmid (1:20 dilution) | 2 |
| dNTP mix (10 mM) | 1 |
| Forward primer | X (17.5 pmol) |
| Reverse primer | Y (17.5 pmol) |
| Pfu turbo (From Stratagene) | 1 |
| Total volume | 50 |

PCR program: 94° C. for 4 min (1 cycle)

94° C. for 1:15 min; annealing 1:15 min; 68° C. for 16 min (20 cycles)

68° C. for 20 min (1 cycle)

Annealing temperature: 55° C. for pT235, pT471 and pT102

60° C. for back-mutations at position 87

Mutagenesis and Results

The results of these experiments are shown in TABLES 6 and 7 and FIGS. 10-13, and discussed below.

TABLE 6

Selected Cytochrome P450 Mutants Created From BM-3 F87A by Directed Evolution and other techniques. All mutations are relative to the wild-type cytochrome P450 BM-3 (SEQ ID NO: 2, and only non-silent mutations are shown.

| Generation/ Mutation Step | Mutant | Amino Acid Mutation | Codon Mutation |
|---|---|---|---|
| — | F87A | F87A | TTT→GCA |
| 1st Generation | F87AB5 | F87A | TTT→GCA |
| | | T235A | ACG→GCG |
| | | S1024R | AGT→AGA |
| | F87APEC3 | F87A | TTT→GCA |
| | | R471C | CGC→TGC |
| Saturation mutagenesis | F87ASB3 | F87A | TTT→GCA |
| | | R471A | CGC→GCT |
| | | T235A | ACG→GCG |
| | | S1024R | AGT→AGA |
| | F87ABC1F10 | F87A | TTT→GCA |
| | | R1024T | AGA→ACG |
| | | T235A | ACG→GCG |
| | | R471A | CGC→GCT |
| | F87ABC1B6 | F87A | TTT→GCA |
| | | R1024K | AGA→AAA |
| | | T235A | ACG→GCG |
| | | R471A | CGC→GCT |
| 2nd Generation | F87A5F5 | F87A | TTT→GCA |
| | | R471A | CGC→GCT |
| | | E494K | GAA→AAA |
| | | R1024E | AGA→GAG |
| | | T235A | ACG→GCG |
| Back-mutation | Wd | A87F | GCA→TTT |
| | W5F5 | R471A | CGC→GCT |
| | | E494K | GAA→AAA |
| | | R1024E | AGA→GAG |
| | | T235A | ACG→GCG |
| | WSB3 | R471A | CGC→GCT |
| | | T235A | ACG→GCG |
| | | S1024R | AGT→AGA |
| | WB5 | T235A | ACG→GCG |
| | | S1024R | AGT→AGA |
| | WBC1F10 | R1024T | AGA→ACG |
| | | T235A | ACG→GCG |
| | | R471A | CGC→GCT |

TABLE 6-continued

Selected Cytochrome P450 Mutants Created From BM-3 F87A by Directed Evolution and other techniques. All mutations are relative to the wild-type cytochrome P450 BM-3 (SEQ ID NO: 2, and only non-silent mutations are shown.

| Generation/ Mutation Step | Mutant | Amino Acid Mutation | Codon Mutation |
|---|---|---|---|
| Site-directed mutagenesis | F87G | F87G | GCC→GGT |
| | F87A | F87A | GCC (starting point) |
| | F87V | F87V | GCC→GTT |
| | F87I | F87I | GCC→ATT |
| | F87W | F87W | GCC→TGG |
| | F87D | F87D | GCC→GAT |
| | F87N | F87N | GCC→AAC |
| | F87H | F87H | GCC→CAC |
| | F87K | F87K | GCC→AAA |
| | F87R | F87R | GCC→CGT |

TABLE 7

Relative increase in 12-pNCA specific activity in the absence of additional co-solvents for 12-pNCA ("Absence of Co-Solvents"); and relative increases in total activity at 10% (v/v) DMSO ("10% DMSO") or 2% (v/v) THF ("2% THF").

| P450 BM-3 Variant | Absence of Co-Solvents | 10% DMSO | 2% THF |
|---|---|---|---|
| F87A | 1.00 | 1.0 | 1.0 |
| F87A5F5 | 3.40 | 5.5 | 10.0 |
| F87ASB3 | 2.53 | 3.7 | 5.7 |
| F87AB5 | 2.85 | 3.7 | 5.3 |
| F87ABC1F10 | 2.87 | 4.4 | 7.9 |
| Wd | 1.00 | 1.0 | 1.0 |
| W5F5 | 2.51 | 5.9 | 3.4 |
| WSB3 | 1.46 | 3.1 | 1.7 |
| WB5 | 1.03 | 1.8 | 1.0 |
| WBC1F10 | 2.01 | 3.5 | 2.3 |

First Mutant Generation

Random mutations were introduced by PCR into the BM-3 F87A gene coding for 1049 amino acids and a His6 tag at the C-terminal end, under conditions designed to generate an average of one to two amino acid substitutions per gene (protocol 1). The mutant library was screened for clones with improved organic solvent resistance by comparing the, activity in the presence and absence of a co-solvent. Approximately 6,520 clones were tested in 96 well plates using the 12-pNCA assay in presence and absence of an organic solvent. The candidates with high total activity and high activity ratios (activity in presence divided by activity in absence of an organic solvent) were selected for re-screening (protocol 1). Positive results of these assays were verified after expressing 39 clones of the first generation in 500 ml scale. Many of these clones were expressed higher than F87A. After lysing the *E. coli* cells and determining the P450 content, the organic solvent activities were measured using 1 ml cuvettes. The percentage of the relative activity in presence of organic solvent divided by the activity in absence of a co-solvent of these 39 clones is shown in FIG. 10. For more than 50% of the re-screened clones a superior organic solvent resistance was found. Interestingly, apart from false positives two types of clones were discovered a) Increased DMSO and reduced THF resistance, b) Increased DMSO and increased THF resistance. No clones with increased DMSO and reduced THF resistance were detected. For our purposes, the mutants with multiple organic solvents resistances are the most interesting ones. The in DMSO most resistant mutants F87AB5 and F87APEC3 were selected for detailed analysis. Sequencing revealed three non-silent mutations, two in F87AB5 (T(ACG) 235A(GCG); S(AGT)1024R(AGA)) and one in F87APEC3 (R(CGC)471C(TGC)). Interestingly, position 471 was again mutated in another clone, a substitution to serine instead of cystein was found. Under the assumption of identical expression levels an increased total activity of 3.7-fold at 10% (v/v) DMSO and of 5.3-fold at 2% (v/v) THF was measured for F87AB5 (Table 7).

Saturation Mutagenesis (SM)

Figure 11A:
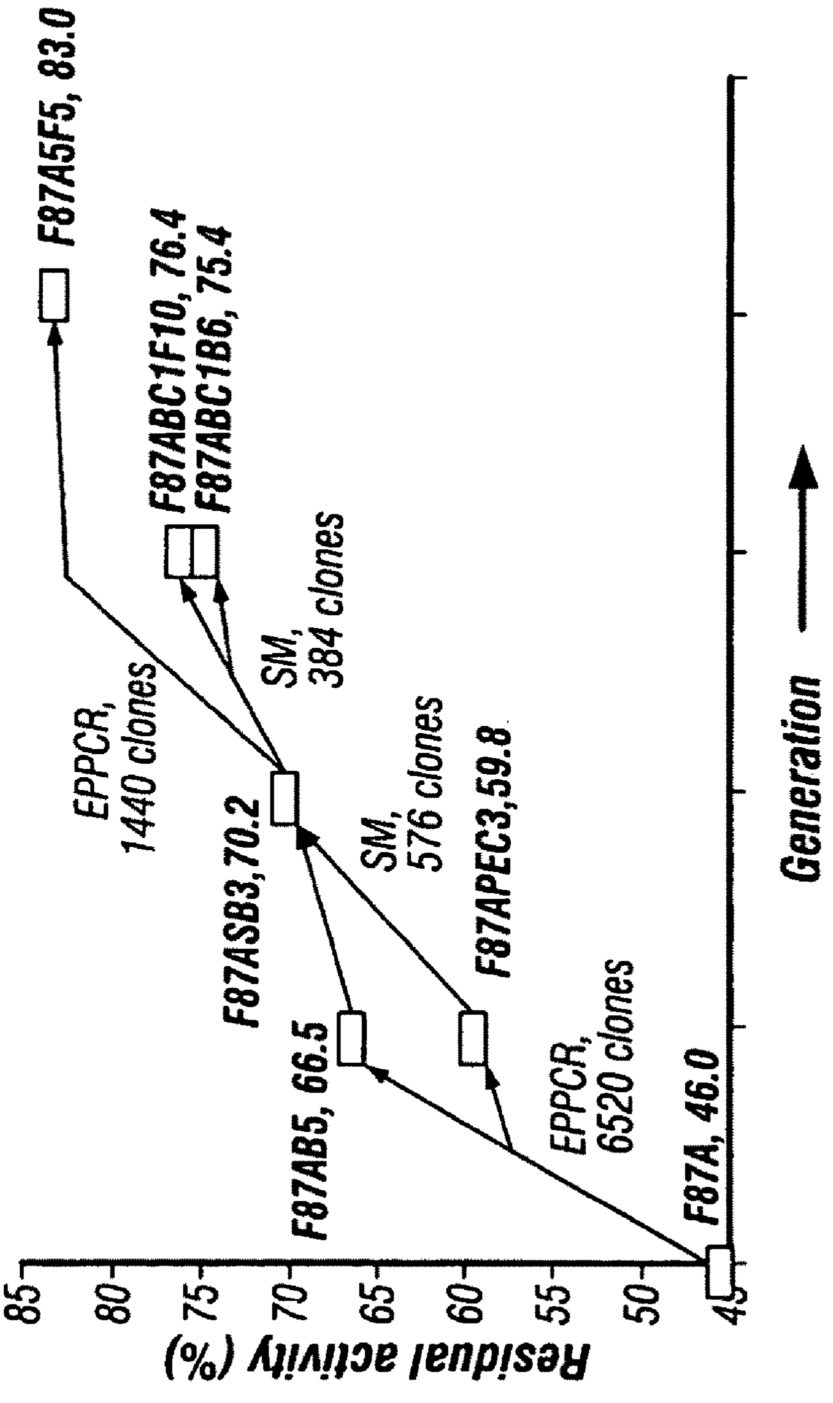
FIGS. 11A and B. Mutagenic pathways for parent F87A and the co-solvents DMSO (A) and THF (B) (see Example 2), showing increased residual activity versus enzyme generation.
Figure 11B:
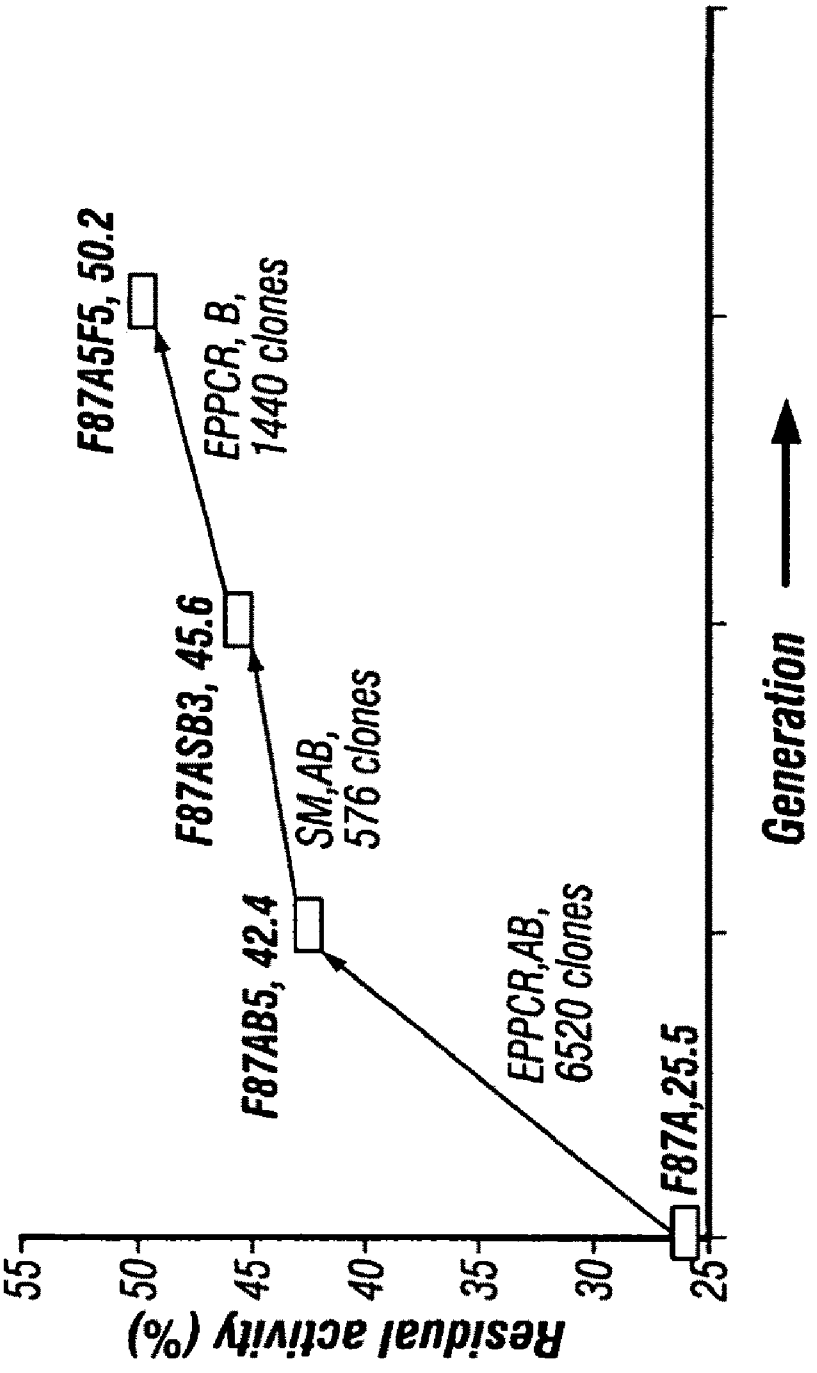

Only a limited set of amino acid (aa) substitutions can be explored by PCR mutagenesis at low error-rates and many as substitutions that require the exchange of two or more nucleotides will not be present in these PCR libraries. SM at sites identified by error-prone PCR allows exploring these as changes and can result in the discovery of superior catalysts. Therefore, SM was used to introduce all 20 as into position to the double mutant B3. Screening of about 576 clones revealed a more active triple mutant SB3. When expressed and purified in parallel with F87A, F87ASB3 revealed a up to 4 times higher expression level than F87A and the DMSO and THF resistance was further improved as shown in FIGS. 11A, 11B and by the organic solvent resistance profile in FIG. 12A. Sequencing revealed an exchange of R(CGC)→471A(GCT). The SM of the position A235 of clone SB3 resulted in no further improvements. All 5 sequenced clones contained an alanine at aa-position 235. SM at position 81024 revealed two more active clones, F87ABCIFIO and F87ABCIB6. F87ABCEF10 contains a R(AGA)1024T(ACG) substitution and BC1B6 a R(AGA)1024K(AAA) substitution. A detailed analysis of F87ABCIFIO revealed increased total activity of 4.4 fold at 10% (v/v) DMSO and of 7.9-fold at 2 (v/v) THF compared to the grandparent F87A (Table 7).

Second Mutant Generation (GeneMorph Kit)

Figure 12A:
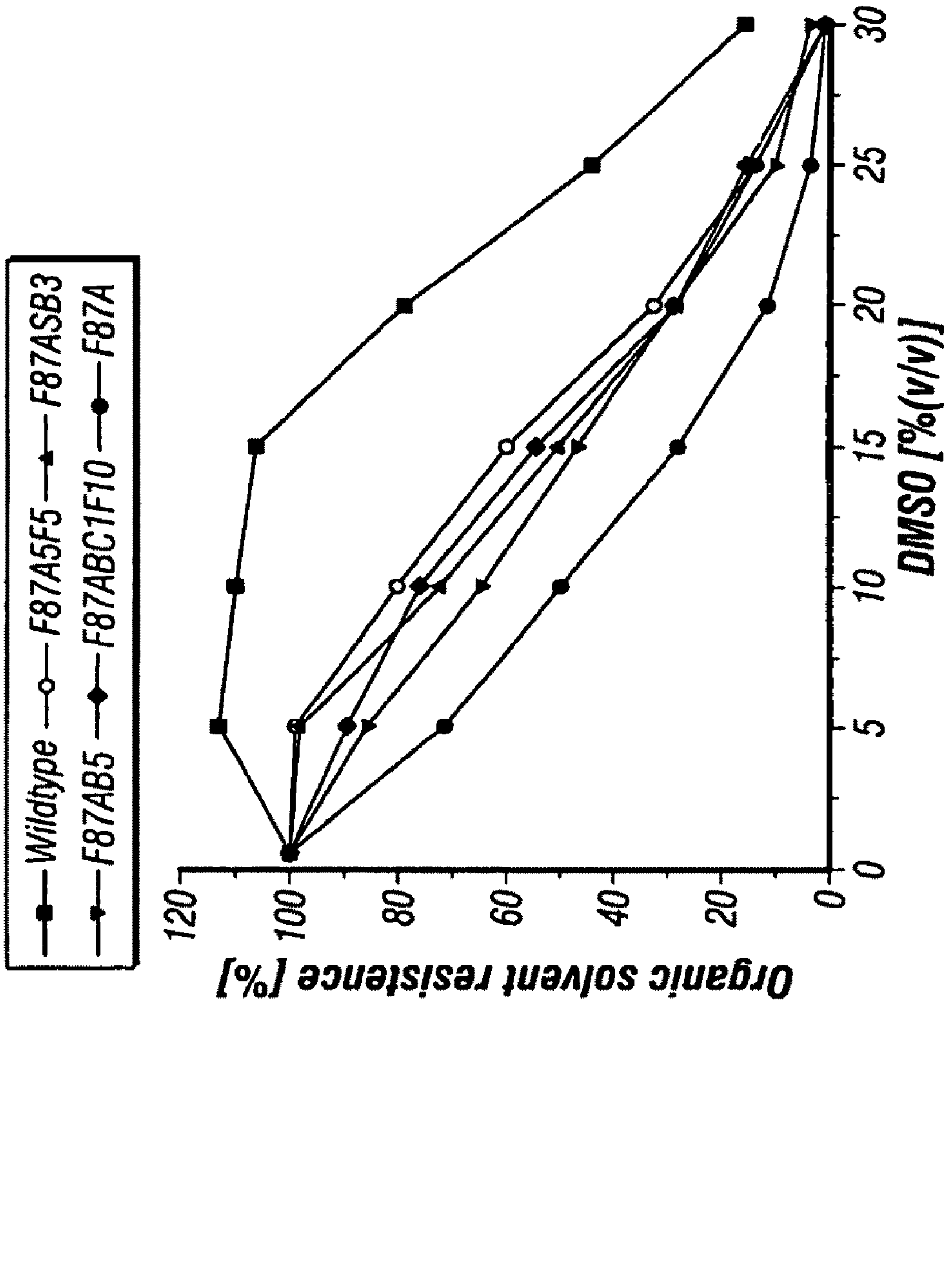
FIGS. 12A to C. Organic solvent resistance profile of the parent, showing organic solvent resistance against percentage of solvent (see Example 2). (A) DMSO as solvent. (B) THF as solvent. (C) Purified wild-type, F87A, and F87ASB3, using DMSO as solvent.
Figure 12B:
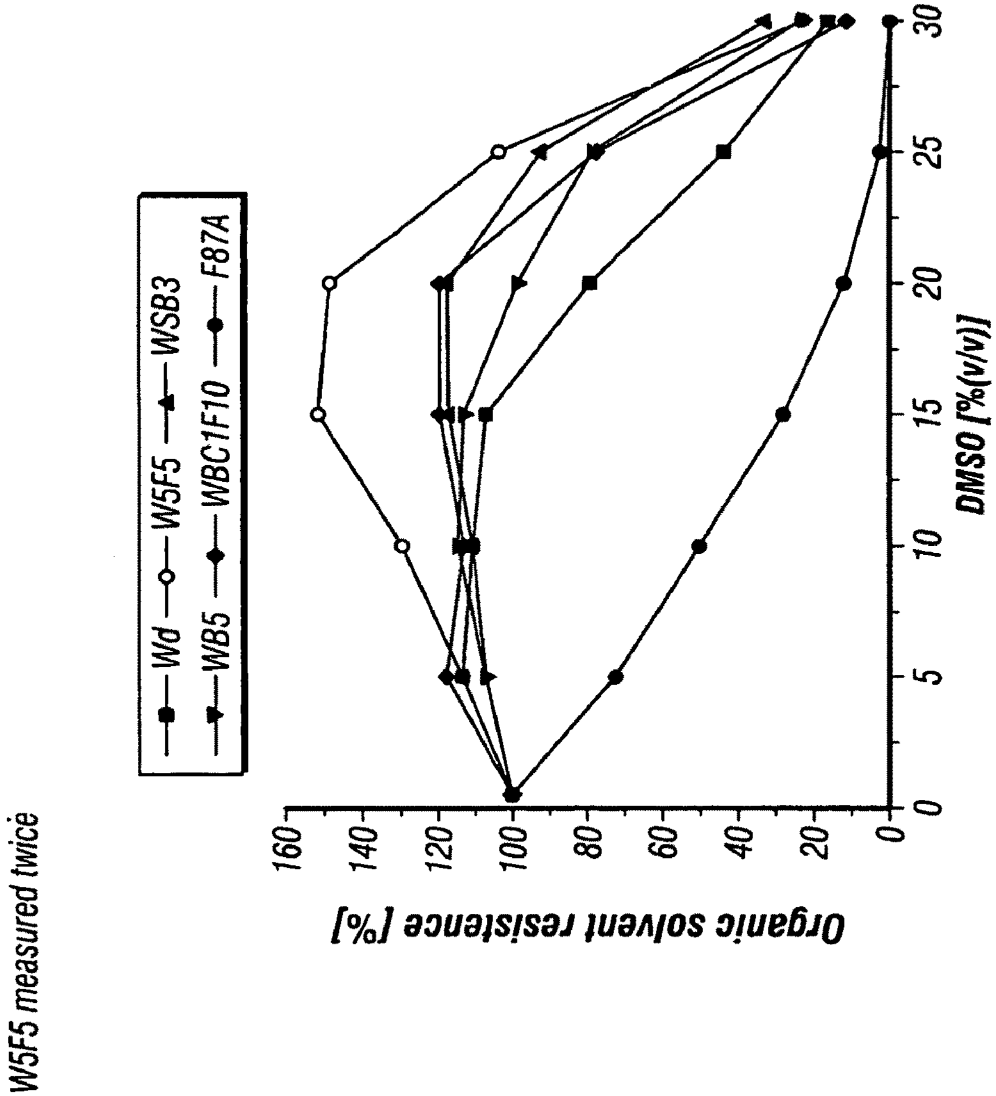
Figure 12C:
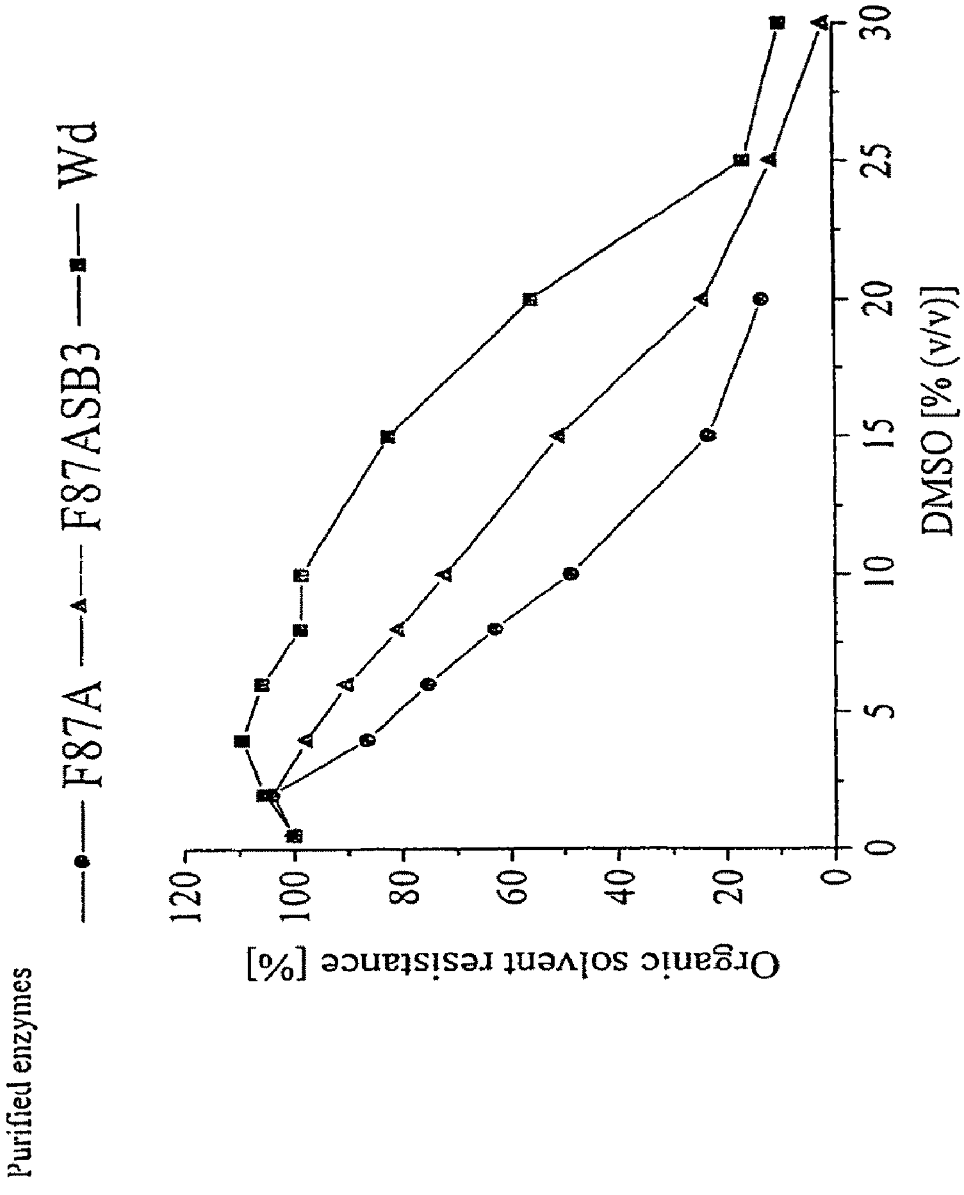

In parallel to the saturation mutagenesis, random mutations were introduced into the F87ASB3 clone. The Taq-Polymerase used in the first round of error-prone PCR has a strong bias to transitions whereas the polymerase in the GeneMorph is biased toward transversions (Stratagene Inc.). This round of error-prone PCR should therefore result in a different set of mutation and as changes. After only screening about 1440 clones, the mutant F87A5F5 was found. Sequencing revealed two non-silent transversions at aa-positions E(GAA) 494K(AAA) and R(AGA)1024E(GAG). The simultaneous exchange of three nucleotides to the complementary one at position 1024 seems to be very unlikely, however it has been confirmed by double sequencing this position in clone F87ASB3 and F87A5F5. F87ASF5 revealed a higher organic solvent resistance for DMSO and THF than any previous clones. For F87A5F5 a, compared to F87A, increased total activity of 5.5-fold at 10% (v/v) DMSO and of 10-fold at 2% (v/v) THF (Table 7) was discovered. The mutagenic pathways starting from the parent F87A are summarized in FIGS. 11A and 11B and the organic solvent resistance profiles in DMSO, THY, acetone, acetonitrile, DMF, and ethanol are shown in FIGS. 12 and 13. In particular, FIGS. 12A-G show that the evolved mutants, including F87A5F5, exhibit an increased resistance to these organic solvents.

Purification

Figure 13A:
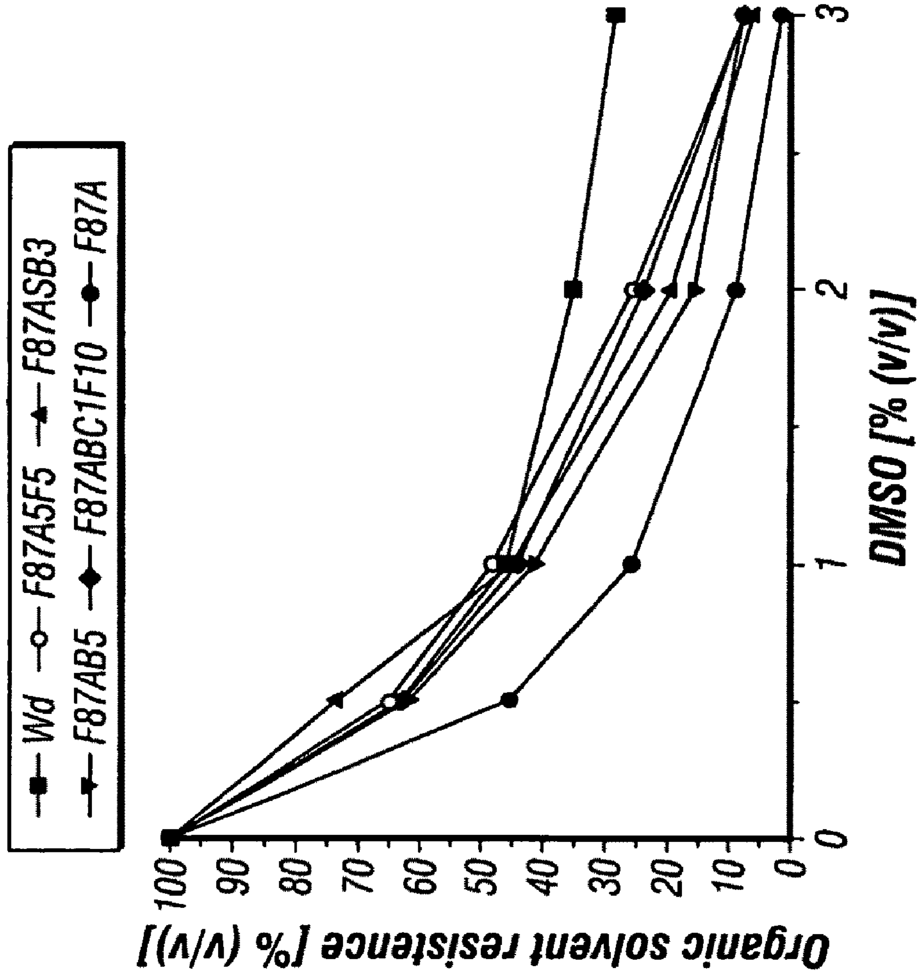
FIGS. 13A to F. Organic solvent resistance profile of back-mutated BM-3 variants. Solvent: A=DMSO; B=THF; C=acetone; D=acetonitrile; E=DMF; and F=ethanol.

F87A, F87ASB3 and the wild-type were simultaneously expressed and one by one purified (FIG. 12C). A comparison of the organic solvent resistance between lysed crude extracts and purified monoxygenase revealed very similar resistance toward DMSO (FIGS. 12C and 13A). For THF, the resistance of the purified enzyme was reduced between 3-9%. This reduction might be correlated to hydrophobic impurities in crude protein extracts and relatively small amounts of THF present in the reaction solution.

Back-mutation of Position 87

Figure 13B:
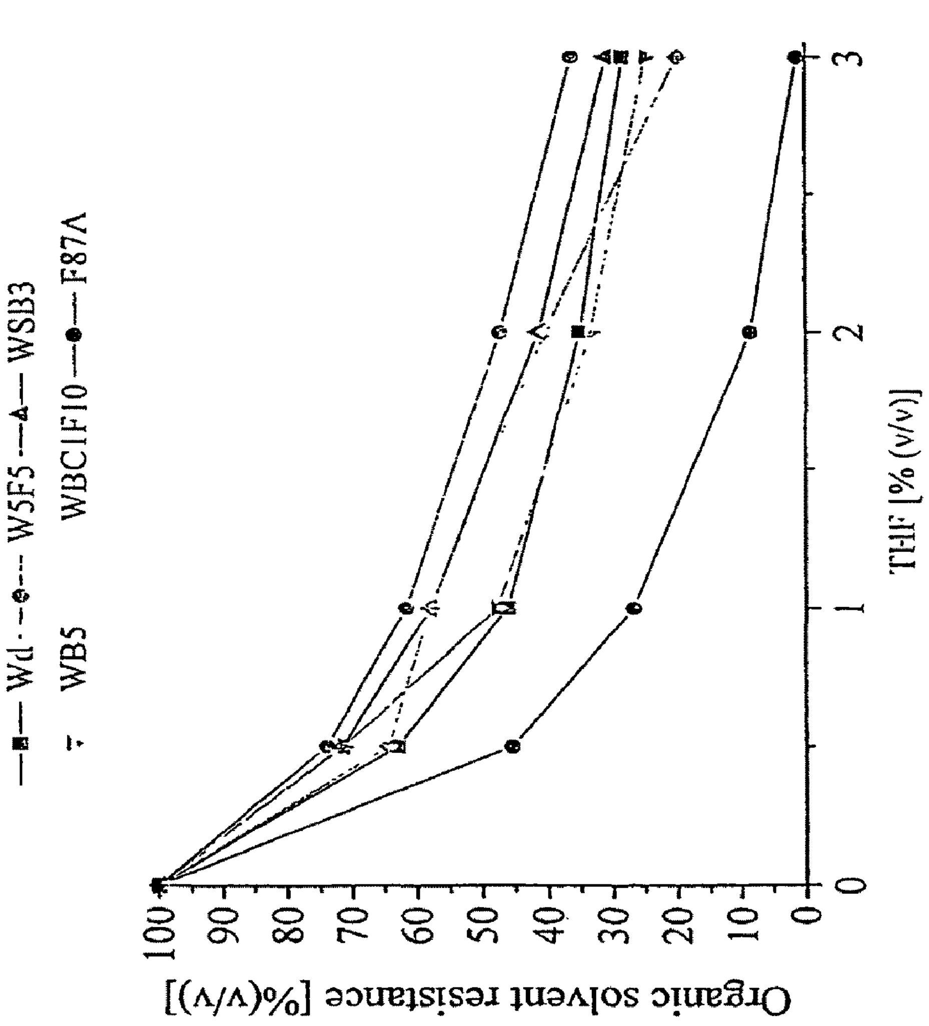
Figure 13C:
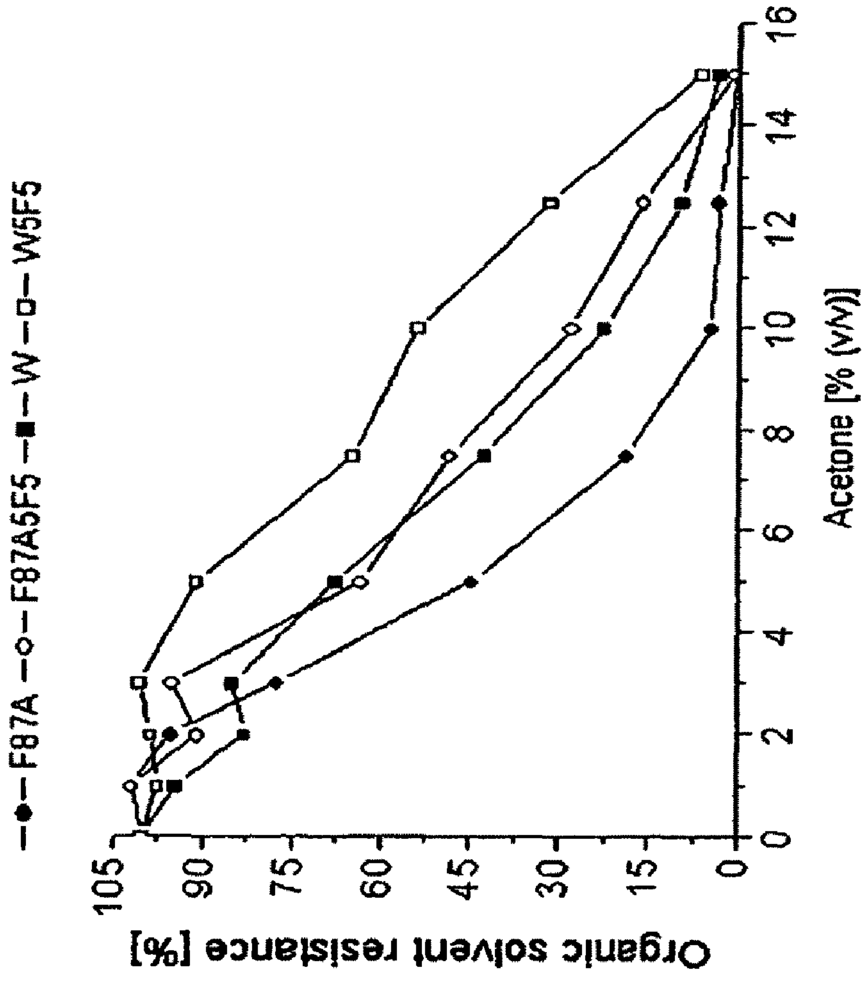
Figure 13D:
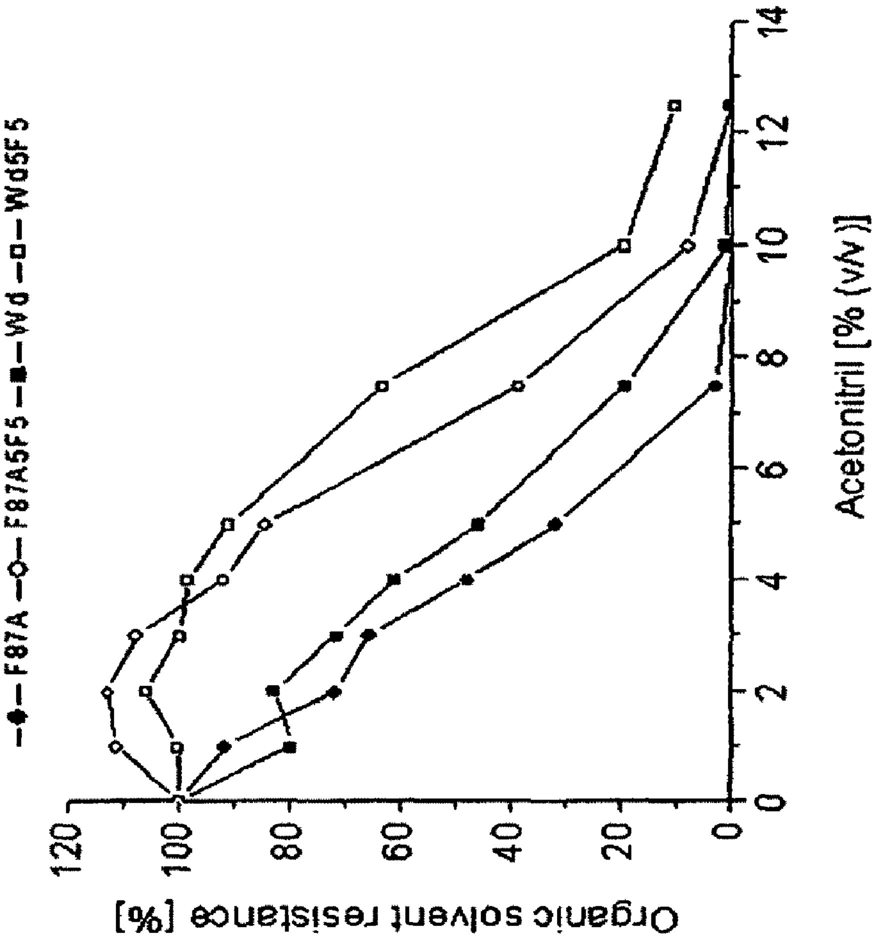
Figure 13E:
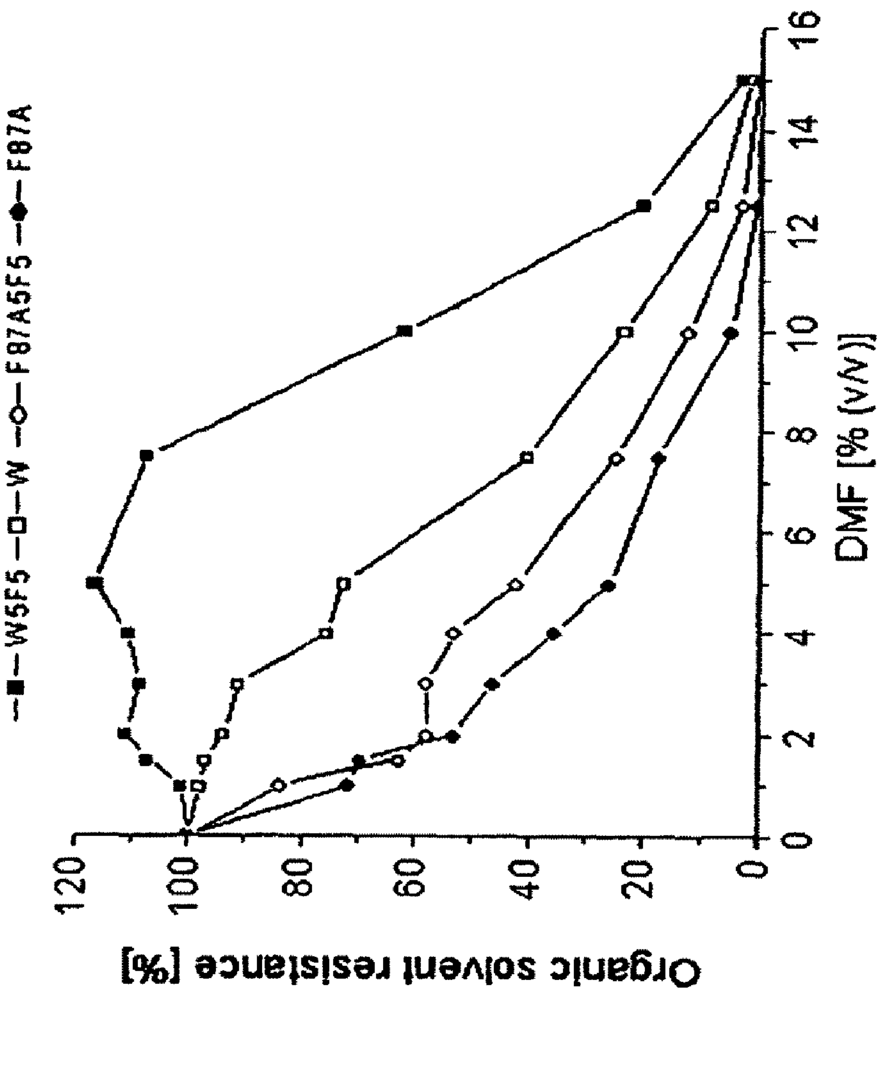
Figure 13F:
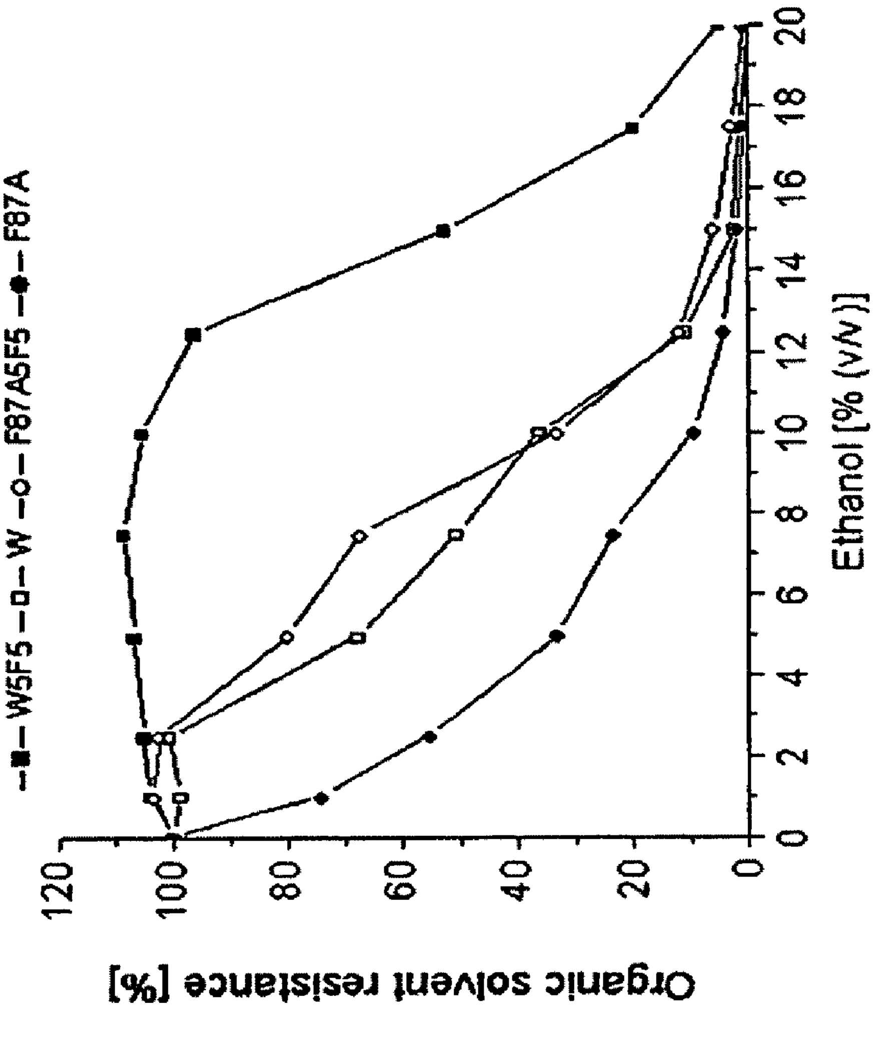

The comparison of the organic solvent activity of the wild-type and the mutant F87A revealed a significant higher resistance of the wild-type enzyme in organic co-solvents (FIG. 12C). Therefore, the best clones of the laboratory evolution experiment (FIG. 3) were back-mutated at position 87 to the wild-type. FIGS. 12B and 13B show that the activity profile of the fraction of in organic solvent active clones is especially for DMSO shifted to higher co-solvent concentrations. For example, the back-mutated clone W5F5 has an increased total activity of 5.9-fold at 25% (v/v) DMSO and of 3.4 fold at 2 (v/v) THF compared to the wild-type (Table 7). However, improvements are generally for the wild-type mutants, especially in the case of THF, lower compared to the factors for F87A. Interestingly, 30% (v/v) DMSO seems to be a threshold value to trigger a reduced organic solvent resistance. However, the expression rates and activity of W5F5 are sufficient to use this mutant as a starting point for further directed evolution.

The results of the back-mutation encouraged us to investigate in detail the influence of position 87 toward the activity of P450 BM-3 in organic co-solvents. By site-directed mutagenesis as changes from F to G, A, V, I, F, W, D, N, H, K and R were introduced (protocol 3) and confirmed by sequence analysis. The as changes to A, F revealed a fast 12-pNCA conversion and to I, V, G a lower one. All other mutants showed no detectable activity for 12-pNCA. These results were confirmed by using coumarone as a substrate and the Gibbs assay to detect hydroxylated products. The only exception was a low activity of the F87H toward coumarone. Initial analysis of the active clones discovered a size-depending organic solvent resistance in the order F>I>A, G, V.

Evolution has generated a stunning variety of enzymes through mutation/recombination and natural selection. However, monooxygenases are not well suited for industrial application.

The results reported herein proves that laboratory evolution offers a fast and elegant way to adapt these enzymes to our needs in biotechnology applications. The achieved improvements in organic co-solvents resistance will bring this exceptional class of enzymes a step closer to industrial applications.

Example 3

Investigations of Solvent Conditions and Substrates for P450 BM-3 Mutant IX139-3

Cytochrome P450 BM-3 from Bacillus megaterium (Bodupalli et al., 1990) (P450 BM-3), a medium-chain (C12-C18) fatty acid monooxygenase, has been converted into a highly efficient catalyst for the conversion of alkanes to alcohols (See Example 1). The evolved P450 BM-3 exhibits higher turnover rates than any reported biocatalyst for selective oxidation of hydrocarbons. Unlike naturally-occurring alkane hydroxylases, among the best known of which are the large, membrane-associated complexes of methane monooxygenase (MMO) and AlkB, the evolved enzyme is water soluble and does not require additional proteins for catalysis. The evolved alkane hydroxylase was found to have even higher activity on fatty acids, the presumed biological substrates for P450 BM-3, which was already one of the most efficient P450s known. A broad range of substrates that includes the gaseous alkane propane induces the low to high spin shift, which activates the enzyme. The first soluble catalyst for alkane hydroxylation at room temperature, this laboratory-evolved P450 opens new opportunities for clean, selective, hydrocarbon activation for chemical synthesis and bioremediation.

Materials and Methods

Expression of P450 BM-3 Variants

See Example 1.A. Expression and purification of P450 BM-3 variants.

Mutagenic PCR and StEP Recombination

For the first two generations, mutagenic PCR of the heme domain was performed as described (Farinas et al., 2001), using the following primers together with Taq polymerase (Roche):

```
                                       (SEQ ID NO: 41)
Bamfor 5'-ACAGGATCCATCGATGCTTAGGAGGTCATATG-3'

                                       (SEQ ID NO: 42)
Sacrev 5'-GTGAAGGAATACCGCCAAG-3'
```

The PCR product was cloned by replacing the BamHI/SacI fragment of p BM-3_WT18-6. Nine mutants from generation 2 showing at least 2-fold improved activity on 8-pnpane were recombined by staggered extension process (StEP) (see Example 1; Zhao et al., 1998) using the same primers and 10 seconds extension time. A variant with 3 mutations (V78A, H236Q, E252G) with at least 2-fold improvement in activity relative to the parents was isolated. The 4th and 5th generations were generated by error-prone PCR using the Genemorph kit (Stratagene) according to the manufacturer's protocol, using approximately 1 to 10 ng of template DNA. The most active mutant, IX139-3, was isolated from the 5th generation. Sequencing of the gene revealed 13 point mutations. Eleven lead to amino acid substitutions (V78A, F107F, H138Y, T1751, V1781, A184V, H236Q, E252G, R255S, A290V, A295T, L353V, Q397Q), and two were synonymous.

Preparation of Cell Lysates

For high throughput screening, clones from the first three generations were cultivated as described (See Example 1; and Farinas et al., 2001). For subsequent generations, colonies were picked and inoculated by a Qpix (Genetix) robot into Luria Bertani media (LB, 350 μL, 100 mg/L ampicillin) into 1 mL deep well plates. The plates were incubated at 30° C., 250 rpm, and 80% relative humidity. After 24 hours, clones from this pre-culture were inoculated using a 96 replicator pin into 2 ml deep well plates containing Terrific broth media (TB, 400 μL), ampicillin (100 mg/L), isopropy-β-D-thiogalactoside (IPTG, 10 μM), and ALA (0.5 mM). The clones were cultivated at 30° C. for 24-30 hours. Cell pellets were frozen at −20° C. and resuspended in phosphate buffer (1 mL, 0.1 M, pH 8.0) containing lysozyme (0.5 mg/mL), DNase I (0.1 μg/mL) and $MgCl_2$ (10 mM). After 60 min at 37° C., the lysates were centrifuged and the supematant was diluted for activity measurements in 96 well microtiter plates.

High Throughput Determination of Enzymatic Activity

Mutant libraries were screened on 8-pnpane as described (See Example 1 and Farinas et al., 2001). A cofactor (NADPH) depletion assay was used to determine turnover rates. E. coli lysates of the mutants were diluted into 96 well microtiter plates containing phosphate buffer (200 μl, 0.1 M, pH 8.0), alkane substrate (0.5-1 mM), and DMSO (1%). The liquid alkanes were added to the buffer using alkane stock solutions in DMSO, whereas the gaseous alkanes were bubbled into buffer for about 45 min to obtain saturated solutions. The reaction was initiated by addition of NADPH (200 mM), and the oxidation of NADPH was monitored at 340 nm. A total of about 10,000 colonies were screened over 5 generations. The determination of the maximal turnover rate is described in Example 1.

Solid Phase Assay

A solid phase NADPH depletion assay was used preselection of the fifth-generation mutant library. Cells were grown on LB agar plates containing ampicillin (100 μg/ml), ALA (1 mM) and isopropyl-β-d-thiogalactopyranoside (10 μM).

The assay solution contained phosphate buffer (0.1 M, pH 8.0), polymyxin B sulfate (100 μM) as a cell permeabilizer, NADPH (2 mM), and substrate (5 mM) and was sonicated before use. A nitrocellulose membrane soaked with this substrate solution was placed directly onto the colonies on the agar plate. The sensitivity of the assay was regulated by the NADPH concentration. After the reaction (about 5-15 min), nitro blue tetrazolium (0.5 mg/ml) in phosphate buffer (0.1 M, pH 8.0) and some crystals of phenazine methosulfate were pipeted directly onto the membrane. Active colonies, which deplete NADPH, were identified as white spots on the purple membrane. Positive colonies were picked with a toothpick and streaked out on fresh agar plates to obtain single colonies for rescreening.

GC/MS Analysis

See Example 1.

Substrate Binding

Dissociation constants for octane, hexane, and lauric acid were determined at 25° C. as described (Modi et al., 1995, hereby incorporated by reference in its entirety) from the change in absorption at 418 nm upon substrate binding. For the alkanes, an enzyme solution (3-5 mM) in buffer (0.1 M potassium phosphate pH 8.0) was titrated with a stock solution of alkane (octane: 2 mM in methanol; hexane: 10 mM in methanol). Methanol (1%) added to an enzyme solution does not induce a spin state shift. For laurate, the reaction solution contained enzyme (3-5 mM) and laurate (1 mM) in buffer (20 mM MOPS, 100 mM KCl, pH 7.4). Aliquots of the enzyme/substrate solution were removed and replaced with an equal volume of an enzyme solution.

Results

Table 8 shows the relative amounts of different products obtained for alkane oxidation, comparing wild-type cytochrome P450 BM-3 to the evolved mutant enzyme IX139-3.

TABLE 8

Product distribution for alkane oxidation by wild-type P450 BM-3 and IX139-3

| Substrate | Product | 139-3 (%) | Wild-type (%) |
|---|---|---|---|
| Octane | 2-octanol | 66 | 17 |
| | 3-octanol | 32 | 40 |
| | 4-octanol | 2 | 43 |
| Hexane | 2-hexanol | 19 | 20 |
| | 3-hexanol | 81 | 80 |
| Cyclohexane | cyclohexanol | 100 | 100 |
| Butane | 2-butanol | 100 | Not determined |
| Propane | 2-propanol | 100 | Not determined |

The results show that laboratory evolution methods consisting of sequential rounds of random mutagenesis, in vitro recombination, and high throughput screening converted this highly efficient fatty acid monooxygenase into one that can hydroxylate hexane and other alkanes similarly well. In a preliminary study (Farinas et al., 2001), it was verified that P450 BM-3 showed very low activity towards octane (Munro et al., 1993). A colorimetric screen using p-nitrophenoxy octane (8-pnpane) as an alkane substrate analog identified more active clones. Unfortunately, a plateau in the enzyme's activity on alkanes was reached after a few rounds of evolution, and further screening yielded no new improvements.

When designing a screening strategy for identifying cytochrome P450 BM-3 mutants that catalyze the hydroxylation of alkanes, it was necessary to have an assay sensitive enough to observe improvements when the activities were still very low. The colorimetric assay on the surrogate substrate 8-pnpane nicely fulfilled this role. The risk to using a surrogate substrate such as 8-pnpane, however, is that the enzyme may become 'addicted' to that particular substrate. Activity towards the desired substrate may not be increasing in the same proportion (or not at all). By the third generation of mutagenesis and screening, the most active BM-3 variant acquired sufficient activity to enable us to screen mutant libraries for activity directly on an alkane(octane) using a high throughput NADPH consumption assay (see Example 1). NADPH oxidation alone, however, may not provide an accurate measure of catalytic activity since reducing equivalents from NADPH can be diverted into forming reduced oxygen intermediates ($H_2O$ or $H_2O_2$). Therefore all subsequent generations were screened using a combination of the 8-pnpane assay, sensitive to product formation, and NADPH consumption in the presence of octane (see Experimental).

By monitoring cell growth under conditions where the P450 enzyme was expressed, we also determined that the enzyme had become toxic to the *E. coli* cells during the process of acquiring higher activity towards alkanes. This increased toxicity placed an artificial barrier on how active the enzyme could become and still appear as a positive during high throughput screening for alkane hydroxylase activity. By altering the growth and expression conditions to limit enzyme production during growth we were able to continue the evolution and identify P450 BM-3 mutants with very high alkane hydroxylation activities.

Figure 14:
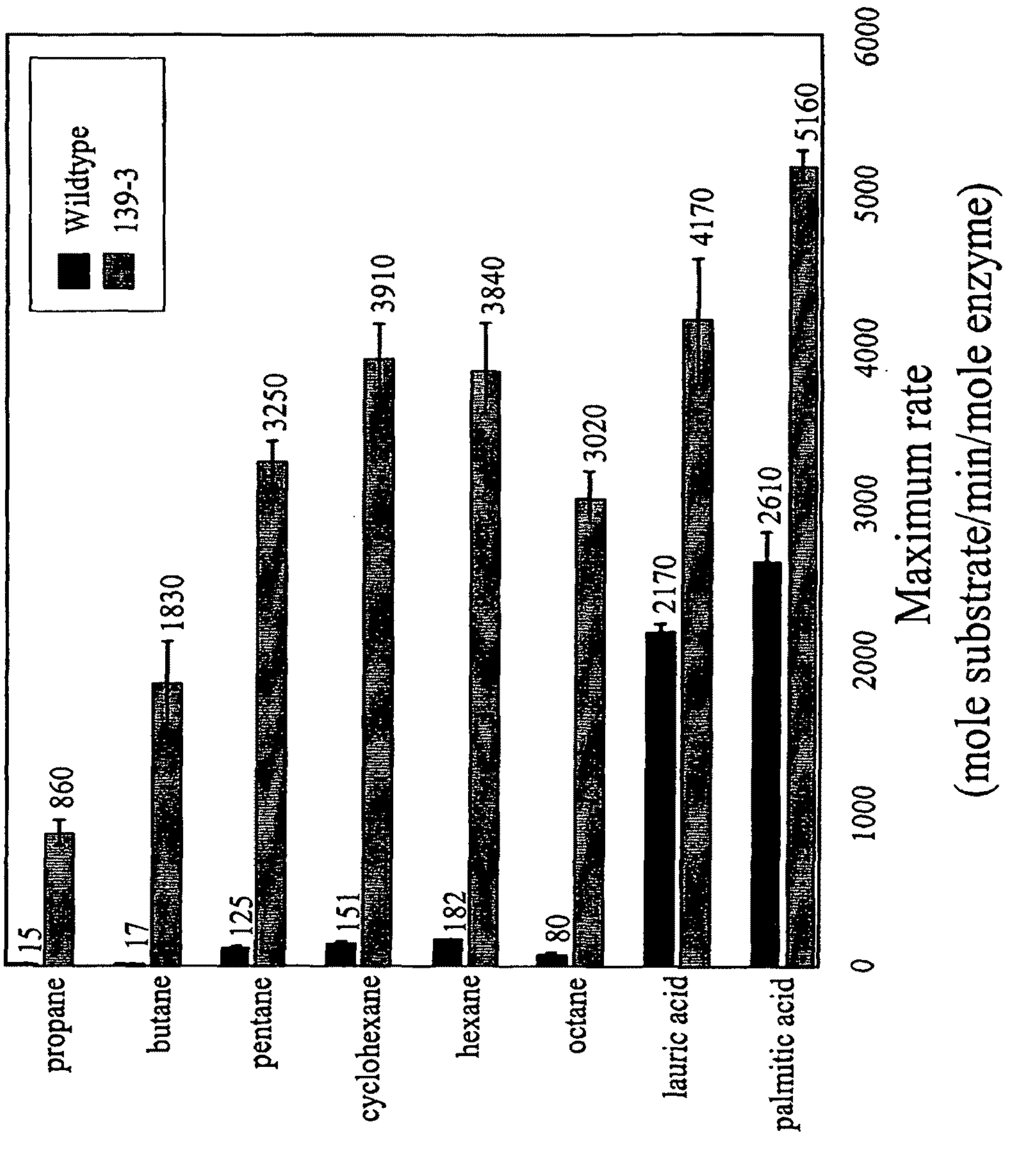
FIG. 14. Maximum turnover rates (mole substrate/min/mole enzyme) for P450 BM-3 wildtype (black bars) and IX139-3 (shaded bars) on alkane and fatty acid substrates.

Five generations of mutagenesis and screening yielded P450 BM-3 mutant IX139-3. As shown in FIG. 14, the enzyme evolved using 8-pnpane and octane to screen for more active clones was highly active on octane, hexane, cyclohexane and pentane. For example, IX139-3 is 38-fold more active on octane than the wildtype enzyme. The rates for hydroxylation of all the liquid alkanes exceed that of wildtype P450 BM-3 on its fatty acid substrates, lauric and palmitic acid (FIG. 14). The evolved enzyme was also 2-fold more active on palmitic acid (FIG. 14), which was surprising since this fatty acid is presumably one of the natural, and optimal, substrates for P450 BM-3. Analysis of the products of reaction with n-alkanes showed hydroxylation at subterminal positions (Table 8), similar to wildtype enzyme's regioselectivity on fatty acids. No further oxidation to diols or ketones was observed. Cyclohexanol was the sole product of hydroxylation of cyclohexane. For the oxidation of octane, hexane, and cyclohexane, the ratio of products formed to dioxygen consumed was 1:1, as determined by GC/MS, and $H_2O_2$ was not detected. This demonstrated that reducing equivalents derived from NADPH result in substrate hydroxylation and the mutant does not waste electrons to produce reduced oxygen intermediates. $H_2O_2$ is not detected for the oxidation of the remaining substrates, and it is assumed that substrate hydroxylation is fully coupled to NADPH oxidation.

Figure 15:
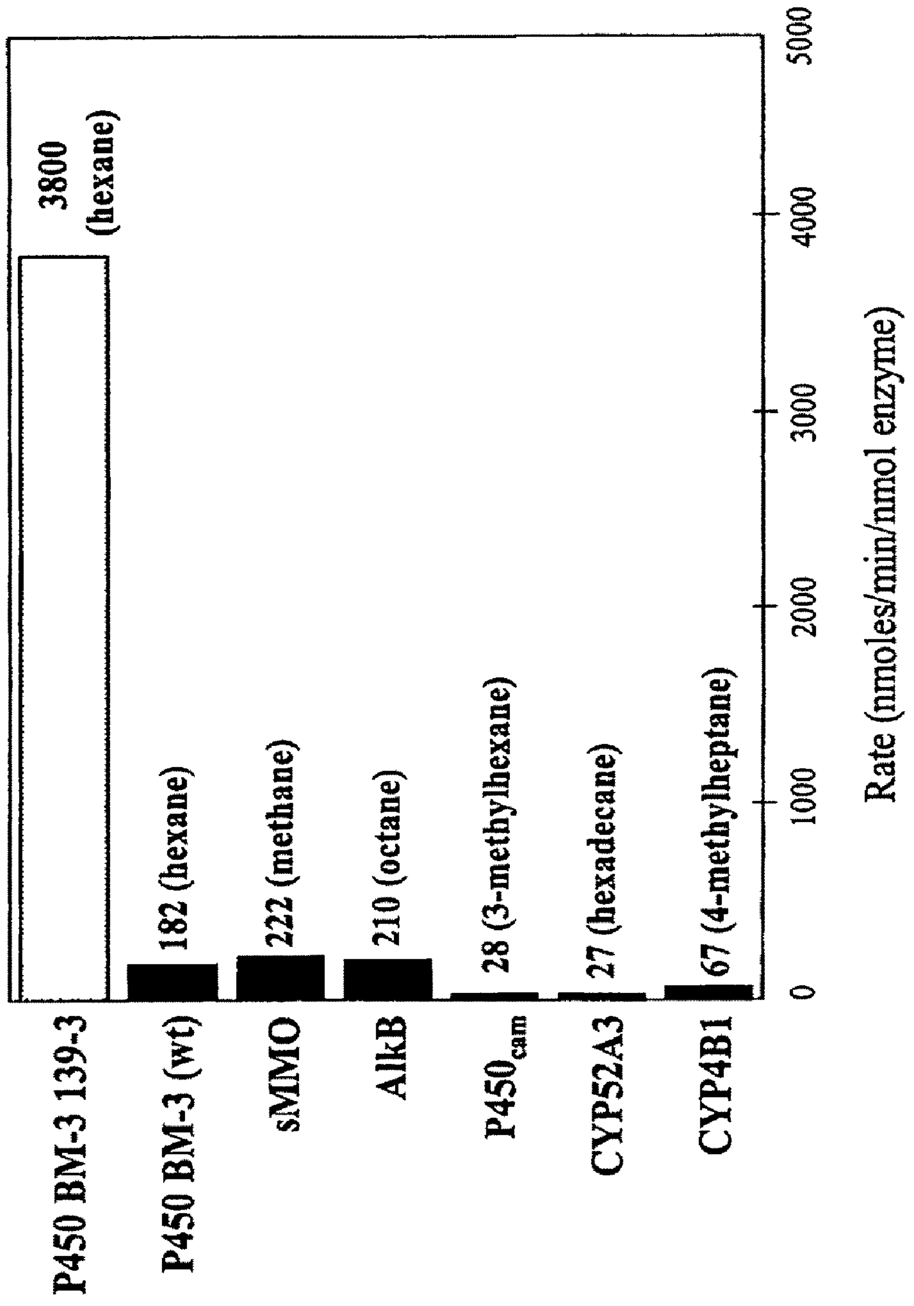
FIG. 15. Maximum rates reported for alkane hydroxylation by alkane monooxygenases CYP4B111, CYP52A38, P450cam9, AIkB18, and sMMO10. Rates for P450 BM-3 wildtype and mutant IX139-3 were determined in this work.

P450 BM-3 IX139-3 is a better catalyst than known, naturally-occurring alkane monooxygenases acting on their most preferred substrates (FIG. 15). For example, the preferred substrate for the non-heme iron alkane monooxygenase (AlkB) from *Pseudomonas oleovorans* is octane; its reported maximal turnover rate is 210 min−1 (Shanklin et al., 1997). In contrast to P450 BM-3, AllcB is membrane-bound and requires two additional proteins, NADPH-rubredoxin reductase and rubredoxin, for catalytic activity. Soluble (sMMO) and particulate methane monooxygenase (pMMO) are large (about 300 kDa), multimeric iron (and in the case of pMMO, iron-copper) enzymes with turnover rates of 200-250 $min^{-}$ for gaseous alkanes (methane, 222 $min^{-1}$) (Fox et al., 1990; Fox et al., 1989; Tonge et al., 1977). Rates on alkanes larger than C4 are much lower (Green and Dalton, 1989). Furthermore, AlkB and MMO have not been produced with high activity in heterologous hosts suitable for protein engineering (Shanklin 1997; Murrell et al., 2000; Staijen et al., 2000). Among the best known of the cytochrome P450 alkane hydroxylases is P450 Cm1 (CYP52 A3), which is involved in alkane metabolization in *Candida maltosa* (Zimmer et al., 1996). This enzyme is also membrane-bound, requires a separate reductase, and has turnover rates lower than AlkB (27 $min^{-1}$ for the purified protein and 40 $min^{-1}$ for microsomal preparations) (Scheller et al., 1996). A number of other P450s also show low levels of activity for alkanes (Stevenson et al., 1996; Fisher et al., 1998; Munro et al., 1993).

From the intriguing possibility that the P450 BM-3 could be engineered to accept the small, gaseous hydrocarbon substrates preferred by MMO, the ability of the IX139-3 mutant to hydroxylate butane and propane was determined. Since the screen identified mutants more active on 8-pnpane and longer-chain alkanes, high activities on propane and butane were not necessarily expected. Based upon NADPH consumption, IX139-3 oxidized butane and propane with initial rates of 1800 and 860 $min^{-1}$, respectively (FIG. 14), which compared favorably to those of the much larger MMO. Comparing with the wildtype, IX139-3 hydroxylates butane and propane 108 and 57 times faster, respectively. The sole products of propane and butane oxidation by P450 BM-3 IX139-3 were 2-propanol and 2-butanol (Table 8).

Figure 16:
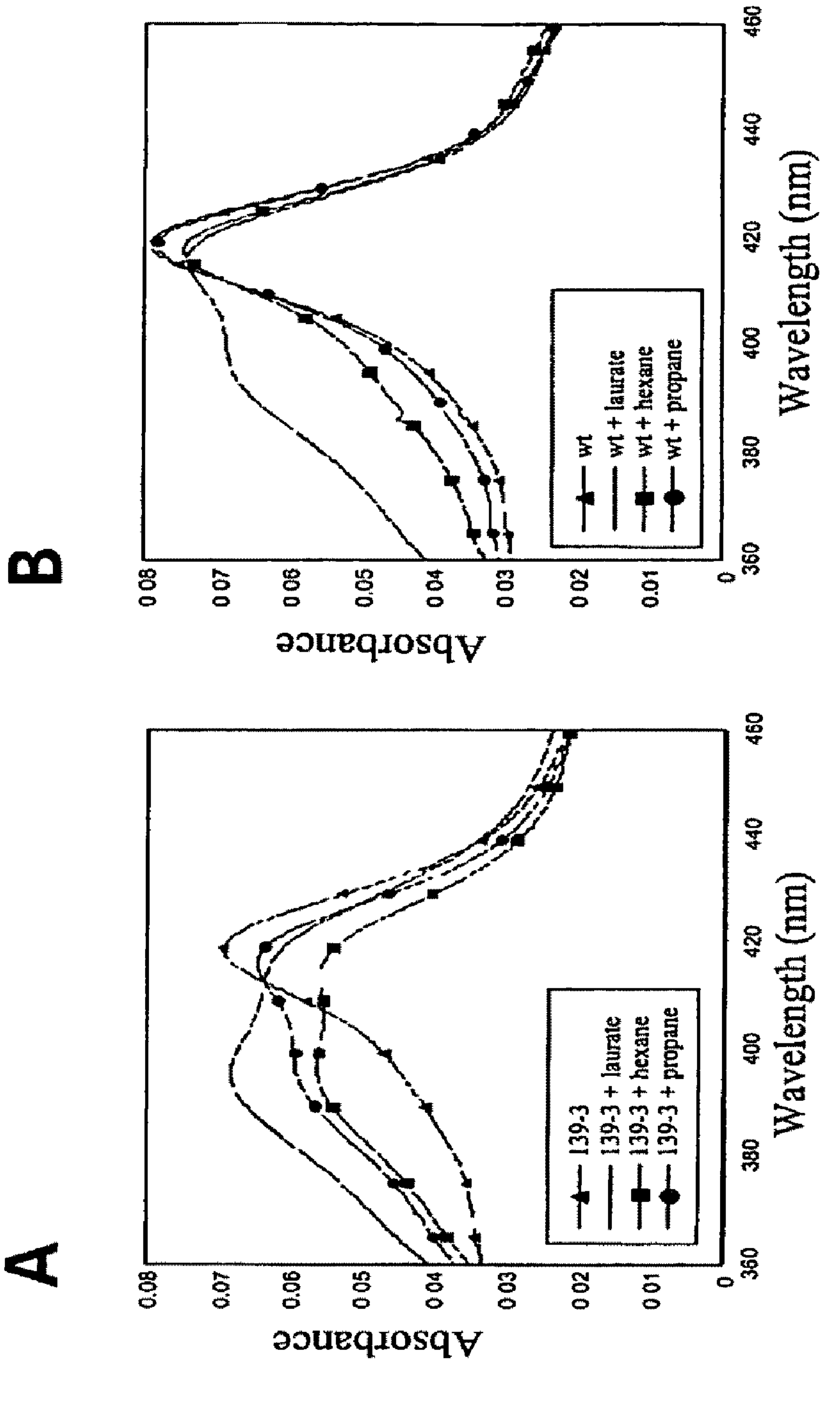
FIGS. 16A and B. Optical spectra for IX139-3 and wild-type P450 BM-3. (A) Mutant IX139-3 (0.5 mM) in potassium phosphate buffer (0.1 M, pH 8) (-▲-); with laurate (0.5 mM, solid line) in 1% methanol; hexane (1.0 mM, -■-) in 1% methanol; propane (saturated solution, -●-). (B) Wildtype P450 BM-3 in potassium phosphate buffer (0.1 M, pH 8) (-▲-); with laurate (0.5 mM, solid line) in 1% methanol; hexane (1.0 mM, 1.0 mM, -■-) in 1% methanol; propane (saturated solution, -●-).

The P450 resting state contains an iron protoporphyin IX as a low-spin six-coordinate ferric species with a dissociable water ligated trans to the proximal cysteinate (Ortiz de Montellano, 1995). Substrate binding displaces water and generates a high-spin five-coordinate species. The spin state shift causes the redox potential of the heme to increase, which activates the protein for hydroxylation. The heme's absorption maximum at 419 nm corresponds to the low-spin species; a shift to 390 nm is characteristic of the high-spin form. This spectral shift is induced in IX139-3 by all the substrates (FIG. 16A), which allowed estimations of $K_d$'s for octane, hexane, and laurate of 10 μM, 27 μM, and 19 μM, respectively. Only the fatty acid substrates produce a spin shift in the wildtype enzyme (laurate: $K_d$=260 μM).

Crystal structures of wildtype P450 BM-3 with and without substrate reveal large conformational changes upon substrate binding at the active site (Haines, D. C., Tomchick, D. R., Machius, M. & Peterson, J. A. Pivotal role of water in the mechanism of P450 BM-3. Biochemistry 40, 13456-13465 (2001); Li, H. Y. & Poulos, T. L. The structure of the cytochrome p450BM-3 haem domain complexed with the fatty acid substrate, palmitoleic acid. Nat. Struct. Biol. 4, 140-146 (1997); Paulsen, M. D. & Ornstein, R. L. Dramatic Differences in the Motions of the Mouth of Open and Closed Cytochrome P450bm-3 by Molecular-Dynamics Simulations. Proteins 21, 237-243 (1995); Chang, Y. T. & Loew, G. Homology modeling, molecular dynamics simulations, and analysis of CYP119, a P450 enzyme from extreme acidothermophilic archaeon Sulfolobus solfataricus. Biochemistry 39, 2484-2498 (2000)).The substrate free structure displays an open access channel with 17 to 21 ordered water molecules. Substrate recognition serves as a conformational trigger to close the channel, which dehydrates the active site, increases the redox potential, and allows dioxygen to bind to the heme. Five of the 11 amino acid substitutions in IX139-3 occur in the region which undergoes the largest conformational change, the F and G helices and the loop connecting them, as well as the I helix across which the F and G helices must slide (FIG. 4). The F and G helices serve as a lid which closes over the substrate access channel upon substrate binding.

Attempts to engineer catalyst specificity are often limited to altering amino acids directly involved in substrate recognition and binding. Only one residue that is in direct contact with substrate in the wildtype enzyme has been mutated in IX139-3 (V78A). Amino acids R47, Y51, F42, and F87 have been proposed to be essential for fatty acid substrate recognition (Noble et al., 1999). R47, Y51, and F42 are located at the mouth of the substrate-binding pocket. R47 and Y51 interact with the substrate carboxylate moiety through electrostatic and hydrogen bonding interactions, while F42 serves as a hatch covering the binding pocket. None of these important residues has been mutated in IX139-3. A salt bridge between R255 and D217 in the substrate free structure can be disrupted by the R255S mutation in IX139-3. This mutation may facilitate conformational changes that permit alkanes to bind more favorably. Rational engineering of the substrate binding pocket of P450 BM-3 produced a triple mutant (F87V, L188Q, A74G) with increased activity for octane (Appel et al., 2001). Directed evolution to produce mutant IX139-3 did not find any beneficial mutations at these sites.

The fact that a few amino acid substitutions can produce a significant increase in P450 BM-3's activity on fatty acids, the presumed biological substrates, indicates that natural selection does not place an advantage on maximizing activity, possibly because such a broadly active enzyme is also toxic to the host organism, as it is to *E. coli*. By evolving the enzyme uncoupled from its biological context we are able to uncover the true catalytic potential of the cytochrome P450. P450 BM-3 mutant IX139-3 is the fastest alkane hydroxylase known. Easily over-expressed in *E. coli*, soluble and requiring no additional electron transfer proteins for catalysis, this enzyme should prove an attractive catalyst for selective hydrocarbon oxidation.

Example 4

Alkene Oxidation for P450 BM-3 Mutant IX139-3

Epoxidation of alkenes is an important reaction in organic synthesis since they are important chemical building blocks. The oxirane ring is subject to ring opening by various nucleophiles (oxygen, sulfur, nitrogen, carbon), which yield bifunctional compounds (Carey and Sundberg, 1990). In the chemical industry, epoxides are used in the production of polymers (polyether polyols), as well as glycols, polyglycols, and alkanolamines. Optically pure epoxides are useful intermediates in the synthesis of pharmaceuticals, agrochemicals, perfumes, and liquid crystals where chirality plays a critical role in function. Great efforts in developing chemical catalyst for alkene epoxidation has resulted in limited successes (Jacobson, 1993; White et al., 2001). The main limitations of chemical methods for alkene epoxidation is poor catalytic efficiencies for trans and terminal olefins (Faber, 2000). Furthermore, chemical methods produce large amounts of toxic byproducts. For example, the current industrial processes for the synthesis of propylene oxide from propene use large amounts of $Cl_2$ that lead to equipment corrosion and toxic byproducts. Monooxygenases provide an alternative to chemical means for epoxidation (Schmid et al., 2001).

The mutant IX139-3 was shown to have broad substrate specificity for alkanes with varying chain length (C8-C3). Furthermore, the variant was also shown to be more active on fatty acids. The activity for alkenes was also investigated, and the mutant is also more efficient in alkene oxidation. IX139-3 may prove to be a general catalyst for hydrocarbon oxidation, and it may find uses in the fine chemical industry as well as in bioremediation.

Materials and Methods

All chemical reagents were procured for Aldrich, Sigma, or Fluka.

Expression of P450 BM-3 Mutant

See example 1. A. Expression and purification of p450 BM-3 variants

Determination of the Maximum Initial Rate for Alkene Oxidation

The enzyme was purified and quantified as described above. A typical reaction solution contained enzyme (1.0 ml, 1 μM), alkene (10 μL, 1.0 mM), and methanol (1%) in potassium phosphate buffer (0.1 M, pH 8.0). The solution was incubated at room temperature, and the reaction was initiated by the addition of NADPH (200 μL, 200 μM). The rate of NADPH oxidation was monitored at 340 nm.

Substrate Conversion and Product Characterization

A typical reaction contained purified enzyme (1.0 ml, 1 μM), alkene (10 μL, 1.0 mM), and methanol (1%) in phosphate buffer (0.1 M, pH 8.0). The solution was incubated at room temperature for 5 minutes, and the reaction was initiated by the addition of NADPH (200 μL, 200 μM). The solution was allowed to stir aerobically at room temperature for 30 minutes. For propene oxidation, the reaction contained enzyme (3.0 ml, 1.0 μM) in potassium phosphate buffer (0.1 M, pH 8.0), and the resulting solution was sealed in a 20 ml vial with a septum. The head-space was filled with propene and the reaction was initiated by the addition of NADPH (100 μl, 0.5 mM). The reaction was stirred at room temperature for 1.5 hours.

The products were analyzed by gas chromatography/mass spectrometry using an Hewlett Packard HP 6890 series gas chromatograph coupled with an Hewlett Packard 5973 mass selective detector). The GC was fitted with a HP FFAP column (crosslinked FFAP, 30 m×0.25 mm×0.25 μm film thickness). The condition for propene is as follows: (1) 35° C. for 1.7 minutes. (2) 35 to 200° C. at 20° C./min. (3) 200° C. for 1 minute. The condition for styrene, cyclohexene, and 1-hexene is as follows: (1) 100° C. for 4.5 minutes. (2) 100 to 200° C. at 20° C./min. (3) 200 for 7.0 minutes. Authentic standards were used to identify the products by retention time. Products were further verified by matching the fragmentation distributions with a database in the software provided by the instrument manufacturer.

4-(1-Nitrobenzyl)pyridine Assay

A typical reaction contained enzyme (1.0 ml, $1\times10^{-6}$ M) in potassium phosphate buffer (0.1 M, pH 8.0), alkene ($1.0\times10^{-3}$ M), and methanol (1%) in a vial. The reaction was initiated with NADPH (50 μl, $\mathbf{1.0\times10^{-3}}$ M), and allowed to stir aerobically for 5 minutes. 300 μl of a stock solution of 4-(4-nitrobenzyppyridine (5% w/w in acetone) was added to the reaction, and the vial was sealed. The reaction was incubated at 80° C. for 20 minutes and chilled on ice. 600 μl of an ethylacetate/acetone (5:2) solution and 300 μl 5 M aqueous NaOH was added to the reaction solution. The solution was mixed thoroughly, and the absorbance of the organic layer was measured at 540 nm in a glass 96-well plate with microplate spectrophotometer.

Substrate Binding

See Example 3: Substrate binding.

Results and Discussion

P450 BM-3 is known to form epoxides from various substrates that vary in size and structure (Martinez and Stewart, 2000; Fruetel et al., 1994; Capdevila et al., 1996; Ruettinger and Fulco, 1981; Schneider et al., 1999). For example, P450 BM-3 oxidizes arachidonic acid to 18(R)-hydroxyeicosatetraenoic acid and 14(S),15(R)-epoxyeicosatrienoic acid (80 and 20% of total products, respectively), and eicosapentaenoic acid to 17(S),18(R)-epoxyeicosatetraenoic acid (99% total products) (Capdevila et al., 1996). Furthermore, stryene is oxidized solely to styrene oxide (Fruetel et al., 1994).

Figure 17:
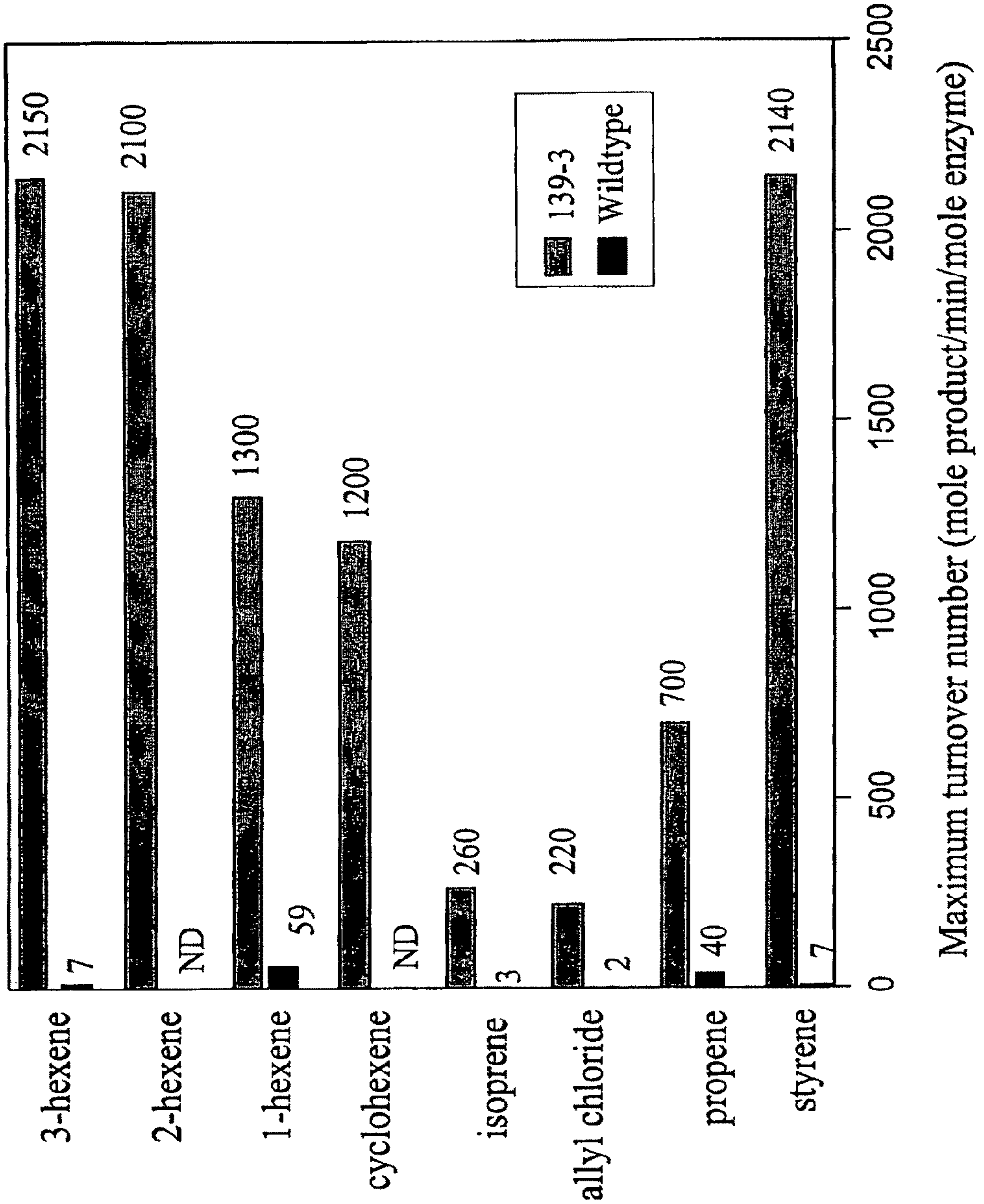
FIG. 17. Initial rates of NADPH consumption (mole substrate/min/mole enzyme) in the presence of alkenes for wild-type (black bars) and 1X139-3 (shaded bars). "ND" indicates that NAPDH consumption was not detectable over background.

The evolved enzyme IX139-3 has been shown to be highly active for alkane and fatty acid oxidation (see above). Interestingly, the initial rates of NADPH consumption in the presence of alkenes were also very high (FIG. 17). For example, the rate of cyclohexene and styrene is 1200 and 300 fold more active than wildtype, respectively. For all the alkenes investigated, $H_2O_2$ is not detected and the enzyme is assumed to be fully coupled. However, there is a possibility that $H_2O$ can be produced, which can only be accurately determined by quantitating product formation.

Figure 18:
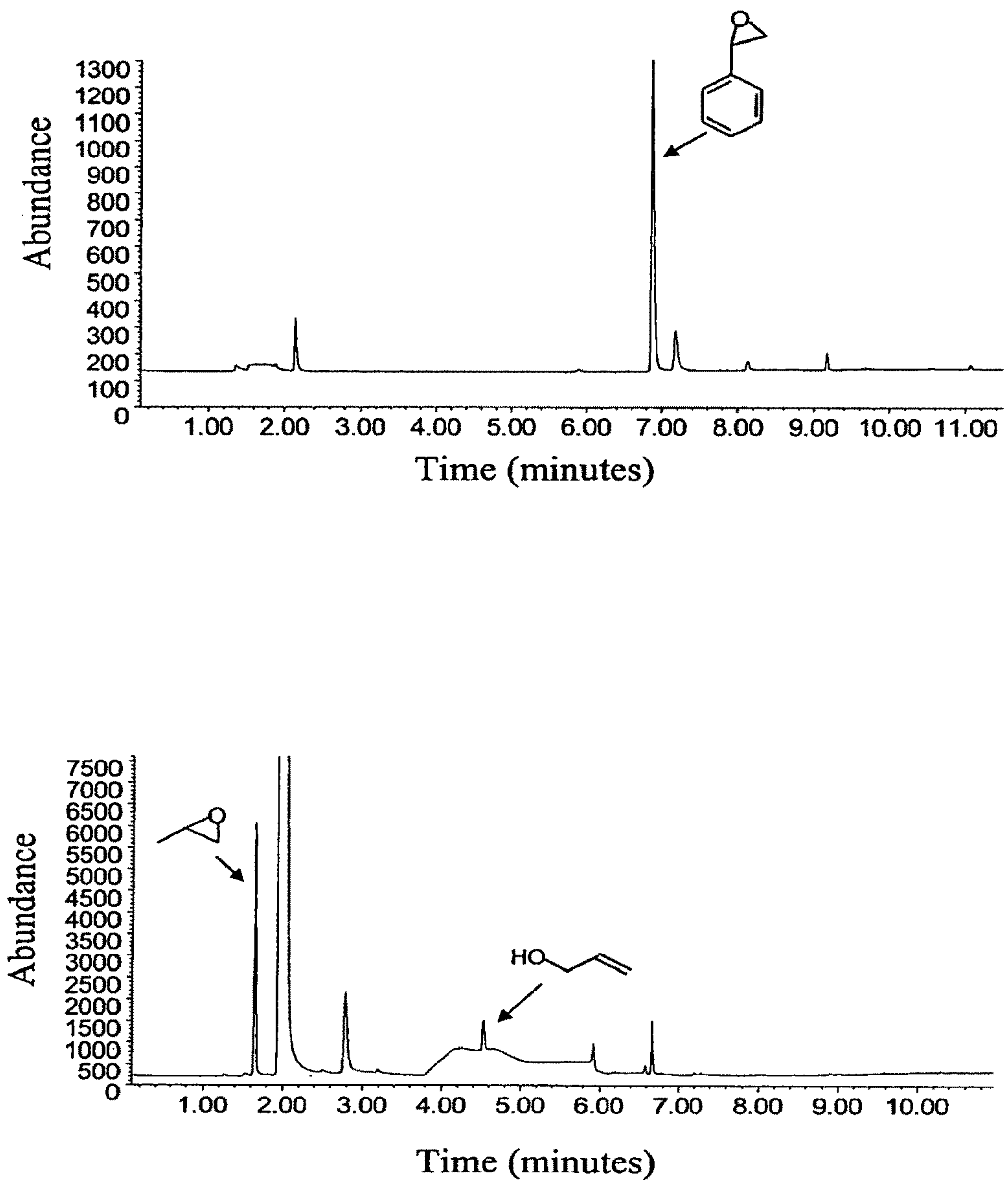
FIG. 18. Gas chromatogram of the oxidation products of styrene (A) and propene (B) catalyzed by IX139-3.

The products for styrene, propene, cyclohexene, and 1-hexene were characterized by gas chromatography/mass spectrometry. The sole product for stryene was styrene oxide, which is similar to what is found for the wildtype (Martinez et al., 2000). The major product from propene oxidation is propene oxide and allyl alcohol is only a minor species. Propene oxidation has not been previously reported by P450 BM-3 (See FIG. 18).

The products for styrene, propene, cyclohexene, and 1-hexene were characterized by gas chromatography/mass spectrometry. The sole product for stryene was styrene oxide, which is similar to what is found for the wildtype (Fruetel et al., 1994). The products from propene oxidation is propene oxide and allyl alcohol. Propene oxidation has not been previously reported by P450 BM-3.

GC/MS analysis of cyclohexene oxidation by IX139-3 revealed two products, cyclohexene oxide and 1,2-cyclohexane diol. The sole product of the bioconversion was most likely cyclohexene oxide, and 1,2-cyclohexane diol probably occured via base-catalyzed hydrolysis of cyclohexene oxide (see reaction conditions) (March, 1992). Cyclohexene oxide was converted to 1,2-cyclohexane diol in potassium phosphate buffer (0.1 M, pH 8.0), as verified using GC/MS.

No epoxidation of 1-hexene was detected, and the product was 1-hexene-3-ol, which results from hydroxylation at the allylic position. This was expected since wildtype P450 BM-3 preferentially oxidizes fatty acids with a terminal double bond at the ω-2 position and the corresponding terminal epoxide is not formed (Shirane et al., 1993). The selectivity may be due to the C—H bond strength. The ω-2 secondary allylic (DH° 298 ~83 kcal/mol) C—H are weaker than the ω-3 secondary (DH° 298 ~98 kcal/mol) C—H bond. However, a terminal double bond should also be oxidized unless there is a mechanistic or steric factor. P450 BM-3 is known to form the corresponding epoxide from cis-9-hexadecenoic acid as well as hydroxylated products (Ruettinger and Fulco, 1981), which demonstrates that there is no mechanistic restraint. Hence, a steric restraint exist that hinders terminal epoxidation. This is further supported by the fact terminal oxidation of fatty acids and alkanes are not observed.

Figure 19:
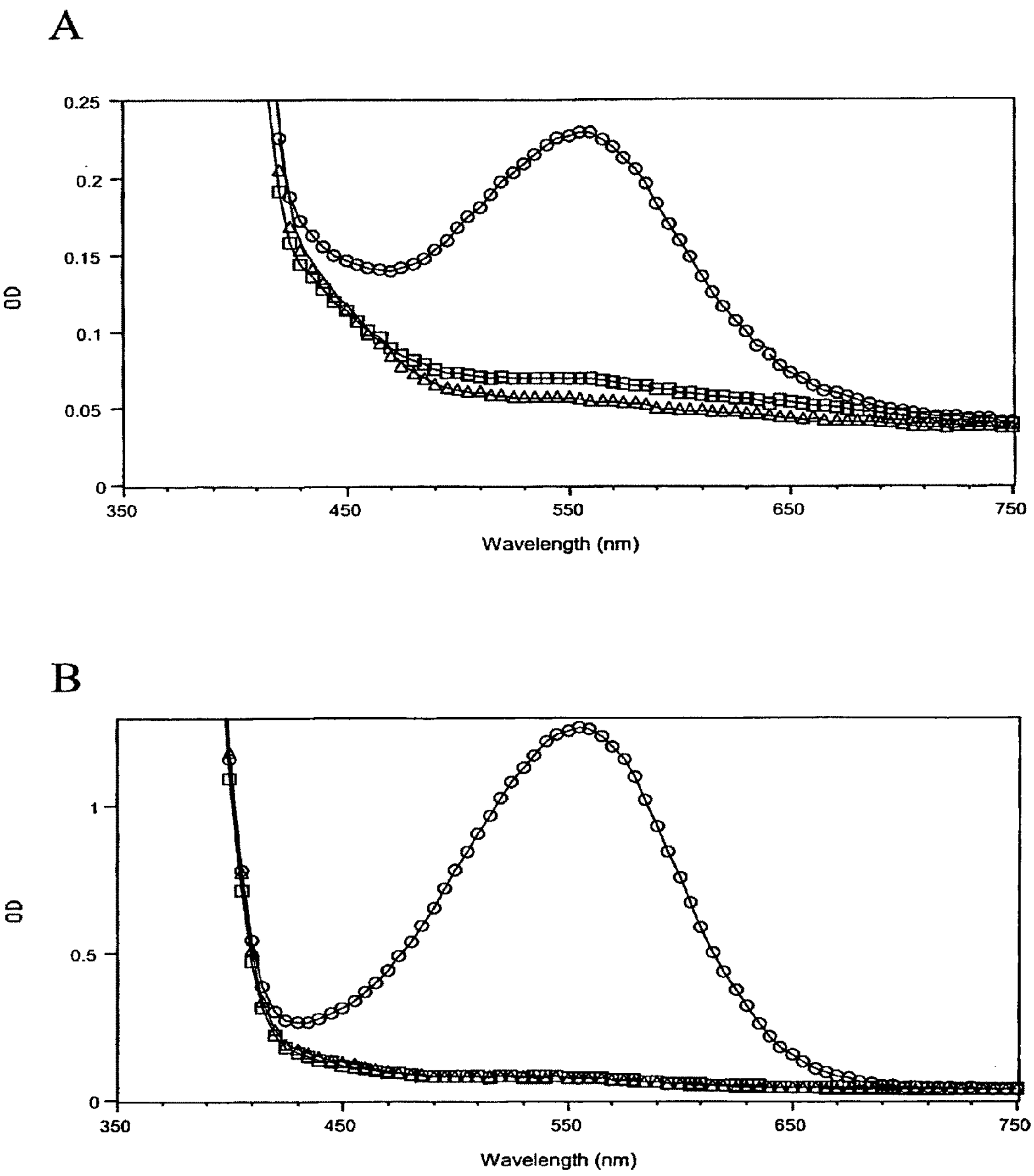
FIGS. 19A and B. (A) Absorption spectra in the presence of IX139-3 after the 4-NBP assay with isoprene and NADPH (○), NADPH without isoprene (□), and isoprene without NADPH (Δ). (B) Absorption spectra in the presence of IX139-3 after the NBP assay with styrene and NADPH (○), NADPH without styrene (□), and styrene without NADPH (Δ).
Figure 21A:
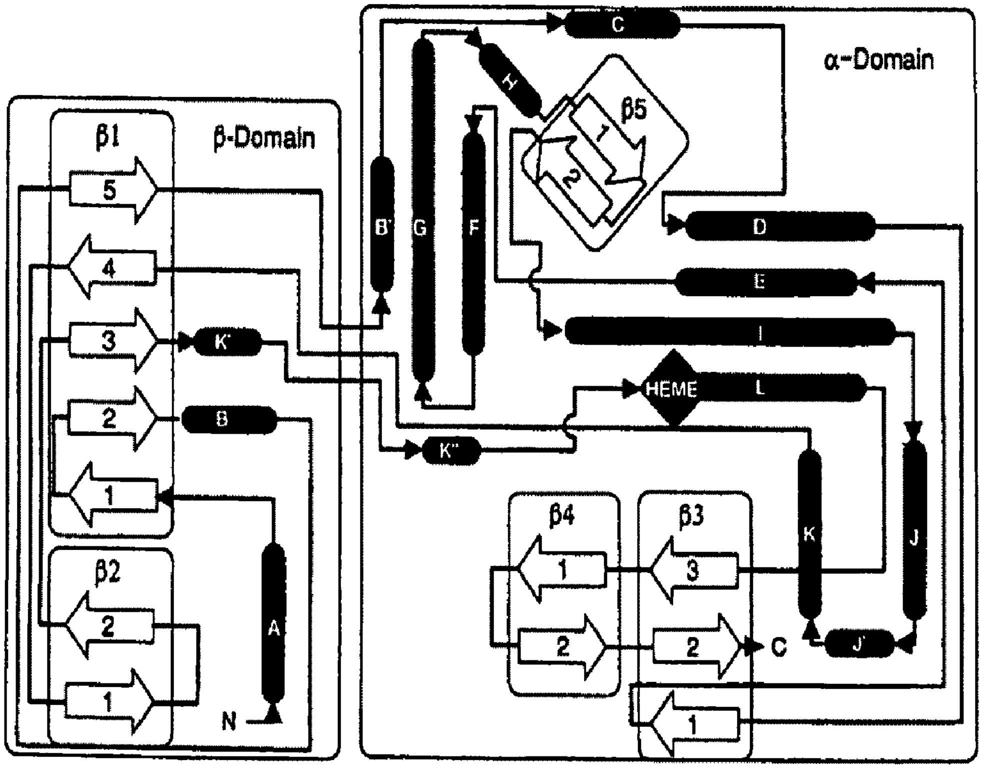
FIGS. 21A to F. Representative topology diagrams of the heme domain of P450 variants of the invention, based on P450BM-P; the heme domain of P450 BM-3: (A) topology of P450BM-P; the topology is depicted with helices represented by black bars, and the length of each of the bars is in approximate proportion to the length of the helix. The strands of β-sheets are shown with arrows. The strands are grouped by the secondary structural elements which they comprise. The structural elements are grouped into the α-helical-rich domain and the β-sheet-rich domain. The heme is shown by the square at the $NH_2$-terminal end of the L-helix. With only minor modifications, this topology diagram could be used for other P450s (Peterson et al., 1995). (B) Topology of P450 BM-3, showing location of the heme group. (C) Location of residues H138 and A78 relative to the heme group. (D) Location of residues T175, V178, A184, N186, and D217 relative to the heme. (E) Location of residues H236, R255, and E252 relative to the heme. (F) Location of residues L353, G396, A290, and A295 relative to the heme. Those sections labeled A, beta1, beta3, beta4, D, E, F, G, I, K, and J denote secondary structural elements conserved in P450s.
Figure 21B:
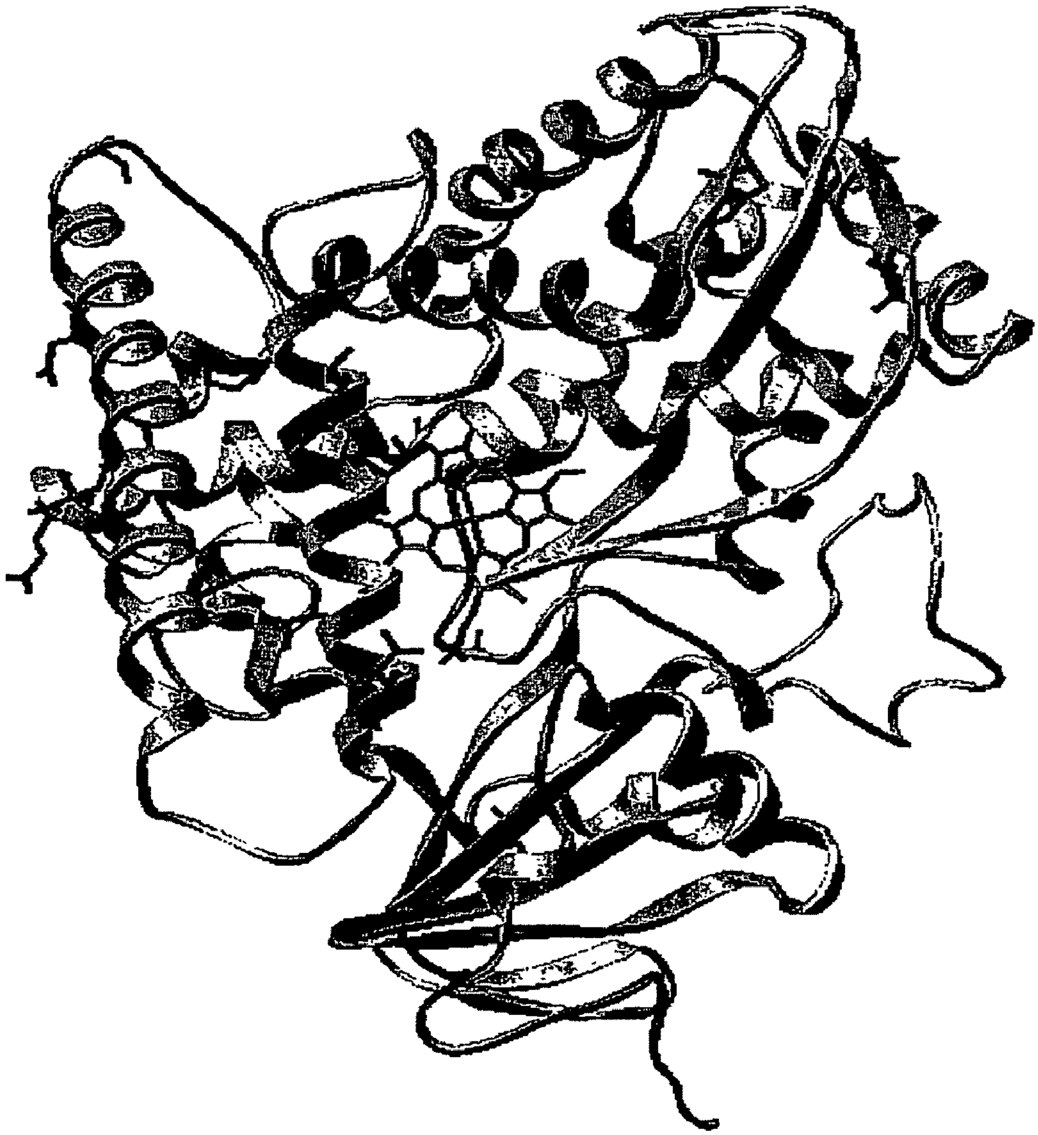
Figure 21C:
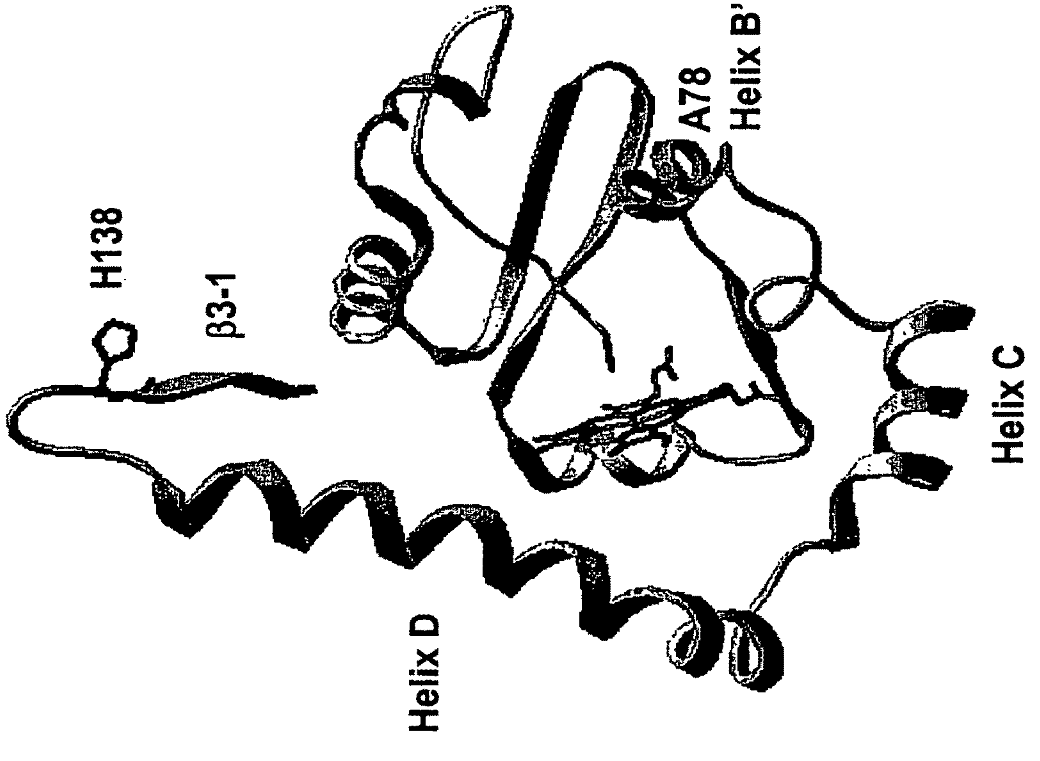
Figure 21D:
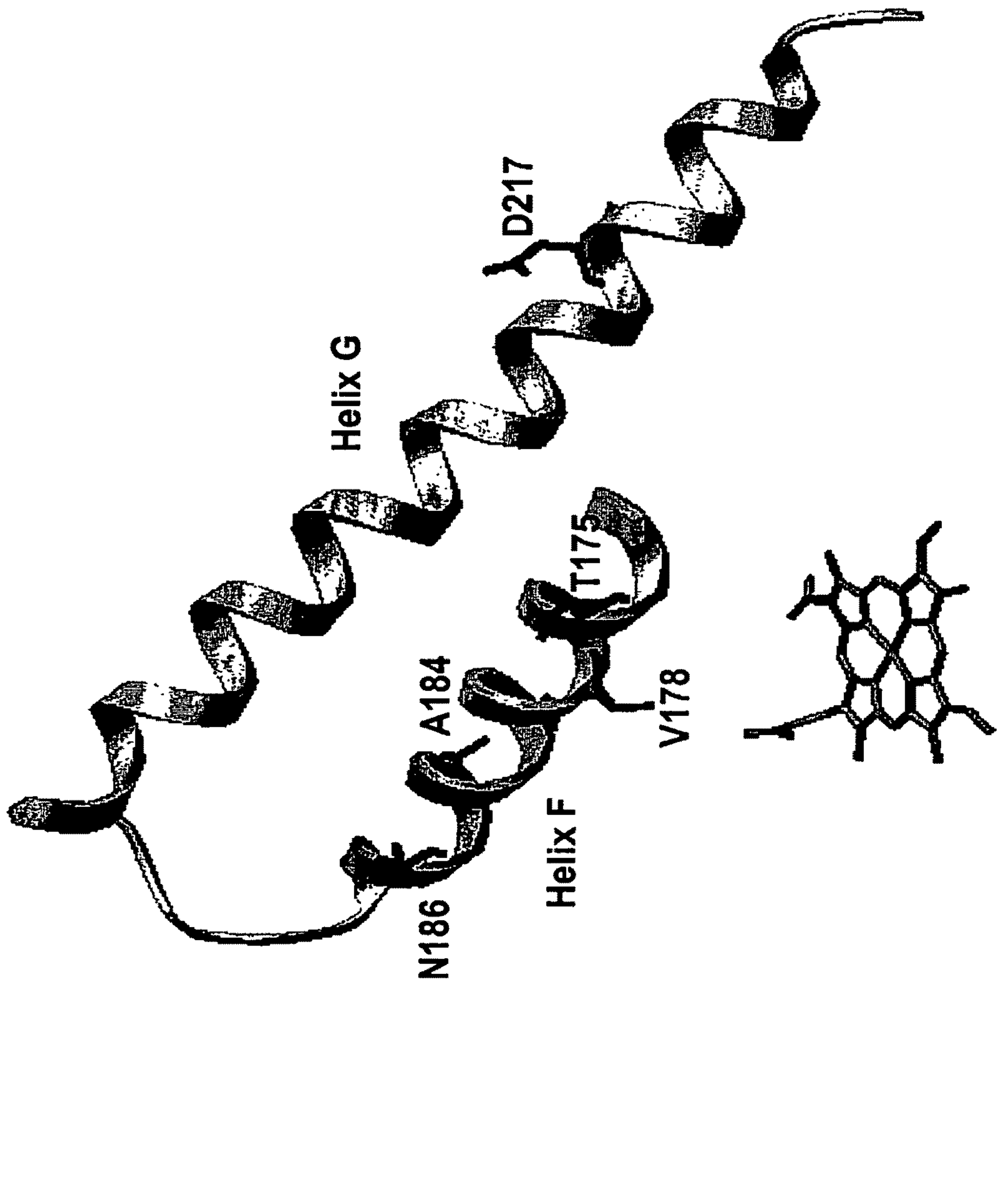
Figure 21E:
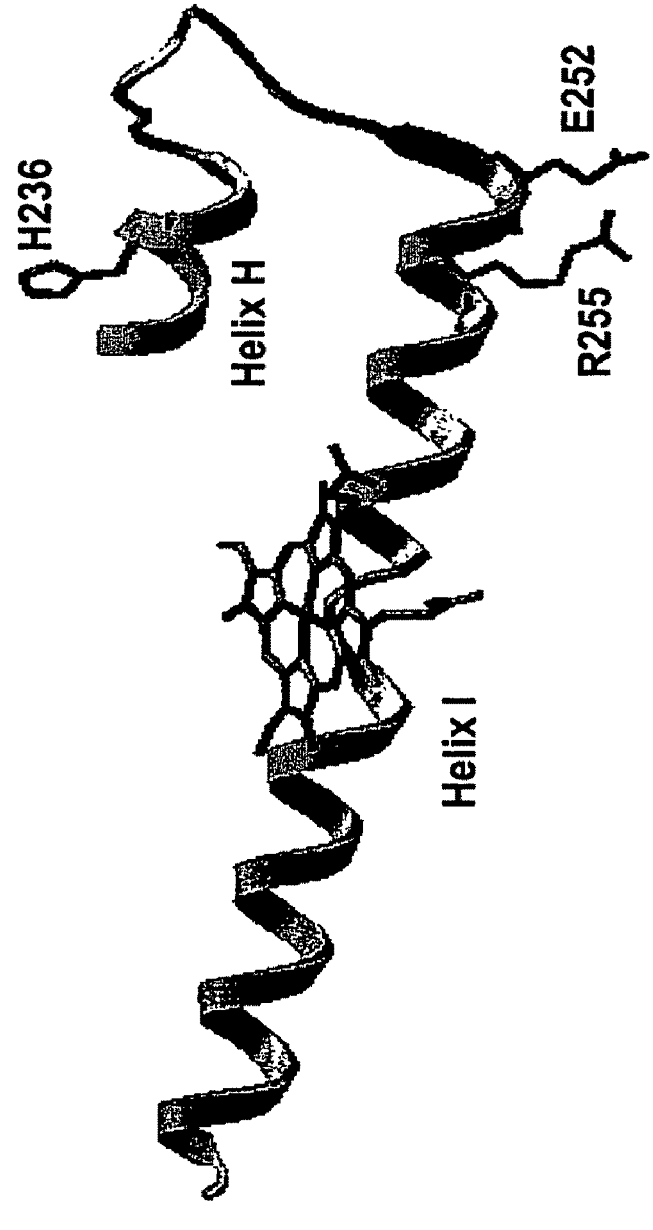
Figure 21F:
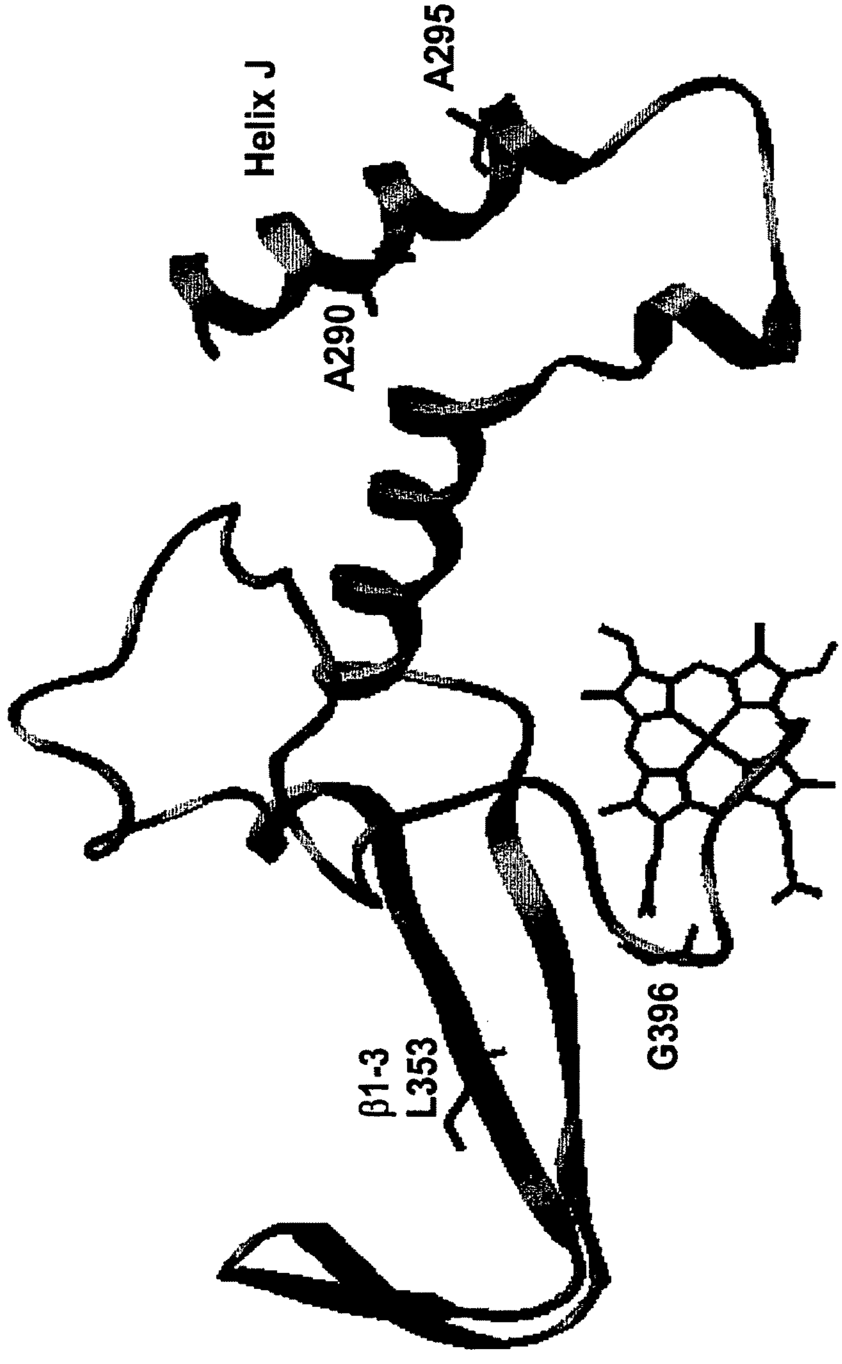
Figure 22:
FIG. 22. Positions of the amino acid substitutions in P450 BM-3 mutant IX139-3. The variant contains 11 amino acid substitutions, which are represented as spheres on the crystal structure of the substrate-bound enzyme (PDB: 1FAG). Five are clustered on the highly flexible F-G helix-loop-helix structure and the I helix along which it slides during substrate binding and release.

The 4-(nitrobenzyl)pyridine (4-NBP) (Kim and Thomas, 1992) assay was used to determine epoxide formation for allyl chloride, isoprene, 2-hexene and 3-hexene since the corresponding epoxides were not available as standards. Nucleophilic attack of the oxirane ring by 4-NBP results alkylation, and the product results in a purple colored ($Abs_{max}$~550 nm) species. IX139-3 in the presence of isoprene, dioxygen and NADPH forms the alkylated product (FIG. 19) with a $\lambda_{max}$~550 nm. Similar results occur when allyl chloride is the substrate. The color develops only when enzyme, substrate, and NADPH are present. If any of the components are missing then no color is formed. Control experiments with IX139-3, styrene, and NADPH, which is shown to form styrene oxide as determined by GC/NIS, also test positive using the 4-NBP assay. When either 2-hexene or 3-hexene are used as substrates, no alkylation product is formed, and it is assumed that the alkene is hydroxylated.

139-3 in the presence of alkenes induces small spin state shifts. Whereas, the wildtype in presence does not produce a spin state shift. This indicates that the substrate binding properties have been altered. IX139-3 is very active for alkane hydroxylation, fatty acid oxidation and alkene epoxidation, and the substrate specificity is broad. This mutant may be useful a general catalyst for hydrocarbon oxidation. The mutant may be useful for fine chemical synthesis when only one product is detected such as styrene oxide. Alternatively, the mutant may find applications in bioremediation when more than one product is generated.

General Definitions

The following defined terms are used throughout the present specification, and should be helpful in understanding the scope and practice of the present invention.

"Cytochrome P450 monooxygenase" or "P450 enzyme" means an enzyme in the superfamily of P450 haem-thiolate proteins, which are widely distributed in bacteria, fungi, plants and animals. The enzymes are involved in metabolism of a plethora of both exogenous and endogenous compounds. Usually, they act as oxidases in multicomponent electron transfer chains, called here P450-containing monooxygenase systems. The unique feature which defines whether an enzyme is a cytochrome P450 enzyme is the reduced form of the enzyme which binds carbon monoxide and results in a characteristic absorption maximum at 450 nm. Reactions catalyzed by cytochrome P450 enzymes include epoxidation, N-dealkylation, O-dealkylation, S-oxidation and hydroxylation. The most common reaction catalyzed by P450 enzymes is the monooxygenase reaction, i.e., insertion of one atom of oxygen into a substrate while the other oxygen atom is reduced to water. Although any P450 enzyme can be modified according to the invention, the following are non-limiting examples of preferred P450 enzymes: P450 BM-3 (GenBank Accession Nos. J04832 (SEQ ID NO:1) and P14779 (SEQ ID NO:2)); CYP 2C3 (GenBank P00182, SEQ ID NO:3); CYP 2C9 (GenBank P11712; SEQ ID NO:4), CYP 2D1v (GenBank P10633; SEQ ID NO:5), and CYP 108 (GenBank P33006; SEQ ID NO:6).

An "oxidation", "oxidation reaction", or "oxygenation reaction", as used herein, is a chemical or biochemical reaction involving the addition of oxygen to a substrate, to form an oxygenated or oxidized substrate or product. An oxidation reaction is typically accompanied by a reduction reaction (hence the term "redox" reaction, for oxidation and reduction). A compound is "oxidized" when it receives oxygen or loses electrons. A compound is "reduced" when it loses oxygen or gains electrons. An oxidation reaction can also be called an "electron transfer reaction" and encompass the loss or gain of electrons (e.g., oxygen) or protons (e.g., hydrogen) from a substance. Non-limiting examples of oxidation reactions include hydroxylation (e.g., $RH+O_2+2H^++2e^-\rightarrow ROH+H2O$), epoxidation ($RCH{=}CHR'+2H^++O_2+2e^-\rightarrow RCHO-CHR'+H_2O$), and ketone formation ($RCH_2R'\rightarrow RCOR'$).

A "co-solvent" or "indirect solvent" herein means a non-solvent that becomes an acceptable solvent or co-solvent when a small amount of active solvent is added. For example, water is a non-solvent for various hydrophobic substances, but the addition of a water-miscible solvent such as DMSO, tetrahydrofuran (THF), methanol, ethanol, propanol, dioxane, or dimethylformamide (DMF), or other solvents known in the art, increases the solubility of hydrophobic compounds in the mixture.

The "organic solvent resistance" of an enzyme means its ability to function, optionally function over time, in an organic solvent or in a co-solvent. One way to evaluate organic solvent resistance is to assess the ability of the enzyme to resist a loss of activity over time, in one or more co-solvent systems . A more "organic-solvent resistant" enzyme can be one that is more resistant to loss of structure (unfolding) or function (enzyme activity) when exposed to an organic solvent or co-solvent. Preferred systems for testing organic solvent resistance include water/DMSO and water/THF mixtures, for example, 10% (v/v) DMSO and 2% (v/v/) THF.

"Alkane-oxidation capability" herein means the capability of a cytochrome P450 enzyme to oxidize at least one alkane. The alkane-oxidation capability of an enzyme can be evaluated, for example, by mixing the enzyme with an alkane in the presence of any necessary co-factors, and evaluate whether the alkane is oxidized. In particular, the capability of a cytochrome P450 variant to oxidize an alkane can be related to the capability of the corresponding wild-type P450 to oxidize the same alkane, e.g., by comparing maximum turnover rate, total amount of product formed, or any other suitable measure of enzyme activity. Many examples of alternative assays are provided herein. Preferred alkanes for which alkane-oxidation capability can be evaluated include 8-pnpane, octane, hexane, cyclohexane, propane, ethane, and/or butane.

"Alkene-oxidation capability" herein means the capability of a cytochrome P450 enzyme to oxidize at least one alkene. The alkene-oxidation capability of an enzyme can be evaluated, for example, by mining the enzyme with an alkene in the presence of any necessary co-factors, and evaluate whether the alkene is oxidized to form an epoxide or hydroxylated product. In particular, the capability of a cytochrome P450 variant to oxidize an alkene can be related to the capability of the corresponding wild-type P450 to oxidize the same alkene, e.g., by comparing maximum turnover rate, total amount of product formed, or any other suitable measure of enzyme activity. Many examples of alternative assays are provided herein. Preferred alkenes for which alkane-oxidation capability can be evaluated include octene, hexene, propene, ethene, and/or butene.

The term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Molecular Biology Definitions

In accordance with the present invention there may be employed conventional molecular biology, microbiology, and recombinant DNA techniques within the skill of the art. Such techniques are explained fully in the literature: See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B .D. Hames & S. J. Higgins eds. (1985)); Transcription And Translation (B. D. Haines & S. J. Higgins, eds. (1984)); Animal Cell Culture (R. I. Freshney, ed. (1986)); Immobilized Cells And Enzymes (IRL Press, (1986)); B. Perbal, A Practical Guide To-Molecular Cloning (1984); P. M. Ausubel et al. (eds.), Current Protocols in Molecular Biology, John Wiley & Sons, Inc. (1994).

A "protein" or "polypeptide", which terms are used interchangeably herein, comprises one or more chains of chemical building blocks called amino acids that are linked together by chemical bonds called peptide bonds.

An "enzyme" means any substance, preferably composed wholly or largely of protein, that catalyzes or promotes, more or less specifically, one or more chemical or biochemical reactions. The term "enzyme" can also refer to a catalytic polynucleotide (e.g. RNA or DNA).

A "native" or "wild-type" protein, enzyme, polynucleotide, gene, or cell, means a protein, enzyme, polynucleotide, gene, or cell that occurs in nature.

A "parent" protein, enzyme, polynucleotide, gene, or cell, is any protein, enzyme, polynucleotide, gene, or cell, from which any other protein, enzyme, polynucleotide, gene, or Cell, is derived or made, using any methods, tools or techniques, and whether or not the parent is itself native or mutant. A parent polynucleotide or gene encodes for a parent protein or enzyme.

A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon. Table 9 outlines which amino acids correspond to which codon(s).

TABLE 9

Amino Acids, Corresponding Codons, and Functionality

| Amino Acid | SLC | DNA codons | Side Chain Property |
|---|---|---|---|
| Isoleucine | I | ATT, ATC, ATA | Hydrophobic |
| Leucine | L | CTT, CTC, CTA, CTG, TTA, TTG | Hydrophobic |
| Valine | V | GTT, GTC, GTA, GTG | Hydrophobic |
| Phenylalanine | F | TTT, TTC | Aromatic side chain |
| Methionine | M | ATG | Sulphur group |
| Cysteine | C | TGT, TGC | Sulphur group |
| Alanine | A | GCT, GCC, GCA, GCG | Hydrophobic |
| Glycine | G | GGT, GGC, GGA, GGG | Hydrophobic |
| Proline | P | CCT, CCC, CCA, CCG | Secondary amine |
| Threonine | T | ACT, ACC, ACA, ACG | Aliphatic hydroxyl |
| Serine | S | TCT, TCC, TCA, TCG, AGT, AGC | Aliphatic hydroxyl |
| Tyrosine | T | TAT, TAC | Aromatic side chain |
| Tryptophan | W | TGG | Aromatic side chain |
| Glutamine | Q | CAA, CAG | Amide group |
| Asparagine | N | AAT, AAC | Amide group |
| Histidine | H | CAT, CAC | Basic side chain |
| Glutamic acid | E | GAA, GAG | Acidic side chain |
| Aspartic acid | D | GAT, GAC | Acidic side chain |
| Lysine | K | AAA, AAG | Basic side chain |
| Arginine | R | CGT, CGC, CGA, CGG, AGA, AGG | Basic side chain |
| Stop codons | Stop | TAA, TAG, TGA | — |

"Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge (see Table 9).

Amino acids other than those indicated as conserved may differ in a protein or enzyme so that the percent protein or amino acid sequence similarity between any two proteins of similar function may vary and can be, for example, at least 70%, preferably at least 80%, more preferably at least 90%, and most preferably at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using all of these programs, the preferred settings are those that results in the highest sequence similarity.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. Preferred activity units for expressing activity include the catalytic constant ($k_{cat}=v_{max}/E$; Vmax is maximal turnover rate; E is concentration of enzyme); the Michaelis-Menten constant ($K_m$); and $k_{cat}/K_m$. Such units can be determined using well-established methods in the art of enzymes.

The "stability" or "resistance" of an enzyme means its ability to function, over time, in a particular environment or under particular conditions. One way to evaluate stability or resistance is to assess its ability to resist a loss of activity over time, under given conditions. Enzyme stability can also be evaluated in other ways, for example, by determining the relative degree to which the enzyme is in a folded or unfolded state. Thus, one enzyme has improved stability or resistance over another enzyme when it is more resistant than the other enzyme to a loss of activity under the same conditions, is more resistant to unfolding, or is more durable by any suitable measure. For example, a more "organic-solvent" resistant enzyme is one that is more resistant to loss of structure (unfolding) or function (enzyme activity) when exposed to an organic solvent or co-solvent.

The term "substrate" means any substance or compound that is converted or meant to be converted into another compound by the action of an enzyme catalyst. The term includes aromatic and aliphatic compounds, and includes not only a single compound, but also combinations of compounds, such as solutions, mixtures and other materials which contain at least one substrate. Preferred substrates for hydroxylation using the cytochrome P450 enzymes of the invention include alkanes such as propane, ethane, butane, pentane, hexane, cyclohexane, and octane, and alkane derivatives such as alkanes substituted with one or more chemical group such as nitro-, sulphur-, halogen- and oxygen-containing groups, as well as aromatic groups, e.g., p-nitrophenoxyoctane (8-pnpane). Preferred substrates for epoxidation include alkenes such as propene, ethene, butene, pentene, hexene, cyclohexene, octene, as well as alkene derivatives, which are alkanes substituted with or linked to chemical substituents such as nitro-, sulphur-, halogen- and oxygen-containing groups, and/or aromatic groups.

The term "cofactor" means any non-protein substance that is necessary or beneficial to the activity of an enzyme. A "coenzyme" means a cofactor that interacts directly with and serves to promote a reaction catalyzed by an enzyme. Many coenzymes serve as carriers. For example, NAD+ and NADP+ carry hydrogen atoms from one enzyme to another. An "ancillary protein" means any protein substance that is necessary or beneficial to the activity of an enzyme.

The terms "oxygen donor", "oxidizing agent" and "oxidant" mean a substance, molecule or compound which donates oxygen to a substrate in an oxidation reaction. Typically, the oxygen donor is reduced (accepts electrons). Exemplary oxygen donors, which are not limiting, include molecular oxygen or dioxygen ($O_2$) and peroxides, including alkyl peroxides such as t-butyl peroxide, and most preferably hydrogen peroxide ($H_2O_2$). A peroxide is any compound having two oxygen atoms bound to each other by a single bond, i.e., dioxygen ($O_2$) has a double bond between the oxygen atoms.

An "oxidation enzyme" is an enzyme that catalyzes one or more oxidation reactions, typically by adding, inserting, contributing or transferring oxygen from a source or donor to a substrate. Such enzymes are also called oxidoreductases or redox enzymes, and encompasses oxygenases, hydrogenases or reductases, oxidases and peroxidases. An "oxidase" is an oxidation enzyme that catalyzes a reaction in which molecular oxygen (dioxygen or $O_2$) is reduced, for example by donating electrons to (or receiving protons from) hydrogen.

A "luminescent" substance means any substance which produces detectable electromagnetic radiation, or a change in electromagnetic radiation, most notably visible light, by any mechanism, including color change, UV absorbance, fluorescence and phosphorescence. Preferably, a luminescent substance according to the invention produces a detectable color, fluorescence or UV absorbance. The term "chemiluminescent agent" means any substance which enhances the detectability of a luminescent (e.g., fluorescent) signal, for example by increasing the strength or lifetime of the signal.

A "polynucleotide" or "nucleotide sequence" is a series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and antisense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and intemucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.).

A "coding sequence" or a sequence "encoding" a polypeptide, protein or enzyme is a nucleotide sequence that, when expressed, results in the production of that polypeptide, protein or enzyme, i.e., the nucleotide sequence encodes an amino acid sequence for that polypeptide, protein or enzyme. A coding sequence is "under the control" of transcriptional and translational control sequences in a cell when RNA polymerase transcribes the coding sequence into mRNA, which is then trans-RNA spliced and translated into the protein encoded by the coding sequence. Preferably, the coding sequence is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. A gene encoding a protein of the invention for use in an expression system, whether genomic DNA or cDNA, can be isolated from any source, particularly from a human cDNA or genomic library. Methods for obtaining genes are well known in the art, e.g., Sambrook et at (supra).

A "promoter sequence" is a DNA regulatory region capable of binding RNA polymerase in a cell and initiating transcription of a downstream (3' direction) coding sequence. For purposes of defining this invention, the promoter sequence is bounded at its 3' terminus by the transcnption initiation site and extends upstream (5' direction) to include the minimum number of bases or elements necessary to initiate transcription at levels detectable above background.

Polynucleotides are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate.) Polynucleotides that hybridize include those which anneal under suitable stringency conditions and which encode polypeptides or enzymes having the same function, such as the ability to catalyze an oxidation, oxygenase, or coupling reaction of the invention.

The term "expression system" means a host cell and compatible vector under suitable conditions, e.g. for the expression of a protein coded for by foreign DNA carried by the vector and introduced to the host cell. Common expression systems include bacteria (e.g., *E. coli* and *B. subtilis*) or yeast (e.g., *S. cerevisiae*) host cells and plasmid vectors, and insect host cells and Baculovirus vectors. As used herein, a "facile expression system" means any expression system that is foreign or heterologous to a selected polynucleotide or polypeptide, and which employs host cells that can be grown or maintained more advantageously than cells that are native or heterologous to the selected polynucleotide or polypeptide, or which can produce the polypeptide more efficiently or in higher yield. For example, the use of robust prokaryotic cells to express a protein of eukaryotic origin would be a facile expression system. Preferred facile expression systems include *E. coli, B. subtilis* and *S. cerevisiae* host cells and any suitable vector.

The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA, that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes. Preferred vectors are described in the Examples, and include without limitations pcWori, pET-26b(+), pXTD14, pYEX-S1, pMAL, and pET22-b(+). Other vectors may be employed as desired by one skilled in the art. Routine experimentation in biotechnology can be used to determine which vectors are best suited for used with the invention, if different than as described in the Examples. In general, the choice of vector depends on the size of the polynucleotide sequence and the host cell to be employed in the methods of this invention.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

A polynucleotide or polypeptide is "over-expressed" when it is expressed or produced in an amount or yield that is substantially higher than a given base-line yield, e.g. a yield that occurs in nature. For example, a polypeptide is over-expressed when the yield is substantially greater than the normal, average or base-line yield of the native polypolypeptide in native host cells under given conditions, for example conditions suitable to the life cycle of the native host cells.

"Isolation" or "purification" of a polypeptide or enzyme refers to the derivation of the polypeptide by removing it from its original environment (for example, from its natural environment if it is naturally occurring, or form the host cell if it is produced by recombinant DNA methods). Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the protein or against peptides derived therefrom can be used as purification reagents. Other purification methods are possible. A purified polynucleotide or polypeptide may contain less than about 50%, preferably less than about 75%, and most preferably less than about 90%, of the cellular components with which it was originally associated. A "substantially pure" enzyme indicates the highest degree of purity which can be achieved using conventional purification techniques known in the art.

BIBLIOGRAPHY

Adam W, et al. Eur J Org Chem 2000; 16:2923-2926.
Appel D, et al. J Biotechnol 2001; 88:167-171.
Appel D, et al. J Bacteriol 2001; 88,:167-171.
Arnold F H. Acc Chem Res 1998; 3:125-131.
Ashraf W, et al. FEMS Microbiol Lett 1994; 122:1-6.
Barnes H J. In: Methods in Enzymology, Volume 272, (Eds.: Johnson E F and Waterman M R) Academic Press, San Diego, 1996, pp 3-17.
Benson S, et al. J Bacteriol 1979; 140:754-762.
Beratan, D N T. Protein Electron Transfer, 1996,Oxford: Bios Scientific Publishers.
Boddupalli S S, et al. J Biol Chem 1990; 265:4233-4239.
Boddupalli S S, et al. Arch Biochem Biophys 1992; 292:20-28.
Capdevila J H, et al. J Biol Chem 1996; 271:22663-22671.
Carmichael A B, and Wong, L L. Eur J Biochem 2001; 268: 3117-3125.
Chang Y T and Loew G. Biochemistry 2000; 39:2484-2498.
Chen H Y, et al. Science 2000; 287:1995-1997.

de Montellano (Ed.), "Cytochrome P450; Structure, Mechanism, and Biochemistry, 2nd Ed., Plenum Press, New York (1995).
Dordick J S. Biotech Progr 1992; 8:259-267.
Farinas E, et al. Adv Syn Catal 2001; 343:601-606.
Fisher M B, et al. Biochem Biophys Res Commun 1998; 248:352-355.
Fox B G, et al. Methods Enzymol 1990; 188:191-202.
Fruetel J A, et al. J Biol Chem 1994; 269:28815-28821.
Graham-Lorence S E, et al. J Biol Chem 1997: 272:1127-1135.
Green J and Dalton H. J Biol Chem 1989; 264:17698-17703.
Groves J T and Han Y-H. In: Cytochrome P450: Structure, Mechanism, and Biochemistry (Ed.: Ortiz de Montellano, P. R.), Plenum Press, New York, N.Y., 1995, pp. 3-48.
Haines D C, et al. Biochemistry 2001; 40:13456-13465.
Hartmann M, and Ernst S. Angew Chem Int Ed 2000; 39:888-890.
Joo H, et al. Nature 1999; 399:670-673.
Kim and Thomas, Bull Environ Contam Toxicol 1992; 49:879-885.
Klibanov A M. Proc Natl Acad Sci 1997; 92:10969-10976.
Kuhn-Velten, W N. Z. Naturforsch 1997; 52:132-135.
Kvittingen L, et al. Tetrahedron 1992; 48:2793-2802.
Leadbetter E R, and Foster J W. Nature 1959; 184:1428-1429.
Lewis D F V. Cytochromes P450: Structure, Function and Mechanism. 1996,London: Taylor & Francis.
Li Q, et al. Biochim Biophys Acta 2001; 1545:114-121.
Li H, and Poulos T L. Nature Struct Biol 1997; 4:140-146.
March, J. In: Advanced Organic Chemistry: Reactions, Mechanisms, and Structure 4th edition, John Wiley and Sons, New York, 1992b, pp. 1072-1074.
March, J. In: Advanced Organic Chemistry: Reactions, Mechanisms, and Structure 4th edition, John Wiley and Sons, New York, 1992a, pp. 882 - 884.
Martinez and Stewart, Curr Org Chem 2000; 4:263-282.
Miles C S, et al. Biochim Biophys Acta 2000; 1543:383-407.
Matson R S, et al. Biochem Biophys Acta 1977; 487:487-494.
Miura Y and Fulco A J. Biochim Biophys Acta 1975; 388,: 305-317.
Modi S, et al. Biochemistry 1995; 34:8982-8988.
Moser C C. et al. J Bioenerg Biomembr 1995; 27:263-274.
Munro A W, et al. Biochem Soc Trans 1993; 21:412S.
Munro A W, et al. Eur J Biochem 1996; 239:403-409.
Murrell J C, et al. Arch. Microbiol 2000; 173:325-332.
Narhi L O, and Fulco, A J. J Biol Chem 1986; 261:7160-7169.
Narhi L O, and Fulco, A J. J Biol Chem 1987; 262:6683-6690.
Noble M A, et al. Biochem J 1999; 339:371-379.
Oliver C F, et al. Biochem J 1997; 327:537-544.
Omura T, and Sato R J. J Biol Chem 1964; 239:2370-2378.
Ortiz de Montellano P R. Cytochrome P450: structure, mechanism, and biochemistry (ed. Ortiz de Montellano, P R) (Plenum Press, New York, 1995).
Ost T W, et al. FEBS Lett 2000; 486:173-177.
Paulsen M D and Ornstein R L. Proteins 1995; 21:237-243.
Peterson J A and Graham-Lorence S E, "Bacterial P450s: Structural Similarities and Functional Differences". In: Cytochrome P450: Structure, Mechanism, and Biochemistry. 2nd Ed., edited by Ortiz de Montellano, P R. Plenum Press, New York, 1995.
Ruettinger R T and Fulco A J. J Biol Chem 1981; 256:5728-5734.
Ruettinger R T, et al. J Biol Chem 1989; 264:10987-10995.
Scheller U, et al. Arch Biochem Biophys 1996; 328:245-254.
Schmid et al., Nature 2001; 409:258-268.
Schmid A, et al. J Biol Chem 1989; 264:10023-10033.
Schneider S, et al. Biotechnol Bioeng 1999; 64:333-341.
Schwaneberg U, et al. J Biomol Screening 2001; 6:111-117.
Schwaneberg U, et al. Anal Biochem 1999a; 269:359-366.
Schwaneberg U, et al. J Chromatogr A 1999b; 848:149 - 159.
Shanklin J, et al. Proc Natl Acad Sci 1997; 94:2981-2986.
Shilov A B and Shul'pin G B. Chem. Rev., 1997, 97, 2879-2932.
Staijen I E, et al. Eur J Biochem 2000; 267:1957-1965.
Stevenson J A, et al. J Am Chem Soc 1996; 118:12846-12847.
Thomas J M, et al. Acc Chem Res 2001; 34:191-200.
Tonge G M, et al. Biochem J 1977; 1161:333-344.
Watkinson R J, and Morgan P. Biodegradation 1990; 1:79-92.
Yeom, H. & Shgar, S. G. Oxygen activation by cytochrome P450BM-3: effects of mutating an active site acidic residue. Arch Biochem Biophys 337, 209-216. (1997)
Zhao H M, et al. Nature Biotechnol 1998; 16:258-261.
Zhao H, et al. In: Manual of Industrial Microbiology and Biotechnology 2nd Edition (Eds.: Demain and Davies), ASM Press, Washington D. C., 1999, pp. 597-604.
Zimmer T, et al. Biochem Biophys Res Commun 1996; 224: 784-789.

What is claimed is:

1. An isolated polypeptide having activity of a cytochrome P450 variant, wherein the variant is characterized as comprising a higher capability than the corresponding wild-type cytochrome P450 to oxidize at least one substrate selected from an alkane comprising a carbon-chain of no more than 8 carbons and an alkene comprising a carbon-chain no more than 8 carbons, and wherein the wild-type cytochrome P450 comprises an amino acid sequence having at least 90% sequence identity to SEQ ID NO: 2, and the cytochrome P450 variant comprises an amino acid substitution at two residue of SEQ ID NO:2 selected from the group consisting of V78, F87, T235, R471, E494 and S1024.

2. The isolated polypeptide of claim 1, wherein the amino acid sequence has at least 95% sequence identity to SEQ ID NO: 2.

3. The isolated polypeptide of claim 2, wherein the amino acid sequence is SEQ ID NO: 2.

4. The isolated polypeptide of claim 1, wherein the higher capability is a higher maximum turnover rate of the substrate into an oxidized product.

5. The isolated polypeptide of claim 4, wherein the maximum turnover rate of the variant is at least 5-10 times the maximum turnover rate of the wild-type.

6. The isolated polypeptide of claim 5, wherein the substrate is an alkane and the capability to oxidize is capability to hydroxylate.

7. The isolated polypeptide of claim 1, wherein the amino acid substitution is selected from V78A, F87A, T235A, R471A, E494K and S1024E.

8. The isolated polypeptide of claim 3, wherein the cytochrome P450 variant comprises amino acid substitutions at V78 and F87.

9. The isolated polypeptide of claim 7, wherein the cytochrome P450 variant comprises at least one further amino acid substitution at a residue selected from H138, T175, V178, A184, N186, F205, D217, S226, R255, A290, A295, L353, and G396.

10. The isolated polypeptide of claim 9, wherein the at least one further amino acid substitution is selected from H138Y, T175I, V178I, A184V, N186D, F205C, D217V, S226I, S226R, R255S, A290V, A295T, L353V, and G396M.

* * * * *

UNITED STATES PATENT AND TRADEMARK OFFICE

CERTIFICATE OF CORRECTION

PATENT NO. : 8,076,114 B2
APPLICATION NO. : 12/754216
DATED : December 13, 2011
INVENTOR(S) : Edgardo T. Farinas et al.

It is certified that error appears in the above-identified patent and that said Letters Patent is hereby corrected as shown below:

Please insert immediately below the title in column 1:

--This invention was made with Government Support under Grant Nos. DBI-9807460 (ETF) and BES-9981770 (FHA) awarded by the National Science Foundation. The U.S. Government has certain rights in this invention.--

Signed and Sealed this
Tenth Day of January, 2012

David J. Kappos
*Director of the United States Patent and Trademark Office*